United States Patent [19]
Gonez et al.

[11] Patent Number: 6,066,472
[45] Date of Patent: May 23, 2000

[54] NUCLEIC ACIDS CODING FOR GLM-2, A NOVEL PROTEIN TYROSINE PHOSPHATASE

[75] Inventors: Leonel Jorge Gonez, Hughesdale, Australia; Jan Saras, Uppsala, Sweden; Lena Claesson-Welsh, Uppsala, Sweden; Carl-Henrik Heldin, Uppsala, Sweden

[73] Assignee: Ludwig Institute for Cancer Research, New York, N.Y.

[21] Appl. No.: 09/100,804

[22] Filed: Jun. 19, 1998

Related U.S. Application Data

[62] Division of application No. 08/596,291, filed as application No. PCT/US94/09943, Sep. 1, 1994, which is a continuation of application No. 08/115,573, Sep. 1, 1993, abandoned.

[51] Int. Cl.[7] .............................. C12N 15/52; C12N 1/21; C12N 5/10; C12N 15/63
[52] U.S. Cl. ................. 435/69.1; 435/320.1; 435/252.3; 435/325; 435/196; 536/23.5
[58] Field of Search ..................... 435/69.1, 325, 435/254.11, 252.3, 320.1, 196; 536/23.5, 24.31

[56] References Cited

FOREIGN PATENT DOCUMENTS 203969    8/1995    Japan .

*Primary Examiner*—Elizabeth Kemmerer
*Attorney, Agent, or Firm*—Wolf, Greenfield & Sacks, P.C.

[57] ABSTRACT

The invention relates to the cloning of two novel protein tyrosine phosphatases. Nucleic acid sequences encoding these phosphatases (PTPL1 and GLM-2) as well as antisense sequences are also provided. The recombinantly produced PTPL1 and GLM-2 proteins also are provided, as well as antibodies to these proteins. Methods relating to isolating the phosphatases, using the nucleic acid sequences, and using the phosphatases also are provided.

12 Claims, 5 Drawing Sheets

Fig. 1A

```
MEHYLPARVME--KLDLSYIKEELPKLHNTYVVGASEKETELEFLKVCQRLTEY    PTPL1
SERLIPQRVMDQHKLTRDQWEDRIQVWHAEHRGMLKDNAMLEYLKIAQDLEMY    Ezrin
DFKLAPNQ------TKELEEKVMELHKSYRSMTPAQADLEFLENAKKLSMY      Band 4.1
DYSFIPNQ------PQDFEKEIAKLHQQHIGLSPAEAEFNYLNTARTLELY      PTPase MEG
DSHFIPDQ------NEDFLTKVESLHEQHSGLKQSEAESCYINIARTLDFY      PTPH1

GVHFHRVHPEKKSQTGILLGVCSKGVLVFEVHNGVRTLVLRFPWRETKKISFS    PTPL1
GINYFEIK---NKKGTDLWLGVDALGLNIYEKDDKLTPKI-GFPWSEIRNISFN   Ezrin
GVDLHKAK---DLEGVDILGVCSSGLLVYKDKLRINR-----FPWPKVLKISYK   BAND 4.1
GVEFHYAR---DQSNNEIMIGVMSGGILIYKNRVRMNT-----FPWLKIVKISFK  PTPase MEG
GVELHSGR---DLHNLDLMIGIASAGVAVYRKYICTSF-----YPWVNILKISFK  PTPH1

KKKITLQNTSDGIKH------GFQTDNSKICQYLLHLCSYQHKFQLQMR--AR    PTPL1
DKKFVIKP----IDKKAPDFVFYAPRLRINKRILQLCMGNHELYMRRRKPDTI    Ezrin
RSFFIKIRPGEQEQYESTIGFKLPSYRAAKKLWKVCVEHHTFF-RLTSTDTI     Band 4.1
CKQFFIQLRKELHESRETLLGFNMVNYRACKNLWKACVEHHTFF-RLDRPLPP    PTPase MEG
RKKFFIHQRQKQAESREHIVAFNMLNYRSCKNLWKSCVEHHTFF-QAKKLLPQ    PTPH1
```

Fig. 1B

```
PTPL1     1  DAKYGLGFQIIGGEK       MGRLDLGIFISSVAPGGPADFH  GCLKPGDRLISV  NSV  SLEGVSEHAAIEILQNAPEDVTLVI
          2  KNDNSLOISVTGGVN       TSVRHGGIYVKAVIPQGAAESD  GRIHKGDRVLAV  NGV  SLEGATEKQAVETLRNTGQVVHLLL
          3  KNSSGLGFSFSREDNLIPEQINASIVRVKKLFAGQPAAES     GKIDVGDVILKV  NGA  SLKGLSQQEVISALRGTAPEVFLLL
          4  SEKASLGFTVTKGNQ         RIGCYVHDVI QDPAKSD  GRLKPGDRLIKV  NDT  DVTNMTHTDAVNLLRAASKTVRLVI
          5  CNKBELGFSLCGGHD       SLYQVVIISDINPRSVAAIE    GNLQLLDVIHYV  NGV  STQGMTLEEVNRALDMSLPSLVLKA

PTPH1        DEDGKPGFNLKGGVD       QKNPLVVSRINPSSPADTCIPKLNEGDQIVLI            NGR  DISEHTHDQVVMFIKASRESHSREL
PTPase MEG   DENGRFGFNVKGGYD       QKMPVIVSRVAPQTPADLCVPRLNEGDQVVLI            NGR  DIAEHTHDQVVLFIKASCERHSGEL dlg-A     1  RGNSGLGFSIAGGTDNPHI   GTDTSIYITKLISGAAAAD    GRLSINDIIVSV  NDV  SVVDVPHASAVDALKKAGNVVKLHV
          2  KGGKGLGFSIAGGIGNQHI   PGDNGIYVTKLTDGGRAQVD   GRLSIGDKLIAVRTNGSEKNLENVTHELAVATLKSITDKVTLII
          3  KGPQGLGFNIVGGED       GQGIYVSFILAGGPADLG     SELKRGDQLLSV  NNV  NLTHATHEEAAQALKTSGGVVTLLA PSD-95    1  RGNSGLGFSIAGGTDNPHI   GDDPSIFITKIIPGGAAAQD   GRLRVNDSILFV  NEV  DVREVTHSAAVEALKEAGSIVRLYV
          2  KGPKGLGFSIAGGVGNQHI   PGDNSIYVTKIIEGGAAHKD   GRLQIGDKILAV  NSV  GLEDVMHEDAVAALKNTYDVVYLKV
          3  RGSTGLGFNIVGGED       GEGIFISFILAGGPADLS     GELRKGDQILSV  NGV  DLRNASHEQAAIALKNAGQTVTIIA 220-KD    1  HRAPGFGIAISGGRDNPHFQSGETSIVISDVLKGGPAB                     GQLQENNRVAMV  NGV  SMDNVEHAFAVQQLRKSGKNAKITI
          2  RKNEEYGLRPASH             IFVKEISQDSLAARD     GDIQEGDVVLKI  NGT  VTENMSLTDAKTLIERSKGKLKMVV
          3  RKGDSVGLRLAGGND       VGIFVAGVLEDSPAAKE  G LEEGDQILRV  NNV  DFTNIIREEAVLFLLDLPKGEEVTI p55          VTEEPMGITLKLNEK       QSCTVARILHGGMIHRQ      GSLHVGDEILEI  NGT  NVTNHSVDQLQKAMKETKGMISLKV
NOS          RKVGGLGFLVKERVS       PKKVIISDLIRGGAAEQS     GLIQAGDIILAV  NDR  PLVDLSYDSALEVLRGIASETHVVL
0118(ROS)    EDHEOLGISITGGLE       HGVPILISGIHPGQPADRC    GGLHVGDAILAV  NGV  NLRDTLHLGAVTILSQQRGEIEFEV
```

Fig. 2

SEQUENCE LISTING (1) GENERAL INFORMATION:

(iii) NUMBER OF SEQUENCES: 34

(2) INFORMATION FOR SEQ ID NO:1:

(i) SEQUENCE CHARACTERISTICS:
        (A) LENGTH: 8040 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HOMO SAPIENS (ix) FEATURE:
        (A) NAME/KEY: CDS
        (B) LOCATION: 78..7475

(xi) SEQUENCE DESCRIPTION: SEQ ID NO:1:

```
CCCGCCCCGA CGCCGCGTCC CTGCAGCCCT GCCCGGCGCT CCAGTAGCAG GACCCGGTCT      60
```

-continued

```
CGGGACCAGC CGGTAAT ATG CAC GTG TCA CTA GCT GAG GCC CTG GAG GTT              110
                Met His Val Ser Leu Ala Glu Ala Leu Glu Val
                 1               5                  10

CGG GGT GGA CCA CTT CAG GAG GAA GAA ATA TGG GCT GTA TTA AAT CAA             158
Arg Gly Gly Pro Leu Gln Glu Glu Glu Ile Trp Ala Val Leu Asn Gln
                 15                  20                  25

AGT GCT GAA AGT CTC CAA GAA TTA TTC AGA AAA GTA AGC CTA GCT GAT             206
Ser Ala Glu Ser Leu Gln Glu Leu Phe Arg Lys Val Ser Leu Ala Asp
             30                  35                  40

CCT GCT GCC CTT GGC TTC ATC ATT TCT CCA TGG TCT CTG CTG TTG CTG             254
Pro Ala Ala Leu Gly Phe Ile Ile Ser Pro Trp Ser Leu Leu Leu Leu
         45                  50                  55

CCA TCT GGT AGT GTG TCA TTT ACA GAT GAA AAT ATT TCC AAT CAG GAT             302
Pro Ser Gly Ser Val Ser Phe Thr Asp Glu Asn Ile Ser Asn Gln Asp
 60                  65                  70                  75

CTT CGA GCA TTC ACT GCA CCA GAG GTT CTT CAA AAT CAG TCA CTA ACT             350
Leu Arg Ala Phe Thr Ala Pro Glu Val Leu Gln Asn Gln Ser Leu Thr
                     80                  85                  90

TCT CTC TCA GAT GTT GAA AAG ATC CAC ATT TAT TCT CTT GGA ATG ACA             398
Ser Leu Ser Asp Val Glu Lys Ile His Ile Tyr Ser Leu Gly Met Thr
                 95                 100                 105

CTG TAT TGG GGG GCT GAT TAT GAA GTG CCT CAG AGC CAA CCT ATT AAG             446
Leu Tyr Trp Gly Ala Asp Tyr Glu Val Pro Gln Ser Gln Pro Ile Lys
             110                 115                 120

CTT GGA GAT CAT CTC AAC AGC ATA CTG CTT GGA ATG TGT GAG GAT GTT             494
Leu Gly Asp His Leu Asn Ser Ile Leu Leu Gly Met Cys Glu Asp Val
         125                 130                 135

ATT TAC GCT CGA GTT TCT GTT CGG ACT GTG CTG GAT GCT TGC AGT GCC             542
Ile Tyr Ala Arg Val Ser Val Arg Thr Val Leu Asp Ala Cys Ser Ala
140                 145                 150                 155

CAC ATT AGG AAT AGC AAT TGT GCA CCC TCA TTT TCC TAC GTG AAA CAC             590
His Ile Arg Asn Ser Asn Cys Ala Pro Ser Phe Ser Tyr Val Lys His
                 160                 165                 170

TTG GTA AAA CTG GTT CTG GGA AAT CTT TCT GGG ACA GAT CAG CTT TCC             638
Leu Val Lys Leu Val Leu Gly Asn Leu Ser Gly Thr Asp Gln Leu Ser
             175                 180                 185

TGT AAC AGT GAA CAA AAG CCT GAT CGA AGC CAG GCT ATT CGA GAT CGA             686
Cys Asn Ser Glu Gln Lys Pro Asp Arg Ser Gln Ala Ile Arg Asp Arg
         190                 195                 200

TTG CGA GGA AAA GGA TTA CCA ACA GGA AGA AGC TCT ACT TCT GAT GTA             734
Leu Arg Gly Lys Gly Leu Pro Thr Gly Arg Ser Ser Thr Ser Asp Val
205                 210                 215

CTA GAC ATA CAA AAG CCT CCA CTC TCT CAT CAG ACC TTT CTT AAC AAA             782
Leu Asp Ile Gln Lys Pro Pro Leu Ser His Gln Thr Phe Leu Asn Lys
220                 225                 230                 235

GGG CTT AGT AAA TCT ATG GGA TTT CTG TCC ATC AAA GAT ACA CAA GAT             830
Gly Leu Ser Lys Ser Met Gly Phe Leu Ser Ile Lys Asp Thr Gln Asp
                 240                 245                 250

GAG AAT TAT TTC AAG GAC ATT TTA TCA GAT AAT TCT GGA CGT GAA GAT             878
Glu Asn Tyr Phe Lys Asp Ile Leu Ser Asp Asn Ser Gly Arg Glu Asp
             255                 260                 265

TCT GAA AAT ACA TTC TGC CCT TAC CAG TTC AAA ACT AGT GGC CCA GAA             926
Ser Glu Asn Thr Phe Cys Pro Tyr Gln Phe Lys Thr Ser Gly Pro Glu
         270                 275                 280

AAA AAA CCC ATC CCT GGC ATT GAT GTG CTT TCT AAG AAG AAG ATC TGG             974
Lys Lys Pro Ile Pro Gly Ile Asp Val Leu Ser Lys Lys Lys Ile Trp
285                 290                 295
```

-continued

| | |
|---|---|
| GCT TCA TCC ATG GAC TTG CTT TGT ACA GCT GAC AGA GAC TTC TCT TCA<br>Ala Ser Ser Met Asp Leu Leu Cys Thr Ala Asp Arg Asp Phe Ser Ser<br>300                    305                    310                    315 | 1022 |
| GGA GAG ACT GCC ACA TAT CGT CGT TGT CAC CCT GAG GCA GTA ACA GTG<br>Gly Glu Thr Ala Thr Tyr Arg Arg Cys His Pro Glu Ala Val Thr Val<br>                    320                    325                    330 | 1070 |
| CGG ACT TCA ACT ACG CCT AGA AAA AAG GAG GCA AGA TAC TCA GAT GGA<br>Arg Thr Ser Thr Thr Pro Arg Lys Lys Glu Ala Arg Tyr Ser Asp Gly<br>              335                    340                    345 | 1118 |
| AGT ATA GCC TTG GAT ATC TTT GGC CCT CAG AAA ATG GAT CCA ATA TAT<br>Ser Ile Ala Leu Asp Ile Phe Gly Pro Gln Lys Met Asp Pro Ile Tyr<br>            350                    355                    360 | 1166 |
| CAC ACT CGA GAA TTG CCC ACC TCC TCA GCA ATA TCA AGT GCT TTG GAC<br>His Thr Arg Glu Leu Pro Thr Ser Ser Ala Ile Ser Ser Ala Leu Asp<br>365                    370                    375 | 1214 |
| CGA ATC CGA GAG AGA CAA AAG AAA CTT CAG GTT CTG AGG GAA GCC ATG<br>Arg Ile Arg Glu Arg Gln Lys Lys Leu Gln Val Leu Arg Glu Ala Met<br>380                    385                    390                    395 | 1262 |
| AAT GTA GAA GAA CCA GTT CGA AGA TAC AAA ACT TAT CAT GGT GAT GTC<br>Asn Val Glu Glu Pro Val Arg Arg Tyr Lys Thr Tyr His Gly Asp Val<br>                    400                    405                    410 | 1310 |
| TTT AGT ACC TCC AGT GAA AGT CCA TCT ATT ATT TCC TCT GAA TCA GAT<br>Phe Ser Thr Ser Ser Glu Ser Pro Ser Ile Ile Ser Ser Glu Ser Asp<br>              415                    420                    425 | 1358 |
| TTC AGA CAA GTG AGA AGA AGT GAA GCC TCA AAG AGG TTT GAA TCC AGC<br>Phe Arg Gln Val Arg Arg Ser Glu Ala Ser Lys Arg Phe Glu Ser Ser<br>            430                    435                    440 | 1406 |
| AGT GGT CTC CCA GGG GTA GAT GAA ACC TTA AGT CAA GGC CAG TCA CAG<br>Ser Gly Leu Pro Gly Val Asp Glu Thr Leu Ser Gln Gly Gln Ser Gln<br>445                    450                    455 | 1454 |
| AGA CCG AGC AGA CAA TAT GAA ACA CCC TTT GAA GGC AAC TTA ATT AAT<br>Arg Pro Ser Arg Gln Tyr Glu Thr Pro Phe Glu Gly Asn Leu Ile Asn<br>460                    465                    470                    475 | 1502 |
| CAA GAG ATC ATG CTA AAA CGG CAA GAG GAA GAA CTG ATG CAG CTA CAA<br>Gln Glu Ile Met Leu Lys Arg Gln Glu Glu Glu Leu Met Gln Leu Gln<br>                    480                    485                    490 | 1550 |
| GCC AAA ATG GCC CTT AGA CAG TCT CGG TTG AGC CTA TAT CCA GGA GAC<br>Ala Lys Met Ala Leu Arg Gln Ser Arg Leu Ser Leu Tyr Pro Gly Asp<br>            495                    500                    505 | 1598 |
| ACA ATC AAA GCG TCC ATG CTT GAC ATC ACC AGG GAT CCG TTA AGA GAA<br>Thr Ile Lys Ala Ser Met Leu Asp Ile Thr Arg Asp Pro Leu Arg Glu<br>            510                    515                    520 | 1646 |
| ATT GCC CTA GAA ACA GCC ATG ACT CAA AGA AAA CTG AGG AAT TTC TTT<br>Ile Ala Leu Glu Thr Ala Met Thr Gln Arg Lys Leu Arg Asn Phe Phe<br>525                    530                    535 | 1694 |
| GGC CCT GAG TTT GTG AAA ATG ACA ATT GAA CCA TTT ATA TCT TTG GAT<br>Gly Pro Glu Phe Val Lys Met Thr Ile Glu Pro Phe Ile Ser Leu Asp<br>540                    545                    550                    555 | 1742 |
| TTG CCA CGG TCT ATT CTT ACT AAG AAA GGG AAG AAT GAG GAT AAC CGA<br>Leu Pro Arg Ser Ile Leu Thr Lys Lys Gly Lys Asn Glu Asp Asn Arg<br>              560                    565                    570 | 1790 |
| AGG AAA GTA AAC ATA ATG CTT CTG AAC GGG CAA AGA CTG GAA CTG ACC<br>Arg Lys Val Asn Ile Met Leu Leu Asn Gly Gln Arg Leu Glu Leu Thr<br>            575                    580                    585 | 1838 |
| TGT GAT ACC AAA ACT ATA TGT AAA GAT GTG TTT GAT ATG GTT GTG GCA<br>Cys Asp Thr Lys Thr Ile Cys Lys Asp Val Phe Asp Met Val Val Ala<br>            590                    595                    600 | 1886 |

-continued

| | |
|---|---|
| CAT ATT GGC TTA GTA GAG CAT CAT TTG TTT GCT TTA GCT ACC CTC AAA<br>His Ile Gly Leu Val Glu His His Leu Phe Ala Leu Ala Thr Leu Lys<br>605                         610                         615 | 1934 |
| GAT AAT GAA TAT TTC TTT GTT GAT CCT GAC TTA AAA TTA ACC AAA GTG<br>Asp Asn Glu Tyr Phe Phe Val Asp Pro Asp Leu Lys Leu Thr Lys Val<br>620                         625                         630                         635 | 1982 |
| GCC CCA GAG GGA TGG AAA GAA GAA CCA AAG AAA AAG ACC AAA GCC ACT<br>Ala Pro Glu Gly Trp Lys Glu Glu Pro Lys Lys Lys Thr Lys Ala Thr<br>                    640                         645                         650 | 2030 |
| GTT AAT TTT ACT TTG TTT TTC AGA ATT AAA TTT TTT ATG GAT GAT GTT<br>Val Asn Phe Thr Leu Phe Phe Arg Ile Lys Phe Phe Met Asp Asp Val<br>               655                         660                         665 | 2078 |
| AGT CTA ATA CAA CAT ACT CTG ACG TGT CAT CAG TAT TAC CTT CAG CTT<br>Ser Leu Ile Gln His Thr Leu Thr Cys His Gln Tyr Tyr Leu Gln Leu<br>670                         675                         680 | 2126 |
| CGA AAA GAT ATT TTG GAG GAA AGG ATG CAC TGT GAT GAT GAG ACT TCC<br>Arg Lys Asp Ile Leu Glu Glu Arg Met His Cys Asp Asp Glu Thr Ser<br>     685                       690                         695 | 2174 |
| TTA TTG CTG GCA TCC TTG GCT CTC CAG GCT GAG TAT GGA GAT TAT CAA<br>Leu Leu Leu Ala Ser Leu Ala Leu Gln Ala Glu Tyr Gly Asp Tyr Gln<br>700                         705                         710                         715 | 2222 |
| CCA GAG GTT CAT GGT GTG TCT TAC TTT AGA ATG GAG CAC TAT TTG CCC<br>Pro Glu Val His Gly Val Ser Tyr Phe Arg Met Glu His Tyr Leu Pro<br>                    720                         725                         730 | 2270 |
| GCC AGA GTG ATG GAG AAA CTT GAT TTA TCC TAT ATC AAA GAA GAG TTA<br>Ala Arg Val Met Glu Lys Leu Asp Leu Ser Tyr Ile Lys Glu Glu Leu<br>               735                         740                         745 | 2318 |
| CCC AAA TTG CAT AAT ACC TAT GTG GGA GCT TCT GAA AAA GAG ACA GAG<br>Pro Lys Leu His Asn Thr Tyr Val Gly Ala Ser Glu Lys Glu Thr Glu<br>750                         755                         760 | 2366 |
| TTA GAA TTT TTA AAG GTC TGC CAA AGA CTG ACA GAA TAT GGA GTT CAT<br>Leu Glu Phe Leu Lys Val Cys Gln Arg Leu Thr Glu Tyr Gly Val His<br>     765                       770                         775 | 2414 |
| TTT CAC CGA GTG CAC CCT GAG AAG AAG TCA CAA ACA GGA ATA TTG CTT<br>Phe His Arg Val His Pro Glu Lys Lys Ser Gln Thr Gly Ile Leu Leu<br>780                         785                         790                         795 | 2462 |
| GGA GTC TGT TCT AAA GGT GTC CTT GTG TTT GAA GTT CAC AAT GGA GTG<br>Gly Val Cys Ser Lys Gly Val Leu Val Phe Glu Val His Asn Gly Val<br>                    800                         805                         810 | 2510 |
| CGC ACA TTG GTC CTT CGC TTT CCA TGG AGG GAA ACC AAG AAA ATA TCT<br>Arg Thr Leu Val Leu Arg Phe Pro Trp Arg Glu Thr Lys Lys Ile Ser<br>               815                         820                         825 | 2558 |
| TTT TCT AAA AAG AAA ATC ACA TTG CAA AAT ACA TCA GAT GGA ATA AAA<br>Phe Ser Lys Lys Lys Ile Thr Leu Gln Asn Thr Ser Asp Gly Ile Lys<br>830                         835                         840 | 2606 |
| CAT GGC TTC CAG ACA GAC AAC AGT AAG ATA TGC AGT ACC TG CTG CAC<br>His Gly Phe Gln Thr Asp Asn Ser Lys Ile Cys Gln Tyr Leu Leu His<br>     845                       850                         855 | 2654 |
| CTC TGC TCT TAC CAG CAT AAG TTC CAG CTA CAG ATG AGA GCA AGA CAG<br>Leu Cys Ser Tyr Gln His Lys Phe Gln Leu Gln Met Arg Ala Arg Gln<br>860                         865                         870                         875 | 2702 |
| AGC AAC CAA GAT GCC CAA GAT ATT GAG AGA GCT TCG TTT AGG AGC CTG<br>Ser Asn Gln Asp Ala Gln Asp Ile Glu Arg Ala Ser Phe Arg Ser Leu<br>                    880                         885                         890 | 2750 |
| AAT CTC CAA GCA GAG TCT GTT AGA GGA TTT AAT ATG GGA CGA GCA ATC<br>Asn Leu Gln Ala Glu Ser Val Arg Gly Phe Asn Met Gly Arg Ala Ile<br>               895                         900                         905 | 2798 |

```
AGC ACT GGC AGT CTG GCC AGC AGC ACC CTC AAC AAA CTT GCT GTT CGA    2846
Ser Thr Gly Ser Leu Ala Ser Ser Thr Leu Asn Lys Leu Ala Val Arg
        910                 915                 920

CCT TTA TCA GTT CAA GCT GAG ATT CTG AAG AGG CTA TCC TGC TCA GAG    2894
Pro Leu Ser Val Gln Ala Glu Ile Leu Lys Arg Leu Ser Cys Ser Glu
    925                 930                 935

CTG TCG CTT TAC CAG CCA TTG CAA AAC AGT TCA AAA GAG AAG AAT GAC    2942
Leu Ser Leu Tyr Gln Pro Leu Gln Asn Ser Ser Lys Glu Lys Asn Asp
940                 945                 950                 955

AAA GCT TCA TGG GAG GAA AAG CCT AGA GAG ATG AGT AAA TCA TAC CAT    2990
Lys Ala Ser Trp Glu Glu Lys Pro Arg Glu Met Ser Lys Ser Tyr His
                960                 965                 970

GAT CTC AGT CAG GCC TCT CTC TAT CCA CAT CGG AAA AAT GTC ATT GTT    3038
Asp Leu Ser Gln Ala Ser Leu Tyr Pro His Arg Lys Asn Val Ile Val
            975                 980                 985

AAC ATG GAA CCC CCA CCA CAA ACC GTT GCA GAG TTG GTG GGA AAA CCT    3086
Asn Met Glu Pro Pro Pro Gln Thr Val Ala Glu Leu Val Gly Lys Pro
        990                 995                 1000

TCT CAC CAG ATG TCA AGA TCT GAT GCA GAA TCT TTG GCA GGA GTG ACA    3134
Ser His Gln Met Ser Arg Ser Asp Ala Glu Ser Leu Ala Gly Val Thr
    1005                1010                1015

AAA CTT AAT AAT TCA AAG TCT GTT GCG AGT TTA AAT AGA AGT CCT GAA    3182
Lys Leu Asn Asn Ser Lys Ser Val Ala Ser Leu Asn Arg Ser Pro Glu
1020                1025                1030                1035

AGG AGG AAA CAT GAA TCA GAC TCC TCA TCC ATT GAA GAC CCT GGG CAA    3230
Arg Arg Lys His Glu Ser Asp Ser Ser Ser Ile Glu Asp Pro Gly Gln
                1040                1045                1050

GCA TAT GTT CTA GAT GTG CTA CAC AAA AGA TGG AGC ATA GTA TCT TCA    3278
Ala Tyr Val Leu Asp Val Leu His Lys Arg Trp Ser Ile Val Ser Ser
            1055                1060                1065

CCA GAA AGG GAG ATC ACC TTA GTG AAC CTG AAA AAA GAT GCA AAG TAT    3326
Pro Glu Arg Glu Ile Thr Leu Val Asn Leu Lys Lys Asp Ala Lys Tyr
        1070                1075                1080

GGC TTG GGA TTT CAA ATT ATT GGT GGG GAG AAG ATG GAG ACT GAC CTA    3374
Gly Leu Gly Phe Gln Ile Ile Gly Gly Glu Lys Met Glu Thr Asp Leu
    1085                1090                1095

GGC ATA TTT ATC AGC TCA GTT GCC CCT GGA GGA CCA GCT GAC TTC CAT    3422
Gly Ile Phe Ile Ser Ser Val Ala Pro Gly Gly Pro Ala Asp Phe His
1100                1105                1110                1115

GGA TGC TTG AAG CCA GGA GAC CGT TTG ATA TCT GTG AAT AGT GTG AGT    3470
Gly Cys Leu Lys Pro Gly Asp Arg Leu Ile Ser Val Asn Ser Val Ser
                1120                1125                1130

CTG GAG GGA GTC AGC CAC CAT GCT GCA ATT GAA ATT TTG CAA AAT GCA    3518
Leu Glu Gly Val Ser His His Ala Ala Ile Glu Ile Leu Gln Asn Ala
            1135                1140                1145

CCT GAA GAT GTG ACA CTT GTT ATC TCT CAG CCA AAA GAA AAG ATA TCC    3566
Pro Glu Asp Val Thr Leu Val Ile Ser Gln Pro Lys Glu Lys Ile Ser
        1150                1155                1160

AAA GTG CCT TCT ACT CCT GTG CAT CTC ACC AAT GAG ATG AAA AAC TAC    3614
Lys Val Pro Ser Thr Pro Val His Leu Thr Asn Glu Met Lys Asn Tyr
    1165                1170                1175

ATG AAG AAA TCT TCC TAC ATG CAA GAC AGT GCT ATA GAT TCT TCT TCC    3662
Met Lys Lys Ser Ser Tyr Met Gln Asp Ser Ala Ile Asp Ser Ser Ser
1180                1185                1190                1195

AAG GAT CAC CAC TGG TCA CGT GGT ACC CTG AGG CAC ATC TCG GAG AAC    3710
Lys Asp His His Trp Ser Arg Gly Thr Leu Arg His Ile Ser Glu Asn
                1200                1205                1210
```

```
TCC TTT GGG CCG TCT GGG GGC CTG CGG GAA GGA AGC CTG AGT TCT CAA    3758
Ser Phe Gly Pro Ser Gly Gly Leu Arg Glu Gly Ser Leu Ser Ser Gln
            1215                1220                1225

GAT TCC AGG ACT GAG AGT GCC AGC TTG TCT CAA AGC CAG GTC AAT GGT    3806
Asp Ser Arg Thr Glu Ser Ala Ser Leu Ser Gln Ser Gln Val Asn Gly
            1230                1235                1240

TTC TTT GCC AGC CAT TTA GGT GAC CAA ACC TGG CAG GAA TCA CAG CAT    3854
Phe Phe Ala Ser His Leu Gly Asp Gln Thr Trp Gln Glu Ser Gln His
            1245                1250                1255

GGC AGC CCT TCC CCA TCT GTA ATA TCC AAA GCC ACC GAG AAA GAG ACT    3902
Gly Ser Pro Ser Pro Ser Val Ile Ser Lys Ala Thr Glu Lys Glu Thr
1260                1265                1270                1275

TTC ACT GAT AGT AAC CAA AGC AAA ACT AAA AAG CCA GGC ATT TCT GAT    3950
Phe Thr Asp Ser Asn Gln Ser Lys Thr Lys Lys Pro Gly Ile Ser Asp
            1280                1285                1290

GTA ACT GAT TAC TCA GAC CGT GGA GAT TCA GAC ATG GAT GAA GCC ACT    3998
Val Thr Asp Tyr Ser Asp Arg Gly Asp Ser Asp Met Asp Glu Ala Thr
            1295                1300                1305

TAC TCC AGC AGT CAG GAT CAT CAA ACA CCA AAA CAG GAA TCT TCC TCT    4046
Tyr Ser Ser Ser Gln Asp His Gln Thr Pro Lys Gln Glu Ser Ser Ser
            1310                1315                1320

TCA GTG AAT ACA TCC AAC AAG ATG AAT TTT AAA ACT TTT TCT TCA TCA    4094
Ser Val Asn Thr Ser Asn Lys Met Asn Phe Lys Thr Phe Ser Ser Ser
            1325                1330                1335

CCT CCT AAG CCT GGA GAT ATC TTT GAG GTT GAA CTG GCT AAA AAT GAT    4142
Pro Pro Lys Pro Gly Asp Ile Phe Glu Val Glu Leu Ala Lys Asn Asp
1340                1345                1350                1355

AAC AGC TTG GGG ATA AGT GTC ACG GGA GGT GTG AAT ACG AGT GTC AGA    4190
Asn Ser Leu Gly Ile Ser Val Thr Gly Gly Val Asn Thr Ser Val Arg
            1360                1365                1370

CAT GGT GGC ATT TAT GTG AAA GAT GTT ATT CCC CAG GGA GCA GCA GAG    4238
His Gly Gly Ile Tyr Val Lys Asp Val Ile Pro Gln Gly Ala Ala Glu
            1375                1380                1385

TCT GAT GGT AGA ATT CAC AAA GGT GAT CGC GTC CTA GCT GTC AAT GGA    4286
Ser Asp Gly Arg Ile His Lys Gly Asp Arg Val Leu Ala Val Asn Gly
            1390                1395                1400

GTT AGT CTA GAA GGA GCC ACC CAT AAG CAA GCT GTG GAA ACA CTG AGA    4334
Val Ser Leu Glu Gly Ala Thr His Lys Gln Ala Val Glu Thr Leu Arg
            1405                1410                1415

AAT ACA GGA CAG GTG GTT CAT CTG TTA TTA GAA AAG GGA CAA TCT CCA    4382
Asn Thr Gly Gln Val Val His Leu Leu Leu Glu Lys Gly Gln Ser Pro
1420                1425                1430                1435

ACA TCT AAA GAA CAT GTC CCG GTA ACC CCA CAG TGT ACC CTT TCA GAT    4430
Thr Ser Lys Glu His Val Pro Val Thr Pro Gln Cys Thr Leu Ser Asp
            1440                1445                1450

CAG AAT GCC CAA GGT CAA GGC CCA GAA AAA GTG AAG AAA ACA ACT CAG    4478
Gln Asn Ala Gln Gly Gln Gly Pro Glu Lys Val Lys Lys Thr Thr Gln
            1455                1460                1465

GTC AAA GAC TAC AGC TTT GTC ACT GAA GAA AAT ACA TTT GAG GTA AAA    4526
Val Lys Asp Tyr Ser Phe Val Thr Glu Glu Asn Thr Phe Glu Val Lys
            1470                1475                1480

TTA TTT AAA AAT AGC TCA GGT CTA GGA TTC AGT TTT TCT CGA GAA GAT    4574
Leu Phe Lys Asn Ser Ser Gly Leu Gly Phe Ser Phe Ser Arg Glu Asp
            1485                1490                1495

AAT CTT ATA CCG GAG CAA ATT AAT GCC AGC ATA GTA AGG GTT AAA AAG    4622
Asn Leu Ile Pro Glu Gln Ile Asn Ala Ser Ile Val Arg Val Lys Lys
1500                1505                1510                1515
```

```
CTC TTT GCT GGA CAG CCA GCA GCA GAA AGT GGA AAA ATT GAT GTA GGA      4670
Leu Phe Ala Gly Gln Pro Ala Ala Glu Ser Gly Lys Ile Asp Val Gly
            1520                1525                1530

GAT GTT ATC TTG AAA GTG AAT GGA GCC TCT TTG AAA GGA CTA TCT CAG      4718
Asp Val Ile Leu Lys Val Asn Gly Ala Ser Leu Lys Gly Leu Ser Gln
        1535                1540                1545

CAG GAA GTC ATA TCT GCT CTC AGG GGA ACT GCT CCA GAA GTA TTC TTG      4766
Gln Glu Val Ile Ser Ala Leu Arg Gly Thr Ala Pro Glu Val Phe Leu
    1550                1555                1560

CTT CTC TGC AGA CCT CCA CCT GGT GTG CTA CCG GAA ATT GAT ACT GCG      4814
Leu Leu Cys Arg Pro Pro Pro Gly Val Leu Pro Glu Ile Asp Thr Ala
1565                1570                1575

CTT TTG ACC CCA CTT CAG TCT CCA GCA CAA GTA CTT CCA AAC AGC AGT      4862
Leu Leu Thr Pro Leu Gln Ser Pro Ala Gln Val Leu Pro Asn Ser Ser
1580                1585                1590                1595

AAA GAC TCT TCT CAG CCA TCA TGT GTG GAG CAA AGC ACC AGC TCA GAT      4910
Lys Asp Ser Ser Gln Pro Ser Cys Val Glu Gln Ser Thr Ser Ser Asp
            1600                1605                1610

GAA AAT GAA ATG TCA GAC AAA AGC AAA AAA CAG TGC AAG TCC CCA TCC      4958
Glu Asn Glu Met Ser Asp Lys Ser Lys Lys Gln Cys Lys Ser Pro Ser
        1615                1620                1625

AGA AGA GAC AGT TAC AGT GAC AGC AGT GGG AGT GGA GAA GAT GAC TTA      5006
Arg Arg Asp Ser Tyr Ser Asp Ser Ser Gly Ser Gly Glu Asp Asp Leu
    1630                1635                1640

GTC ACA GCT CCA GCA AAC ATA TCA AAT TCG ACC TGG AGT TCA GCT TTG      5054
Val Thr Ala Pro Ala Asn Ile Ser Asn Ser Thr Trp Ser Ser Ala Leu
1645                1650                1655

CAT CAG ACT CTA AGC AAC ATG GTA TCA CAG GCA CAG AGT CAT CAT GAA      5102
His Gln Thr Leu Ser Asn Met Val Ser Gln Ala Gln Ser His His Glu
1660                1665                1670                1675

GCA CCC AAG AGT CAA GAA GAT ACC ATT TGT ACC ATG TTT TAC TAT CCT      5150
Ala Pro Lys Ser Gln Glu Asp Thr Ile Cys Thr Met Phe Tyr Tyr Pro
            1680                1685                1690

CAG AAA ATT CCC AAT AAA CCA GAG TTT GAG GAC AGT AAT CCT TCC CCT      5198
Gln Lys Ile Pro Asn Lys Pro Glu Phe Glu Asp Ser Asn Pro Ser Pro
        1695                1700                1705

CTA CCA CCG GAT ATG GCT CCT GGG CAG AGT TAT CAA CCC CAA TCA GAA      5246
Leu Pro Pro Asp Met Ala Pro Gly Gln Ser Tyr Gln Pro Gln Ser Glu
    1710                1715                1720

TCT GCT TCC TCT AGT TCG ATG GAT AAG TAT CAT ATA CAT CAC ATT TCT      5294
Ser Ala Ser Ser Ser Ser Met Asp Lys Tyr His Ile His His Ile Ser
1725                1730                1735

GAA CCA ACT AGA CAA GAA AAC TGG ACA CCT TTG AAA AAT GAC TTG GAA      5342
Glu Pro Thr Arg Gln Glu Asn Trp Thr Pro Leu Lys Asn Asp Leu Glu
1740                1745                1750                1755

AAT CAC CTT GAA GAC TTT GAA CTG GAA GTA GAA CTC CTC ATT ACC CTA      5390
Asn His Leu Glu Asp Phe Glu Leu Glu Val Glu Leu Leu Ile Thr Leu
            1760                1765                1770

ATT AAA TCA GAA AAA GCA AGC CTG GGT TTT ACA GTA ACC AAA GGC AAT      5438
Ile Lys Ser Glu Lys Ala Ser Leu Gly Phe Thr Val Thr Lys Gly Asn
        1775                1780                1785

CAG AGA ATT GGT TGT TAT GTT CAT GAT GTC ATA CAG GAT CCA GCC AAA      5486
Gln Arg Ile Gly Cys Tyr Val His Asp Val Ile Gln Asp Pro Ala Lys
    1790                1795                1800

AGT GAT GGA AGG CTA AAA CCT GGG GAC CGG CTC ATA AAG GTT AAT GAT      5534
Ser Asp Gly Arg Leu Lys Pro Gly Asp Arg Leu Ile Lys Val Asn Asp
1805                1810                1815
```

```
ACA GAT GTT ACT AAT ATG ACT CAT ACA GAT GCA GTT AAT CTG CTC CGG      5582
Thr Asp Val Thr Asn Met Thr His Thr Asp Ala Val Asn Leu Leu Arg
1820                    1825                    1830                1835

GCT GCA TCC AAA ACA GTC AGA TTA GTT ATT GGA CGA GTT CCT AGA ATT      5630
Ala Ala Ser Lys Thr Val Arg Leu Val Ile Gly Arg Val Pro Arg Ile
            1840                    1845                    1850

ACC CAG AAT ACC AAT GTT GCC TCA TTT GCT ACC GGA CAT AAA CTA ACG      5678
Thr Gln Asn Thr Asn Val Ala Ser Phe Ala Thr Gly His Lys Leu Thr
                1855                    1860                    1865

TGC AAC AAA GAG GAG TTG GGT TTT TCC TTA TGT GGA GGT CAT GAC AGC      5726
Cys Asn Lys Glu Glu Leu Gly Phe Ser Leu Cys Gly Gly His Asp Ser
        1870                    1875                    1880

CTT TAT CAA GTG GTA TAT ATT AGT GAT ATT AAT CCA AGG TCC GTC GCA      5774
Leu Tyr Gln Val Val Tyr Ile Ser Asp Ile Asn Pro Arg Ser Val Ala
            1885                    1890                    1895

GCC ATT GAG GGT AAT CTC CAG CTA TTA GAT GTC ATC CAT TAT GTG AAC      5822
Ala Ile Glu Gly Asn Leu Gln Leu Leu Asp Val Ile His Tyr Val Asn
1900                    1905                    1910                1915

GGA GTC AGC ACA CAA GGA ATG ACC TTG GAG GAA GTT AAC AGA GCA TTA      5870
Gly Val Ser Thr Gln Gly Met Thr Leu Glu Glu Val Asn Arg Ala Leu
            1920                    1925                    1930

GAC ATG TCA CTT CCT TCA TTG GTA TTG AAA GCA ACA AGA AAT GAT CTT      5918
Asp Met Ser Leu Pro Ser Leu Val Leu Lys Ala Thr Arg Asn Asp Leu
                1935                    1940                    1945

CCA GTG GTT CCC AGC TCA AAG AGG TCT GCT GTT TCA GCT CCA AAG TCA      5966
Pro Val Val Pro Ser Ser Lys Arg Ser Ala Val Ser Ala Pro Lys Ser
        1950                    1955                    1960

ACC AAA GGC AAT GGT TCC TAC AGT GTG GGG TCT TGC AGC CAG CCT GCC      6014
Thr Lys Gly Asn Gly Ser Tyr Ser Val Gly Ser Cys Ser Gln Pro Ala
1965                    1970                    1975

CTC ACT CCT AAT GAT TCA TTC TCC ACG GTT GCT GGG GAA GAA ATA AAT      6062
Leu Thr Pro Asn Asp Ser Phe Ser Thr Val Ala Gly Glu Glu Ile Asn
1980                    1985                    1990                1995

GAA ATA TCG TAC CCC AAA GGA AAA TGT TCT ACT TAT CAG ATA AAG GGA      6110
Glu Ile Ser Tyr Pro Lys Gly Lys Cys Ser Thr Tyr Gln Ile Lys Gly
            2000                    2005                    2010

TCA CCA AAC TTG ACT CTG CCC AAA GAA TCT TAT ATA CAA GAA GAT GAC      6158
Ser Pro Asn Leu Thr Leu Pro Lys Glu Ser Tyr Ile Gln Glu Asp Asp
        2015                    2020                    2025

ATT TAT GAT GAT TCC CAA GAA GCT GAA GTT ATC CAG TCT CTG CTG GAT      6206
Ile Tyr Asp Asp Ser Gln Glu Ala Glu Val Ile Gln Ser Leu Leu Asp
            2030                    2035                    2040

GTT GTT GAT GAG GAA GCC CAG AAT CTT TTA AAC GAA AAT AAT GCA GCA      6254
Val Val Asp Glu Glu Ala Gln Asn Leu Leu Asn Glu Asn Asn Ala Ala
            2045                    2050                    2055

GGA GAC TCC TGT GGT CCA GGT ACA TTA AAG ATG AAT GGG AAG TTA TCA      6302
Gly Asp Ser Cys Gly Pro Gly Thr Leu Lys Met Asn Gly Lys Leu Ser
2060                    2065                    2070                2075

GAA GAG AGA ACA GAA GAT ACA GAC TGC GAT GGT TCA CCT TTA CCT GAG      6350
Glu Glu Arg Thr Glu Asp Thr Asp Cys Asp Gly Ser Pro Leu Pro Glu
            2080                    2085                    2090

TAT TTT ACT GAG GCC ACC AAA ATG AAT GGC TGT GAA GAA TAT TGT GAA      6398
Tyr Phe Thr Glu Ala Thr Lys Met Asn Gly Cys Glu Glu Tyr Cys Glu
                2095                    2100                    2105

GAA AAA GTA AAA AGT GAA AGC TTA ATT CAG AAG CCA CAA GAA AAG AAG      6446
Glu Lys Val Lys Ser Glu Ser Leu Ile Gln Lys Pro Gln Glu Lys Lys
        2110                    2115                    2120
```

```
ACT GAT GAT GAT GAA ATA ACA TGG GGA AAT GAT GAG TTG CCA ATA GAG      6494
Thr Asp Asp Asp Glu Ile Thr Trp Gly Asn Asp Glu Leu Pro Ile Glu
    2125                2130                2135

AGA ACA AAC CAT GAA GAT TCT GAT AAA GAT CAT TCC TTT CTG ACA AAC      6542
Arg Thr Asn His Glu Asp Ser Asp Lys Asp His Ser Phe Leu Thr Asn
2140                2145                2150                2155

GAT GAG CTC GCT GTA CTC CCT GTC GTC AAA GTG CTT CCC TCT GGT AAA      6590
Asp Glu Leu Ala Val Leu Pro Val Val Lys Val Leu Pro Ser Gly Lys
                2160                2165                2170

TAC ACG GGT GCC AAC TTA AAA TCA GTC ATT CGA GTC CTG CGG GGT TTG      6638
Tyr Thr Gly Ala Asn Leu Lys Ser Val Ile Arg Val Leu Arg Gly Leu
            2175                2180                2185

CTA GAT CAA GGA ATT CCT TCT AAG GAG CTG GAG AAT CTT CAA GAA TTA      6686
Leu Asp Gln Gly Ile Pro Ser Lys Glu Leu Glu Asn Leu Gln Glu Leu
        2190                2195                2200

AAA CCT TTG GAT CAG TGT CTA ATT GGG CAA ACT AAG GAA AAC AGA AGG      6734
Lys Pro Leu Asp Gln Cys Leu Ile Gly Gln Thr Lys Glu Asn Arg Arg
    2205                2210                2215

AAG AAC AGA TAT AAA AAT ATA CTT CCC TAT GAT GCT ACA AGA GTG CCT      6782
Lys Asn Arg Tyr Lys Asn Ile Leu Pro Tyr Asp Ala Thr Arg Val Pro
2220                2225                2230                2235

CTT GGA GAT GAA GGT GGC TAT ATC AAT GCC AGC TTC ATT AAG ATA CCA      6830
Leu Gly Asp Glu Gly Gly Tyr Ile Asn Ala Ser Phe Ile Lys Ile Pro
                2240                2245                2250

GTT GGG AAA GAA GAG TTC GTT TAC ATT GCC TGC CAA GGA CCA CTG CCT      6878
Val Gly Lys Glu Glu Phe Val Tyr Ile Ala Cys Gln Gly Pro Leu Pro
            2255                2260                2265

ACA ACT GTT GGA GAC TTC TGG CAG ATG ATT TGG GAG CAA AAA TCC ACA      6926
Thr Thr Val Gly Asp Phe Trp Gln Met Ile Trp Glu Gln Lys Ser Thr
        2270                2275                2280

GTG ATA GCC ATG ATG ACT CAA GAA GTA GAA GGA GAA AAA ATC AAA TGC      6974
Val Ile Ala Met Met Thr Gln Glu Val Glu Gly Glu Lys Ile Lys Cys
    2285                2290                2295

CAG CGC TAT TGG CCC AAC ATC CTA GGC AAA ACA ACA ATG GTC AGC AAC      7022
Gln Arg Tyr Trp Pro Asn Ile Leu Gly Lys Thr Thr Met Val Ser Asn
2300                2305                2310                2315

AGA CTT CGA CTG GCT CTT GTG AGA ATG CAG CAG CTG AAG GGC TTT GTG      7070
Arg Leu Arg Leu Ala Leu Val Arg Met Gln Gln Leu Lys Gly Phe Val
                2320                2325                2330

GTG AGG GCA ATG ACC CTT GAA GAT ATT CAG ACC AGA GAG GTG CGC CAT      7118
Val Arg Ala Met Thr Leu Glu Asp Ile Gln Thr Arg Glu Val Arg His
            2335                2340                2345

ATT TCT CAT CTG AAT TTC ACT GCC TGG CCA GAC CAT GAT ACA CCT TCT      7166
Ile Ser His Leu Asn Phe Thr Ala Trp Pro Asp His Asp Thr Pro Ser
        2350                2355                2360

CAA CCA GAT GAT CTG CTT ACT TTT ATC TCC TAC ATG AGA CAC ATC CAC      7214
Gln Pro Asp Asp Leu Leu Thr Phe Ile Ser Tyr Met Arg His Ile His
    2365                2370                2375

AGA TCA GGC CCA ATC ATT ACG CAC TGC AGT GCT GGC ATT GGA CGT TCA      7262
Arg Ser Gly Pro Ile Ile Thr His Cys Ser Ala Gly Ile Gly Arg Ser
2380                2385                2390                2395

GGG ACC CTG ATT TGC ATA GAT GTG GTT CTG GGA TTA ATC AGT CAG GAT      7310
Gly Thr Leu Ile Cys Ile Asp Val Val Leu Gly Leu Ile Ser Gln Asp
                2400                2405                2410

CTT GAT TTT GAC ATC TCT GAT TTG GTG CGC TGC ATG AGA CTA CAA AGA      7358
Leu Asp Phe Asp Ile Ser Asp Leu Val Arg Cys Met Arg Leu Gln Arg
            2415                2420                2425
```

```
CAC GGA ATG GTT CAG ACA GAG GAT CAA TAT ATT TTC TGC TAT CAA GTC         7406
His Gly Met Val Gln Thr Glu Asp Gln Tyr Ile Phe Cys Tyr Gln Val
            2430                2435                2440

ATC CTT TAT GTC CTG ACA CGT CTT CAA GCA GAA GAA GAG CAA AAA CAG         7454
Ile Leu Tyr Val Leu Thr Arg Leu Gln Ala Glu Glu Glu Gln Lys Gln
            2445                2450                2455

CAG CCT CAG CTT CTG AAG TGACATGAAA AGAGCCTCTG GATGCATTTC                7502
Gln Pro Gln Leu Leu Lys
2460            2465

CATTTCTCTC CTTAACCTCC AGCAGACTCC TGCTCTCTAT CCAAATAAAG ATCACAGAGC       7562

AGNAAGTTCA TACAACATGC ATGTTCTCCT CTATCTTAGA GGGGTATTCT TCTTGAAAAT       7622

AAAAAATATT GAAATGCTGT ATTTTTACAG CTACTTTAAC CTATGATAAT TATTTACAAA       7682

ATTTTAACAC TAACCAAACA ATGCAGATCT TAGGGATGAT TAAAGGCAGC ATTGATGATA       7742

GCAAGACATT GTTACAAGGA CATGGTGAGT CTATTTTTAA TGCACCAATC TTGTTTATAG       7802

CAAAAATGTT TTCCAATATT TTAATAAAGT AGTTATTTTA TAGGGCATAC TTGAAACCAG       7862

TATTTAAGCT TTAAATGACA GTAATATTGG CATAGAAAAA AGTAGCAAAT GTTTACTGTA       7922

TCAATTTCTA ATGTTTACTA TATAGAATTT CCTGTAATAT ATTTATATAC TTTTTCATGA       7982

AAATGGAGTT ATCAGTTATC TGTTTGTTAC TGCATCATCT GTTTGTAATC ATTATCTC        8040

(2) INFORMATION FOR SEQ ID NO:2:

(i) SEQUENCE CHARACTERISTICS:
        (A) LENGTH: 3090 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: HOMO SAPIENS (ix) FEATURE:
        (A) NAME/KEY: CDS
        (B) LOCATION: 1311..2420

(xi) SEQUENCE DESCRIPTION: SEQ ID NO:2:

GAATTCCGGA TTTACCTCAG TCTGTATCCC TTGAATAGCT CACAATAATC GACACATGCA         60

GCTGGGGACT GTGGGTGGGA TACTTAGGTG TGGGACACCA TATCTTCCAG CAGTAATAAA        120

GAAGTCAGGT GGGAATATGT AACATCTTGA GTGCTCATCC AGGTAGGTAC TAAGGTATGA        180

TCAACTCTAT GGAAGATCGA TTAGGAAACT CCCTGAAAGA GAGTTCAGCC TGAAGAGAGA        240

ACCAAAGGCC AACATCTTGG AGCTGGCTAC AGGACAGTAG GATGTAAGCT CGAGGGGAGG        300

AGAGGGTTAG GCGCAGTGGC TCACGCCTGT AGTCCCAACC ATTTGGGAGG CTGAGGCAGG        360

CAGATCGCTT GAGCCCGGGG GTTCAAGACC AGCCTGGGCA ACATGGCGAA ACCCCATCTC        420

TACAAAAAAA TACAAAAAAA ATGTAGCTGC GTGTGGTGGC ATGCACCTGT AGTCACAGCC        480

ACCACAGAGG TTGAGGTGGG AGGACTGCTT GAGCCTGGGA GGTGGAGGCT GCAGCGAACC        540

GAGATTGTGC CACTGCACTC CAGGATGGGC GACAGAGTGA GACCCGGACA GAGTGAGACC        600

CTGTCTCATT CATTCATTCA TAAATAAGAA GAGGGGAAA ACGGGTGCCC AGATTGCTCT        660

CAGGCTCCTC CTCCCTTTCA GCTGGTACTT AACCACTCTT AACTTCAGCC TGCTCATGAA        720
```

```
TGAAATGGGA ATGACAATTC CTAACTCAGG CAGTTTTTGC AAAGACCAGA GAAAATCATG    780

TATTAATACT AGTACCCAGC ACCATTCCAA ACATACAATA CAAATGCCCC ATAAATGACA    840

GCCAAGGTAA CTGTTCTTTG CTTCCTCTCT TAGGAGACGT GTGAGGTTCT CTGTTGCTCC    900

TTTTGACTCC CAACTCCTGC TACAATGACT GATTTGACAC TGATTACCTC ACAGTACACA    960

CTGGGTGCTG GCCAACTGCA GCATGCTACG TATCCCACAC CCCCTCCCTG AGTGGTGGGA   1020

CATTAATGGT GGGATGGTAG AATGTGCAGT CCGGTCTTGT ACATTGAGTG TTAAACCTAC   1080

AATGTTTTGG ATGATAGAAG GGACATTCCA TCTTCTTACA AGCAGGGAAG TAACGGCAGA   1140

GCTGACTACT GGAAGGTGGT GCTGGTGGTG CAACAGGTTC TGGAGTTAAA ACCAATGGAA   1200

AAGAAAGATT TCAGCTTTCC TTAAGACAAG ACAAAGAGAA AAACCAGGAG ATCCACCTAT   1260

CGCCCATCAC ATTACAGCCA GCACTGTCCG AGGCAAAGAC AGTCCACAGC ATG GTC      1316
                                                        Met Val
                                                          1

CAA CCT GAG CAG GCC CCA AAG GTA CTG AAT GTT GTC GTG GAC CCT CAA     1364
Gln Pro Glu Gln Ala Pro Lys Val Leu Asn Val Val Val Asp Pro Gln
          5                  10                  15

GGC CGA GGT GCT CCT GAG ATC AAA GCT ACC ACC GCT ACC TCT GTT TGC     1412
Gly Arg Gly Ala Pro Glu Ile Lys Ala Thr Thr Ala Thr Ser Val Cys
 20                  25                  30

CCT TCT CCT TTC AAA ATG AAG CCC ATA GGA CTT CAA GAG AGA AGA GGG     1460
Pro Ser Pro Phe Lys Met Lys Pro Ile Gly Leu Gln Glu Arg Arg Gly
 35                  40                  45                  50

TCC AAC GTA TCT CTT ACA TTG GAC ATG AGT AGC TTG GGG AAC ATT GAA     1508
Ser Asn Val Ser Leu Thr Leu Asp Met Ser Ser Leu Gly Asn Ile Glu
                 55                  60                  65

CCC TTT GTG TCT ATA CCA ACA CCA CGG GAG AAG GTA GCA ATG GAG TAT     1556
Pro Phe Val Ser Ile Pro Thr Pro Arg Glu Lys Val Ala Met Glu Tyr
             70                  75                  80

CTG CAG TCA GCC AGC CGA ATT CTC GAC AAG GTT CAG CTG AGG GAC GTC     1604
Leu Gln Ser Ala Ser Arg Ile Leu Asp Lys Val Gln Leu Arg Asp Val
         85                  90                  95

GTG GCA AGT TCA CAT TTA CTC CAA AGT GAA TTC ATG GAA ATA CCA ATG     1652
Val Ala Ser Ser His Leu Leu Gln Ser Glu Phe Met Glu Ile Pro Met
100                 105                 110

AAC TTT GTG GAT CCC AAA GAA ATT GAT ATT CCG CGT CAT GGA ACT AAA     1700
Asn Phe Val Asp Pro Lys Glu Ile Asp Ile Pro Arg His Gly Thr Lys
115                 120                 125                 130

AAT CGC TAT AAG ACC ATT TTA CCA AAT CCC CTC AGC AGA GTG TGT TTA     1748
Asn Arg Tyr Lys Thr Ile Leu Pro Asn Pro Leu Ser Arg Val Cys Leu
                135                 140                 145

AGA CCA AAA AAT GTA ACC GAT TCA TTG AGC ACC TAC ATT AAT GCT AAT     1796
Arg Pro Lys Asn Val Thr Asp Ser Leu Ser Thr Tyr Ile Asn Ala Asn
            150                 155                 160

TAT ATT AGG GGC TAC AGT GGC AAG GAG AAA GCC TTC ATT GCC ACG CAG     1844
Tyr Ile Arg Gly Tyr Ser Gly Lys Glu Lys Ala Phe Ile Ala Thr Gln
        165                 170                 175

GGC CCC ATG ATC AAC ACC GTG GAT GAT TTC TGG CAG ATG GTT TGG CAG     1892
Gly Pro Met Ile Asn Thr Val Asp Asp Phe Trp Gln Met Val Trp Gln
180                 185                 190

GAA GAC AGC CCT GTG ATT GTT ATG ATC ACA AAA CTC AAA GAA AAA AAT     1940
Glu Asp Ser Pro Val Ile Val Met Ile Thr Lys Leu Lys Glu Lys Asn
195                 200                 205                 210

GAG AAA TGT GTG CTA TAC TGG CCG GAA AAG AGA GGG ATA TAT GGA AAA     1988
Glu Lys Cys Val Leu Tyr Trp Pro Glu Lys Arg Gly Ile Tyr Gly Lys
                215                 220                 225
```

```
GTT GAG GTT CTG GTT ATC AGT GTA AAT GAA TGT GAT AAC TAC ACC ATT       2036
Val Glu Val Leu Val Ile Ser Val Asn Glu Cys Asp Asn Tyr Thr Ile
            230                 235                 240

CGA AAC CTT GTC TTA AAG CAA GGA AGC CAC ACC CAA CAT GTG AGC AAT       2084
Arg Asn Leu Val Leu Lys Gln Gly Ser His Thr Gln His Val Ser Asn
        245                 250                 255

TAC TGG TAC ACC TCA TGG CCT GAT CAC AAG ACT CCA GAC AGT GCC CAG       2132
Tyr Trp Tyr Thr Ser Trp Pro Asp His Lys Thr Pro Asp Ser Ala Gln
    260                 265                 270

CCC CTC CTA CAG CTC ATG CTG GAT GTA GAA GAA GAC AGA CTT GCT TCC       2180
Pro Leu Leu Gln Leu Met Leu Asp Val Glu Glu Asp Arg Leu Ala Ser
275                 280                 285                 290

CAG GGG CCG AGG GCT GTG GTT GTC CAC TGC AGT GCA GGA ATA GGT AGA       2228
Gln Gly Pro Arg Ala Val Val Val His Cys Ser Ala Gly Ile Gly Arg
                295                 300                 305

ACA GGG TGT TTT ATT GCT ACA TCC ATT GGC TGT CAA CAG CTG AAA GAA       2276
Thr Gly Cys Phe Ile Ala Thr Ser Ile Gly Cys Gln Gln Leu Lys Glu
            310                 315                 320

GAA GGA GTT GTG GAT GCA CTA AGC ATT GTC TGC CAG CTT CGT ATG GAT       2324
Glu Gly Val Val Asp Ala Leu Ser Ile Val Cys Gln Leu Arg Met Asp
        325                 330                 335

AGA GGT GGA ATG GTG CAA ACC AGT GAG CAG TAT GAA TTT GTG CAC CAT       2372
Arg Gly Gly Met Val Gln Thr Ser Glu Gln Tyr Glu Phe Val His His
    340                 345                 350

GCT CTG TGC CTG TAT GAG AGC AGA CTT TCA GCA GAG ACT GTC CAG TGAGTCAT 2427
Ala Leu Cys Leu Tyr Glu Ser Arg Leu Ser Ala Glu Thr Val Gln
355                 360                 365                 370

AAGACTTGTC AGACCATCAA TCTCTTGGGG TGATTAACAA ATTACCCACC CAAGGCTTCA    2487

TGAAGGAGCT TCCTGCAATG GAAGGAAGGA GAAGCTCTGA AGCCCATGTA TGGCATGGAT    2547

TGTGGAAGAC TGGGCAACAT ATTTAAGATT CCAGCTCCT TGTGTATATG AATGCATTTG     2607

TAAGCATCCC CCAAATTATT CTGAAGGTTT TTTGATGATG GAGGTATGAT AGGTTTATCA    2667

CACAGCCTAA GGCAGATTTT GTTTTGTCTG TACTGACTCT ATCTGCCACA CAGAATGTAT    2727

GTATGTAATA TTCAGTAATA AATGTCATCA GGTGATGACT GGATGAGCTG CTGAAGACAT    2787

TCGTATTATG TGTTAGATGC TTTAATGTTT GCAAAATCTG TCTTGTGAAT GGACTGTCAG    2847

CTGTTAAACT GTTCCTGTTT TGAAGTGCTA TTACCTTTCT CAGTTACCAG AATCTTGCTG    2907

CTAAAGTTGC AAGTGATTGA TAATGGATTT TTAACAGAGA AGTCTTTGTT TTTGAAAAAC    2967

AAAAATCAAA AACAGTAACT ATTTTATATG GAAATGTGTC TTGATAATAT TACCTATTAA    3027

ATGTGTATTT ATAGTCCCTC CTATCAAACA ATTACAGAGC ACAATGATTG TCATCCGGAA    3087

TTC                                                                  3090
```

(2) INFORMATION FOR SEQ ID NO:3:

(i) SEQUENCE CHARACTERISTICS:
        (A) LENGTH: 2465 amino acids
        (B) TYPE: amino acid
        (D) TOPOLOGY: linear (ii) MOLECULE TYPE: protein (xi) SEQUENCE DESCRIPTION: SEQ ID NO:3:

```
Met His Val Ser Leu Ala Glu Ala Leu Glu Val Arg Gly Gly Pro Leu
 1               5                  10                  15

Gln Glu Glu Glu Ile Trp Ala Val Leu Asn Gln Ser Ala Glu Ser Leu
            20                  25                  30
```

```
Gln Glu Leu Phe Arg Lys Val Ser Leu Ala Asp Pro Ala Ala Leu Gly
         35                  40                  45

Phe Ile Ile Ser Pro Trp Ser Leu Leu Leu Pro Ser Gly Ser Val
 50                  55                  60

Ser Phe Thr Asp Glu Asn Ile Ser Asn Gln Asp Leu Arg Ala Phe Thr
 65                  70                  75                  80

Ala Pro Glu Val Leu Gln Asn Gln Ser Leu Thr Ser Leu Ser Asp Val
                 85                  90                  95

Glu Lys Ile His Ile Tyr Ser Leu Gly Met Thr Leu Tyr Trp Gly Ala
                100                 105                 110

Asp Tyr Glu Val Pro Gln Ser Gln Pro Ile Lys Leu Gly Asp His Leu
            115                 120                 125

Asn Ser Ile Leu Leu Gly Met Cys Glu Asp Val Ile Tyr Ala Arg Val
        130                 135                 140

Ser Val Arg Thr Val Leu Asp Ala Cys Ser Ala His Ile Arg Asn Ser
145                 150                 155                 160

Asn Cys Ala Pro Ser Phe Ser Tyr Val Lys His Leu Val Lys Leu Val
                165                 170                 175

Leu Gly Asn Leu Ser Gly Thr Asp Gln Leu Ser Cys Asn Ser Glu Gln
            180                 185                 190

Lys Pro Asp Arg Ser Gln Ala Ile Arg Asp Arg Leu Arg Gly Lys Gly
        195                 200                 205

Leu Pro Thr Gly Arg Ser Ser Thr Ser Asp Val Leu Asp Ile Gln Lys
210                 215                 220

Pro Pro Leu Ser His Gln Thr Phe Leu Asn Lys Gly Leu Ser Lys Ser
225                 230                 235                 240

Met Gly Phe Leu Ser Ile Lys Asp Thr Gln Asp Glu Asn Tyr Phe Lys
                245                 250                 255

Asp Ile Leu Ser Asp Asn Ser Gly Arg Glu Asp Ser Glu Asn Thr Phe
            260                 265                 270

Cys Pro Tyr Gln Phe Lys Thr Ser Gly Pro Glu Lys Lys Pro Ile Pro
        275                 280                 285

Gly Ile Asp Val Leu Ser Lys Lys Ile Trp Ala Ser Ser Met Asp
290                 295                 300

Leu Leu Cys Thr Ala Asp Arg Asp Phe Ser Ser Gly Glu Thr Ala Thr
305                 310                 315                 320

Tyr Arg Arg Cys His Pro Glu Ala Val Thr Val Arg Thr Ser Thr Thr
                325                 330                 335

Pro Arg Lys Lys Glu Ala Arg Tyr Ser Asp Gly Ser Ile Ala Leu Asp
            340                 345                 350

Ile Phe Gly Pro Gln Lys Met Asp Pro Ile Tyr His Thr Arg Glu Leu
        355                 360                 365

Pro Thr Ser Ser Ala Ile Ser Ser Ala Leu Asp Arg Ile Arg Glu Arg
370                 375                 380

Gln Lys Lys Leu Gln Val Leu Arg Glu Ala Met Asn Val Glu Glu Pro
385                 390                 395                 400

Val Arg Arg Tyr Lys Thr Tyr His Gly Asp Val Phe Ser Thr Ser Ser
                405                 410                 415

Glu Ser Pro Ser Ile Ile Ser Glu Ser Asp Phe Arg Gln Val Arg
            420                 425                 430

Arg Ser Glu Ala Ser Lys Arg Phe Glu Ser Ser Gly Leu Pro Gly
        435                 440                 445
```

-continued

```
Val Asp Glu Thr Leu Ser Gln Gly Gln Ser Gln Arg Pro Ser Arg Gln
    450                 455                 460

Tyr Glu Thr Pro Phe Glu Gly Asn Leu Ile Asn Gln Glu Ile Met Leu
465                 470                 475                 480

Lys Arg Gln Glu Glu Leu Met Gln Leu Gln Ala Lys Met Ala Leu
                485                 490                 495

Arg Gln Ser Arg Leu Ser Leu Tyr Pro Gly Asp Thr Ile Lys Ala Ser
            500                 505                 510

Met Leu Asp Ile Thr Arg Asp Pro Leu Arg Glu Ile Ala Leu Glu Thr
        515                 520                 525

Ala Met Thr Gln Arg Lys Leu Arg Asn Phe Phe Gly Pro Glu Phe Val
    530                 535                 540

Lys Met Thr Ile Glu Pro Phe Ile Ser Leu Asp Leu Pro Arg Ser Ile
545                 550                 555                 560

Leu Thr Lys Lys Gly Lys Asn Glu Asp Asn Arg Arg Lys Val Asn Ile
                565                 570                 575

Met Leu Leu Asn Gly Gln Arg Leu Glu Leu Thr Cys Asp Thr Lys Thr
            580                 585                 590

Ile Cys Lys Asp Val Phe Asp Met Val Ala His Ile Gly Leu Val
        595                 600                 605

Glu His His Leu Phe Ala Leu Ala Thr Leu Lys Asp Asn Glu Tyr Phe
    610                 615                 620

Phe Val Asp Pro Asp Leu Lys Leu Thr Lys Val Ala Pro Glu Gly Trp
625                 630                 635                 640

Lys Glu Glu Pro Lys Lys Lys Thr Lys Ala Thr Val Asn Phe Thr Leu
                645                 650                 655

Phe Phe Arg Ile Lys Phe Phe Met Asp Asp Val Ser Leu Ile Gln His
            660                 665                 670

Thr Leu Thr Cys His Gln Tyr Tyr Leu Gln Leu Arg Lys Asp Ile Leu
        675                 680                 685

Glu Glu Arg Met His Cys Asp Asp Glu Thr Ser Leu Leu Leu Ala Ser
    690                 695                 700

Leu Ala Leu Gln Ala Glu Tyr Gly Asp Tyr Gln Pro Glu Val His Gly
705                 710                 715                 720

Val Ser Tyr Phe Arg Met Glu His Tyr Leu Pro Ala Arg Val Met Glu
                725                 730                 735

Lys Leu Asp Leu Ser Tyr Ile Lys Glu Glu Leu Pro Lys Leu His Asn
            740                 745                 750

Thr Tyr Val Gly Ala Ser Glu Lys Glu Thr Glu Leu Glu Phe Leu Lys
        755                 760                 765

Val Cys Gln Arg Leu Thr Glu Tyr Gly Val His Phe His Arg Val His
    770                 775                 780

Pro Glu Lys Lys Ser Gln Thr Gly Ile Leu Leu Gly Val Cys Ser Lys
785                 790                 795                 800

Gly Val Leu Val Phe Glu Val His Asn Gly Val Arg Thr Leu Val Leu
                805                 810                 815

Arg Phe Pro Trp Arg Glu Thr Lys Lys Ile Ser Phe Ser Lys Lys Lys
            820                 825                 830

Ile Thr Leu Gln Asn Thr Ser Asp Gly Ile Lys His Gly Phe Gln Thr
        835                 840                 845

Asp Asn Ser Lys Ile Cys Gln Tyr Leu Leu His Leu Cys Ser Tyr Gln
    850                 855                 860
```

```
His Lys Phe Gln Leu Gln Met Arg Ala Arg Gln Ser Asn Gln Asp Ala
865                 870                 875                 880

Gln Asp Ile Glu Arg Ala Ser Phe Arg Ser Leu Asn Leu Gln Ala Glu
            885                 890                 895

Ser Val Arg Gly Phe Asn Met Gly Arg Ala Ile Ser Thr Gly Ser Leu
        900                 905                 910

Ala Ser Ser Thr Leu Asn Lys Leu Ala Val Arg Pro Leu Ser Val Gln
            915                 920                 925

Ala Glu Ile Leu Lys Arg Leu Ser Cys Ser Glu Leu Ser Leu Tyr Gln
930                 935                 940

Pro Leu Gln Asn Ser Ser Lys Glu Lys Asn Asp Lys Ala Ser Trp Glu
945                 950                 955                 960

Glu Lys Pro Arg Glu Met Ser Lys Ser Tyr His Asp Leu Ser Gln Ala
            965                 970                 975

Ser Leu Tyr Pro His Arg Lys Asn Val Ile Val Asn Met Glu Pro Pro
        980                 985                 990

Pro Gln Thr Val Ala Glu Leu Val Gly Lys Pro Ser His Gln Met Ser
            995                 1000                1005

Arg Ser Asp Ala Glu Ser Leu Ala Gly Val Thr Lys Leu Asn Asn Ser
        1010                1015                1020

Lys Ser Val Ala Ser Leu Asn Arg Ser Pro Glu Arg Arg Lys His Glu
1025                1030                1035                1040

Ser Asp Ser Ser Ser Ile Glu Asp Pro Gly Gln Ala Tyr Val Leu Asp
                1045                1050                1055

Val Leu His Lys Arg Trp Ser Ile Val Ser Ser Pro Glu Arg Glu Ile
            1060                1065                1070

Thr Leu Val Asn Leu Lys Lys Asp Ala Lys Tyr Gly Leu Gly Phe Gln
        1075                1080                1085

Ile Ile Gly Gly Glu Lys Met Glu Thr Asp Leu Gly Ile Phe Ile Ser
    1090                1095                1100

Ser Val Ala Pro Gly Gly Pro Ala Asp Phe His Gly Cys Leu Lys Pro
1105                1110                1115                1120

Gly Asp Arg Leu Ile Ser Val Asn Ser Val Ser Leu Glu Gly Val Ser
            1125                1130                1135

His His Ala Ala Ile Glu Ile Leu Gln Asn Ala Pro Glu Asp Val Thr
        1140                1145                1150

Leu Val Ile Ser Gln Pro Lys Glu Lys Ile Ser Lys Val Pro Ser Thr
            1155                1160                1165

Pro Val His Leu Thr Asn Glu Met Lys Asn Tyr Met Lys Lys Ser Ser
        1170                1175                1180

Tyr Met Gln Asp Ser Ala Ile Asp Ser Ser Lys Asp His His Trp
1185                1190                1195                1200

Ser Arg Gly Thr Leu Arg His Ile Ser Glu Asn Ser Phe Gly Pro Ser
            1205                1210                1215

Gly Gly Leu Arg Glu Gly Ser Leu Ser Ser Gln Asp Ser Arg Thr Glu
        1220                1225                1230

Ser Ala Ser Leu Ser Gln Ser Gln Val Asn Gly Phe Phe Ala Ser His
    1235                1240                1245

Leu Gly Asp Gln Thr Trp Gln Glu Ser Gln His Gly Ser Pro Ser Pro
    1250                1255                1260

Ser Val Ile Ser Lys Ala Thr Glu Lys Glu Thr Phe Thr Asp Ser Asn
1265                1270                1275                1280
```

-continued

```
Gln Ser Lys Thr Lys Lys Pro Gly Ile Ser Asp Val Thr Asp Tyr Ser
            1285                1290                1295

Asp Arg Gly Asp Ser Asp Met Asp Glu Ala Thr Tyr Ser Ser Ser Gln
        1300                1305                1310

Asp His Gln Thr Pro Lys Gln Glu Ser Ser Ser Val Asn Thr Ser
    1315                1320                1325

Asn Lys Met Asn Phe Lys Thr Phe Ser Ser Pro Pro Lys Pro Gly
1330                1335                1340

Asp Ile Phe Glu Val Glu Leu Ala Lys Asn Asp Asn Ser Leu Gly Ile
1345                1350                1355                1360

Ser Val Thr Gly Gly Val Asn Thr Ser Val Arg His Gly Gly Ile Tyr
            1365                1370                1375

Val Lys Asp Val Ile Pro Gln Gly Ala Ala Glu Ser Asp Gly Arg Ile
        1380                1385                1390

His Lys Gly Asp Arg Val Leu Ala Val Asn Gly Val Ser Leu Glu Gly
    1395                1400                1405

Ala Thr His Lys Gln Ala Val Glu Thr Leu Arg Asn Thr Gly Gln Val
    1410                1415                1420

Val His Leu Leu Leu Glu Lys Gly Gln Ser Pro Thr Ser Lys Glu His
1425                1430                1435                1440

Val Pro Val Thr Pro Gln Cys Thr Leu Ser Asp Gln Asn Ala Gln Gly
            1445                1450                1455

Gln Gly Pro Glu Lys Val Lys Lys Thr Thr Gln Val Lys Asp Tyr Ser
        1460                1465                1470

Phe Val Thr Glu Glu Asn Thr Phe Glu Val Lys Leu Phe Lys Asn Ser
    1475                1480                1485

Ser Gly Leu Gly Phe Ser Phe Ser Arg Glu Asp Asn Leu Ile Pro Glu
    1490                1495                1500

Gln Ile Asn Ala Ser Ile Val Arg Val Lys Lys Leu Phe Ala Gly Gln
1505                1510                1515                1520

Pro Ala Ala Glu Ser Gly Lys Ile Asp Val Gly Asp Val Ile Leu Lys
            1525                1530                1535

Val Asn Gly Ala Ser Leu Lys Gly Leu Ser Gln Gln Glu Val Ile Ser
        1540                1545                1550

Ala Leu Arg Gly Thr Ala Pro Glu Val Phe Leu Leu Leu Cys Arg Pro
    1555                1560                1565

Pro Pro Gly Val Leu Pro Glu Ile Asp Thr Ala Leu Leu Thr Pro Leu
    1570                1575                1580

Gln Ser Pro Ala Gln Val Leu Pro Asn Ser Ser Lys Asp Ser Ser Gln
1585                1590                1595                1600

Pro Ser Cys Val Glu Gln Ser Thr Ser Ser Asp Glu Asn Glu Met Ser
            1605                1610                1615

Asp Lys Ser Lys Lys Gln Cys Lys Ser Pro Ser Arg Arg Asp Ser Tyr
        1620                1625                1630

Ser Asp Ser Ser Gly Ser Gly Glu Asp Asp Leu Val Thr Ala Pro Ala
    1635                1640                1645

Asn Ile Ser Asn Ser Thr Trp Ser Ser Ala Leu His Gln Thr Leu Ser
    1650                1655                1660

Asn Met Val Ser Gln Ala Gln Ser His His Glu Ala Pro Lys Ser Gln
1665                1670                1675                1680

Glu Asp Thr Ile Cys Thr Met Phe Tyr Tyr Pro Gln Lys Ile Pro Asn
            1685                1690                1695
```

```
Lys Pro Glu Phe Glu Asp Ser Asn Pro Ser Pro Leu Pro Pro Asp Met
            1700                1705                1710
Ala Pro Gly Gln Ser Tyr Gln Pro Gln Ser Glu Ser Ala Ser Ser Ser
            1715                1720            1725
Ser Met Asp Lys Tyr His Ile His His Ile Ser Glu Pro Thr Arg Gln
        1730                1735                1740
Glu Asn Trp Thr Pro Leu Lys Asn Asp Leu Glu Asn His Leu Glu Asp
1745                1750                1755                1760
Phe Glu Leu Glu Val Glu Leu Leu Ile Thr Leu Ile Lys Ser Glu Lys
                1765                1770                1775
Ala Ser Leu Gly Phe Thr Val Thr Lys Gly Asn Gln Arg Ile Gly Cys
            1780                1785                1790
Tyr Val His Asp Val Ile Gln Asp Pro Ala Lys Ser Asp Gly Arg Leu
            1795                1800                1805
Lys Pro Gly Asp Arg Leu Ile Lys Val Asn Asp Thr Asp Val Thr Asn
            1810                1815                1820
Met Thr His Thr Asp Ala Val Asn Leu Leu Arg Ala Ala Ser Lys Thr
1825                1830                1835                1840
Val Arg Leu Val Ile Gly Arg Val Pro Arg Ile Thr Gln Asn Thr Asn
                1845                1850                1855
Val Ala Ser Phe Ala Thr Gly His Lys Leu Thr Cys Asn Lys Glu Glu
            1860                1865                1870
Leu Gly Phe Ser Leu Cys Gly Gly His Asp Ser Leu Tyr Gln Val Val
        1875                1880                1885
Tyr Ile Ser Asp Ile Asn Pro Arg Ser Val Ala Ala Ile Glu Gly Asn
        1890                1895                1900
Leu Gln Leu Leu Asp Val Ile His Tyr Val Asn Gly Val Ser Thr Gln
1905                1910                1915                1920
Gly Met Thr Leu Glu Glu Val Asn Arg Ala Leu Asp Met Ser Leu Pro
            1925                1930                1935
Ser Leu Val Leu Lys Ala Thr Arg Asn Asp Leu Pro Val Val Pro Ser
            1940                1945                1950
Ser Lys Arg Ser Ala Val Ser Ala Pro Lys Ser Thr Lys Gly Asn Gly
        1955                1960                1965
Ser Tyr Ser Val Gly Ser Cys Ser Gln Pro Ala Leu Thr Pro Asn Asp
        1970                1975                1980
Ser Phe Ser Thr Val Ala Gly Glu Glu Ile Asn Glu Ile Ser Tyr Pro
1985                1990                1995                2000
Lys Gly Lys Cys Ser Thr Tyr Gln Ile Lys Gly Ser Pro Asn Leu Thr
            2005                2010                2015
Leu Pro Lys Glu Ser Tyr Ile Gln Glu Asp Asp Ile Tyr Asp Asp Ser
            2020                2025                2030
Gln Glu Ala Glu Val Ile Gln Ser Leu Leu Asp Val Val Asp Glu Glu
            2035                2040                2045
Ala Gln Asn Leu Leu Asn Glu Asn Ala Ala Gly Asp Ser Cys Gly
            2050                2055            2060
Pro Gly Thr Leu Lys Met Asn Gly Lys Leu Ser Glu Glu Arg Thr Glu
2065                2070                2075                2080
Asp Thr Asp Cys Asp Gly Ser Pro Leu Pro Glu Tyr Phe Thr Glu Ala
                2085                2090                2095
Thr Lys Met Asn Gly Cys Glu Glu Tyr Cys Glu Glu Lys Val Lys Ser
            2100                2105                2110
```

```
Glu Ser Leu Ile Gln Lys Pro Gln Glu Lys Lys Thr Asp Asp Glu
        2115                2120                2125

Ile Thr Trp Gly Asn Asp Glu Leu Pro Ile Glu Arg Thr Asn His Glu
    2130                2135                2140

Asp Ser Asp Lys Asp His Ser Phe Leu Thr Asn Asp Glu Leu Ala Val
2145                2150                2155                2160

Leu Pro Val Val Lys Val Leu Pro Ser Gly Lys Tyr Thr Gly Ala Asn
                2165                2170                2175

Leu Lys Ser Val Ile Arg Val Leu Arg Gly Leu Leu Asp Gln Gly Ile
            2180                2185                2190

Pro Ser Lys Glu Leu Glu Asn Leu Gln Glu Leu Lys Pro Leu Asp Gln
        2195                2200                2205

Cys Leu Ile Gly Gln Thr Lys Glu Asn Arg Arg Lys Asn Arg Tyr Lys
    2210                2215                2220

Asn Ile Leu Pro Tyr Asp Ala Thr Arg Val Pro Leu Gly Asp Glu Gly
2225                2230                2235                2240

Gly Tyr Ile Asn Ala Ser Phe Ile Lys Ile Pro Val Gly Lys Glu Glu
                2245                2250                2255

Phe Val Tyr Ile Ala Cys Gln Gly Pro Leu Pro Thr Thr Val Gly Asp
            2260                2265                2270

Phe Trp Gln Met Ile Trp Glu Gln Lys Ser Thr Val Ile Ala Met Met
        2275                2280                2285

Thr Gln Glu Val Glu Gly Glu Lys Ile Lys Cys Gln Arg Tyr Trp Pro
    2290                2295                2300

Asn Ile Leu Gly Lys Thr Thr Met Val Ser Asn Arg Leu Arg Leu Ala
2305                2310                2315                2320

Leu Val Arg Met Gln Gln Leu Lys Gly Phe Val Val Arg Ala Met Thr
                2325                2330                2335

Leu Glu Asp Ile Gln Thr Arg Glu Val Arg His Ile Ser His Leu Asn
            2340                2345                2350

Phe Thr Ala Trp Pro Asp His Asp Thr Pro Ser Gln Pro Asp Asp Leu
        2355                2360                2365

Leu Thr Phe Ile Ser Tyr Met Arg His Ile His Arg Ser Gly Pro Ile
    2370                2375                2380

Ile Thr His Cys Ser Ala Gly Ile Gly Arg Ser Gly Thr Leu Ile Cys
2385                2390                2395                2400

Ile Asp Val Val Leu Gly Leu Ile Ser Gln Asp Leu Asp Phe Asp Ile
                2405                2410                2415

Ser Asp Leu Val Arg Cys Met Arg Leu Gln Arg His Gly Met Val Gln
            2420                2425                2430

Thr Glu Asp Gln Tyr Ile Phe Cys Tyr Gln Val Ile Leu Tyr Val Leu
        2435                2440                2445

Thr Arg Leu Gln Ala Glu Glu Gly Gln Lys Gln Gln Pro Gln Leu Leu
    2450                2455                2460

Lys
2465

(2) INFORMATION FOR SEQ ID NO:4:

(i) SEQUENCE CHARACTERISTICS:
        (A) LENGTH: 369 amino acids
        (B) TYPE: amino acid
        (D) TOPOLOGY: linear (ii) MOLECULE TYPE: protein
```

(xi) SEQUENCE DESCRIPTION: SEQ ID NO:4:

```
Met Val Gln Pro Glu Gln Ala Pro Lys Val Leu Asn Val Val Asp
  1               5                  10                  15

Pro Gln Gly Arg Gly Ala Pro Glu Ile Lys Ala Thr Thr Ala Thr Ser
                 20                  25                  30

Val Cys Pro Ser Pro Phe Lys Met Lys Pro Ile Gly Leu Gln Glu Arg
         35                  40                  45

Arg Gly Ser Asn Val Ser Leu Thr Leu Asp Met Ser Ser Leu Gly Asn
         50                  55                  60

Ile Glu Pro Phe Val Ser Ile Pro Thr Pro Arg Glu Lys Val Ala Met
 65                  70                  75                  80

Glu Tyr Leu Gln Ser Ala Ser Arg Ile Leu Asp Lys Val Gln Leu Arg
                 85                  90                  95

Asp Val Val Ala Ser Ser His Leu Leu Gln Ser Glu Phe Met Glu Ile
                100                 105                 110

Pro Met Asn Phe Val Asp Pro Lys Glu Ile Asp Ile Pro Arg His Gly
            115                 120                 125

Thr Lys Asn Arg Tyr Lys Thr Ile Leu Pro Asn Pro Leu Ser Arg Val
130                 135                 140

Cys Leu Arg Pro Lys Asn Val Thr Asp Ser Leu Ser Thr Tyr Ile Asn
145                 150                 155                 160

Ala Asn Tyr Ile Arg Gly Tyr Ser Gly Lys Glu Lys Ala Phe Ile Ala
                165                 170                 175

Thr Gln Gly Pro Met Ile Asn Thr Val Asp Asp Phe Trp Gln Met Val
            180                 185                 190

Trp Gln Glu Asp Ser Pro Val Ile Val Met Ile Thr Lys Leu Lys Glu
            195                 200                 205

Lys Asn Glu Lys Cys Val Leu Tyr Trp Pro Glu Lys Arg Gly Ile Tyr
210                 215                 220

Gly Lys Val Glu Val Leu Val Ile Ser Val Asn Glu Cys Asp Asn Tyr
225                 230                 235                 240

Thr Ile Arg Asn Leu Val Leu Lys Gln Gly Ser His Thr Gln His Val
                245                 250                 255

Ser Asn Tyr Trp Tyr Thr Ser Trp Pro Asp His Lys Thr Pro Asp Ser
            260                 265                 270

Ala Gln Pro Leu Leu Gln Leu Met Leu Asp Val Glu Glu Asp Arg Leu
            275                 280                 285

Ala Ser Gln Gly Pro Arg Ala Val Val His Cys Ser Ala Gly Ile
290                 295                 300

Gly Arg Thr Gly Cys Phe Ile Ala Thr Ser Ile Gly Cys Gln Gln Leu
305                 310                 315                 320

Lys Glu Glu Gly Val Val Asp Ala Leu Ser Ile Val Cys Gln Leu Arg
                325                 330                 335

Met Asp Arg Gly Gly Met Val Gln Thr Ser Glu Gln Tyr Glu Phe Val
            340                 345                 350

His His Ala Leu Cys Leu Tyr Glu Ser Arg Leu Ser Ala Glu Thr Val
            355                 360                 365

Gln
```

(2) INFORMATION FOR SEQ ID NO:5:

(i) SEQUENCE CHARACTERISTICS:
        (A) LENGTH: 8 amino acids
        (B) TYPE: amino acid (C) STRANDEDNESS: single
            (D) TOPOLOGY: linear (ii) MOLECULE TYPE: peptide (iii) HYPOTHETICAL: NO (iv) ANTI-SENSE: NO (ix) FEATURE:
            (A) NAME/KEY: Region
            (B) LOCATION: 5
            (D) OTHER INFORMATION: /note= "Xaa = I or V"

(xi) SEQUENCE DESCRIPTION: SEQ ID NO:5:

Phe Trp Arg Met Xaa Trp Glu Gln
1               5

(2) INFORMATION FOR SEQ ID NO:6:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:6:

TTCTGGMGNA TGATNTGGGA ACA                                               23

(2) INFORMATION FOR SEQ ID NO:7:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (ix) FEATURE:
            (A) NAME/KEY: Region
            (B) LOCATION: 3
            (D) OTHER INFORMATION: /note= "Xaa = A or D"

(xi) SEQUENCE DESCRIPTION: SEQ ID NO:7:

Lys Cys Xaa Glx Tyr Trp Pro
1               5

(2) INFORMATION FOR SEQ ID NO:8:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (xi) SEQUENCE DESCRIPTION: SEQ ID NO:8:

AARTGYGANC AGTAYTGGCC                                                    20

(2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Region
        (B) LOCATION: 6
        (D) OTHER INFORMATION: /note= "Xaa = V or I"

(xi) SEQUENCE DESCRIPTION: SEQ ID NO:9:

His Cys Ser Ala Gly Xaa Gly
1               5

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:10:

CCNACNCCMG CRCTGCAGTG                                                    20

(2) INFORMATION FOR SEQ ID NO:11:

(i) SEQUENCE CHARACTERISTICS:
        (A) LENGTH: 303 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:11:

Arg Lys Val Asn Ile Met Leu Leu Asn Gly Gln Arg Leu Glu Leu Thr
1               5                   10                  15

Cys Asp Thr Lys Thr Ile Cys Lys Asp Val Phe Asp Met Val Val Ala
                20                  25                  30

His Ile Gly Leu Val Glu His His Leu Phe Ala Leu Ala Thr Leu Lys
            35                  40                  45

Asp Asn Glu Tyr Phe Phe Val Asp Pro Asp Leu Lys Leu Thr Lys Val
        50                  55                  60

Ala Pro Glu Gly Trp Lys Glu Glu Pro Lys Lys Thr Lys Ala Thr
65                  70                  75                  80

```
Val Asn Phe Thr Leu Phe Phe Arg Ile Lys Phe Phe Met Asp Asp Val
            85                  90                  95

Ser Leu Ile Gln His Thr Leu Thr Cys His Gln Tyr Tyr Leu Gln Leu
            100                 105                 110

Arg Lys Asp Ile Leu Glu Glu Arg Met His Cys Asp Glu Thr Ser
            115                 120             125

Leu Leu Leu Ala Ser Leu Ala Leu Gln Ala Glu Tyr Gly Asp Tyr Gln
            130                 135                 140

Pro Glu Val His Gly Val Ser Tyr Phe Arg Met Glu His Tyr Leu Pro
145                     150                 155                 160

Ala Arg Val Met Glu Lys Leu Asp Leu Ser Tyr Ile Lys Glu Glu Leu
                165                 170                 175

Pro Lys Leu His Asn Thr Tyr Val Gly Ala Ser Glu Lys Glu Thr Glu
            180                 185                 190

Leu Glu Phe Leu Lys Val Cys Gln Arg Leu Thr Glu Tyr Gly Val His
            195                 200                 205

Phe His Arg Val His Pro Glu Lys Lys Ser Gln Thr Gly Ile Leu Leu
210                     215                 220

Gly Val Cys Ser Lys Gly Val Leu Val Phe Glu Val His Asn Gly Val
225                 230                 235                     240

Arg Thr Leu Val Leu Arg Phe Pro Trp Arg Glu Thr Lys Lys Ile Ser
            245                 250                 255

Phe Ser Lys Lys Lys Ile Thr Leu Gln Asn Thr Ser Asp Gly Ile Lys
            260                 265                 270

His Gly Phe Gln Thr Asp Asn Ser Lys Ile Cys Gln Tyr Leu Leu His
            275                 280                 285

Leu Cys Ser Tyr Gln His Lys Phe Gln Leu Gln Met Arg Ala Arg
            290                 295                 300

(2) INFORMATION FOR SEQ ID NO:12:

(i) SEQUENCE CHARACTERISTICS:
        (A) LENGTH: 296 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:12:

Ile Asn Val Arg Val Thr Thr Met Asp Ala Glu Leu Glu Phe Ala Ile
1               5                   10                  15

Gln Pro Asn Thr Thr Gly Lys Gln Leu Phe Asp Gln Val Val Lys Thr
            20                  25                  30

Ile Gly Leu Arg Glu Val Trp Tyr Phe Gly Leu His Tyr Val Asp Asn
        35                  40                  45

Lys Gly Phe Pro Thr Trp Leu Lys Leu Asp Lys Lys Val Ser Ala Gln
        50                  55                  60

Glu Val Arg Lys Glu Asn Pro Leu Gln Phe Lys Phe Arg Ala Lys Phe
65                  70                  75                  80

Tyr Pro Glu Asp Val Ala Glu Glu Leu Ile Gln Asp Ile Thr Gln Lys
            85                  90                  95
```

-continued

Leu Phe Phe Leu Gln Val Lys Glu Gly Ile Leu Ser Asp Glu Ile Tyr
                100                 105                 110

Cys Pro Pro Glu Thr Ala Val Leu Leu Gly Ser Tyr Ala Val Gln Ala
            115                 120                 125

Lys Phe Gly Asp Tyr Asn Lys Glu Val His Lys Ser Gly Tyr Leu Ser
            130                 135                 140

Ser Glu Arg Leu Ile Pro Gln Arg Val Met Asp Gln His Lys Leu Thr
145                 150                 155                 160

Arg Asp Gln Trp Glu Asp Arg Ile Gln Val Trp His Ala Glu His Arg
                165                 170                 175

Gly Met Leu Lys Asp Asn Ala Met Leu Glu Tyr Leu Lys Ile Ala Gln
            180                 185                 190

Asp Leu Glu Met Tyr Gly Ile Asn Tyr Phe Glu Ile Lys Asn Lys Lys
            195                 200                 205

Gly Thr Asp Leu Trp Leu Gly Val Asp Ala Leu Gly Leu Asn Ile Tyr
210                 215                 220

Glu Lys Asp Asp Lys Leu Thr Pro Lys Ile Gly Phe Pro Trp Ser Glu
225                 230                 235                 240

Ile Arg Asn Ile Ser Phe Asn Asp Lys Lys Phe Val Ile Lys Pro Ile
                245                 250                 255

Asp Lys Lys Ala Pro Asp Phe Val Phe Tyr Ala Pro Arg Leu Arg Ile
            260                 265                 270

Asn Lys Arg Ile Leu Gln Leu Cys Met Gly Asn His Glu Leu Tyr Met
            275                 280                 285

Arg Arg Arg Lys Pro Asp Thr Ile
290                 295

(2) INFORMATION FOR SEQ ID NO:13:

(i) SEQUENCE CHARACTERISTICS:
        (A) LENGTH: 247 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:13:

Met His Cys Lys Val Ser Leu Leu Asp Asp Thr Val Tyr Glu Cys Val
1               5                   10                  15

Val Glu Lys His Ala Lys Gly Gln Asp Leu Leu Lys Arg Val Cys Glu
            20                  25                  30

His Leu Asn Leu Leu Glu Glu Asp Tyr Phe Gly Leu Ala Ile Trp Asp
            35                  40                  45

Asn Ala Asp Ile Thr Arg Tyr Tyr Leu Cys Leu Gln Leu Arg Gln Asp
      50                  55                  60

Ile Val Ala Gly Arg Leu Pro Cys Ser Phe Ala Thr Leu Ala Leu Leu
65                  70                  75                  80

Gly Ser Tyr Thr Ile Gln Ser Glu Leu Gly Asp Tyr Asp Pro Glu Leu
                85                  90                  95

His Gly Val Asp Tyr Val Ser Asp Phe Lys Leu Ala Pro Asn Gln Thr
            100                 105                 110

-continued

```
Lys Glu Leu Glu Glu Lys Val Met Glu Leu His Lys Ser Tyr Arg Ser
            115                 120                 125

Met Thr Pro Ala Gln Ala Asp Leu Glu Phe Leu Glu Asn Ala Lys Lys
        130                 135                 140

Leu Ser Met Tyr Gly Val Asp Leu His Lys Ala Lys Asp Leu Glu Gly
145                 150                 155                 160

Val Asp Ile Ile Leu Gly Val Cys Ser Ser Gly Leu Leu Val Tyr Lys
                165                 170                 175

Asp Lys Leu Arg Ile Asn Arg Phe Pro Trp Pro Lys Val Leu Lys Ile
            180                 185                 190

Ser Tyr Lys Arg Ser Ser Phe Phe Ile Lys Ile Arg Pro Gly Glu Gln
            195                 200                 205

Glu Gln Tyr Glu Ser Thr Ile Gly Phe Lys Leu Pro Ser Tyr Arg Ala
        210                 215                 220

Ala Lys Lys Leu Trp Lys Val Cys Val Glu His His Thr Phe Phe Arg
225                 230                 235                 240

Leu Thr Ser Thr Asp Thr Ile
                245
```

(2) INFORMATION FOR SEQ ID NO:14:

(i) SEQUENCE CHARACTERISTICS:
        (A) LENGTH: 288 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:14:

```
Val Val Cys Asn Ile Leu Leu Asp Asn Thr Val Gln Ala Phe Lys
1               5                   10                  15

Val Asn Lys His Asp Gln Gly Gln Val Leu Leu Asp Val Val Phe Lys
            20                  25                  30

His Leu Asp Leu Thr Glu Gln Asp Tyr Phe Gly Leu Gln Leu Ala Asp
        35                  40                  45

Asp Ser Thr Asp Asn Pro Arg Trp Leu Asp Pro Asn Lys Pro Ile Arg
50                  55                  60

Lys Gln Leu Lys Arg Gly Ser Pro Tyr Ser Leu Asn Phe Arg Val Lys
65                  70                  75                  80

Phe Phe Val Ser Asp Pro Asn Lys Leu Gln Glu Glu Tyr Thr Arg Tyr
                85                  90                  95

Gln Tyr Phe Leu Gln Ile Lys Gln Asp Ile Leu Thr Gly Arg Leu Pro
            100                 105                 110

Cys Pro Ser Asn Thr Ala Ala Leu Leu Ala Ser Phe Ala Val Gln Ser
            115                 120                 125

Glu Leu Gly Asp Tyr Asp Gln Ser Glu Asn Leu Ser Gly Tyr Leu Ser
        130                 135                 140

Asp Tyr Ser Phe Ile Pro Asn Gln Pro Gln Asp Phe Glu Lys Glu Ile
145                 150                 155                 160

Ala Lys Leu His Gln Gln His Ile Gly Leu Ser Pro Ala Glu Ala Glu
                165                 170                 175
```

```
Phe Asn Tyr Leu Asn Thr Ala Arg Thr Leu Glu Leu Tyr Gly Val Glu
            180                 185                 190

Phe His Tyr Ala Arg Asp Gln Ser Asn Asn Glu Ile Met Ile Gly Val
            195                 200                 205

Met Ser Gly Gly Ile Leu Ile Tyr Lys Asn Arg Val Arg Met Asn Thr
            210                 215                 220

Phe Pro Trp Leu Lys Ile Val Lys Ile Ser Phe Lys Cys Lys Gln Phe
225                 230                 235                 240

Phe Ile Gln Leu Arg Lys Glu Leu His Glu Ser Arg Glu Thr Leu Leu
            245                 250                 255

Gly Phe Asn Met Val Asn Tyr Arg Ala Cys Lys Asn Leu Trp Lys Ala
            260                 265                 270

Cys Val Glu His His Thr Phe Phe Arg Leu Asp Arg Pro Leu Pro Pro
            275                 280                 285

(2) INFORMATION FOR SEQ ID NO:15:

(i) SEQUENCE CHARACTERISTICS:
        (A) LENGTH: 288 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:15:

Val Ile Cys Ser Ile His Phe Leu Asp Gly Val Val Gln Thr Phe Lys
1               5                   10                  15

Val Thr Lys Gln Asp Thr Gly Gln Val Leu Leu Asp Met Val His Asn
            20                  25                  30

His Leu Gly Val Thr Glu Lys Glu Tyr Phe Gly Leu Gln His Asp Asp
            35                  40                  45

Asp Ser Val Asp Ser Pro Arg Trp Leu Glu Ala Ser Lys Pro Ile Arg
50                  55                  60

Lys Gln Leu Lys Gly Gly Phe Pro Cys Thr Leu His Phe Arg Val Arg
65                  70                  75                  80

Phe Phe Ile Pro Asp Pro Asn Thr Leu Gln Gln Glu Gln Thr Arg His
            85                  90                  95

Leu Tyr Phe Leu Gln Leu Lys Met Asp Ile Cys Glu Gly Arg Leu Thr
            100                 105                 110

Cys Pro Leu Asn Ser Ala Val Val Leu Ala Ser Tyr Ala Val Gln Ser
            115                 120                 125

His Phe Gly Asp Tyr Asn Ser Ser Ile His Pro Gly Tyr Leu Ser
            130                 135                 140

Asp Ser His Phe Ile Pro Asp Gln Asn Glu Asp Phe Leu Thr Lys Val
145                 150                 155                 160

Glu Ser Leu His Glu Gln His Ser Gly Leu Lys Gln Ser Glu Ala Glu
            165                 170                 175

Ser Cys Tyr Ile Asn Ile Ala Arg Thr Leu Asp Phe Tyr Gly Val Glu
            180                 185                 190

Leu His Ser Gly Arg Asp Leu His Asn Leu Asp Leu Met Ile Gly Ile
            195                 200                 205
```

```
Ala Ser Ala Gly Val Ala Val Tyr Arg Lys Tyr Ile Cys Thr Ser Phe
    210                 215                 220

Tyr Pro Trp Val Asn Ile Leu Lys Ile Ser Phe Lys Arg Lys Lys Phe
225                 230                 235                 240

Phe Ile His Gln Arg Gln Lys Gln Ala Glu Ser Arg Glu His Ile Val
                245                 250                 255

Ala Phe Asn Met Leu Asn Tyr Arg Ser Cys Lys Asn Leu Trp Lys Ser
                260                 265                 270

Cys Val Glu His His Thr Phe Phe Gln Ala Lys Lys Leu Leu Pro Gln
                275                 280                 285
```

(2) INFORMATION FOR SEQ ID NO:16:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:16:

```
Asp Ala Lys Tyr Gly Leu Gly Phe Gln Ile Ile Gly Gly Glu Lys Met
1               5                   10                  15

Gly Arg Leu Asp Leu Gly Ile Phe Ile Ser Ser Val Ala Pro Gly Gly
                20                  25                  30

Pro Ala Asp Phe His Gly Cys Leu Lys Pro Gly Asp Arg Leu Ile Ser
            35                  40                  45

Val Asn Ser Val Ser Leu Glu Gly Val Ser His His Ala Ala Ile Glu
    50                  55                  60

Ile Leu Gln Asn Ala Pro Glu Asp Val Thr Leu Val Ile
65                  70                  75
```

(2) INFORMATION FOR SEQ ID NO:17:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:17:

```
Lys Asn Asp Asn Ser Leu Gly Ile Ser Val Thr Gly Gly Val Asn Thr
1               5                   10                  15

Ser Val Arg His Gly Gly Ile Tyr Val Lys Ala Val Ile Pro Gln Gly
                20                  25                  30

Ala Ala Glu Ser Asp Gly Arg Ile His Lys Gly Asp Arg Val Leu Ala
            35                  40                  45

Val Asn Gly Val Ser Leu Glu Gly Ala Thr His Lys Gln Ala Val Glu
    50                  55                  60
```

```
Thr Leu Arg Asn Thr Gly Gln Val Val His Leu Leu Leu
 65                  70                  75
```

(2) INFORMATION FOR SEQ ID NO:18:

(i) SEQUENCE CHARACTERISTICS:
        (A) LENGTH: 80 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:18:

```
Lys Asn Ser Ser Gly Leu Gly Phe Ser Phe Ser Arg Glu Asp Asn Leu
 1               5                  10                  15

Ile Pro Glu Gln Ile Asn Ala Ser Ile Val Arg Val Lys Lys Leu Phe
                20                  25                  30

Ala Gly Gln Pro Ala Ala Glu Ser Gly Lys Ile Asp Val Gly Asp Val
             35                  40                  45

Ile Leu Lys Val Asn Gly Ala Ser Leu Lys Gly Leu Ser Gln Gln Glu
 50                  55                  60

Val Ile Ser Ala Leu Arg Gly Thr Ala Pro Glu Val Phe Leu Leu Leu
 65                  70                  75                  80
```

(2) INFORMATION FOR SEQ ID NO:19:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:19:

```
Ser Glu Lys Ala Ser Leu Gly Phe Thr Val Thr Lys Gly Asn Gln Arg
 1               5                  10                  15

Ile Gly Cys Tyr Val His Asp Val Ile Gln Asp Pro Ala Lys Ser Asp
                20                  25                  30

Gly Arg Leu Lys Pro Gly Asp Arg Leu Ile Lys Val Asn Asp Thr Asp
             35                  40                  45

Val Thr Asn Met Thr His Thr Asp Ala Val Asn Leu Leu Arg Ala Ala
 50                  55                  60

Ser Lys Thr Val Arg Leu Val Ile
 65                  70
```

(2) INFORMATION FOR SEQ ID NO:20:

(i) SEQUENCE CHARACTERISTICS:
        (A) LENGTH: 75 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:20:

Cys Asn Lys Asx Glu Leu Gly Phe Ser Leu Cys Gly Gly His Asp Ser
1               5                   10                  15

Leu Tyr Gln Val Val Tyr Ile Ser Asp Ile Asn Pro Arg Ser Val Ala
            20                  25                  30

Ala Ile Glu Gly Asn Leu Gln Leu Leu Asp Val Ile His Tyr Val Asn
        35                  40                  45

Gly Val Ser Thr Gln Gly Met Thr Leu Glu Glu Val Asn Arg Ala Leu
    50                  55                  60

Asp Met Ser Leu Pro Ser Leu Val Leu Lys Ala
65                  70                  75

(2) INFORMATION FOR SEQ ID NO:21:

(i) SEQUENCE CHARACTERISTICS:
        (A) LENGTH: 75 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:21:

Asp Glu Asp Gly Lys Pro Gly Phe Asn Leu Lys Gly Gly Val Asp Gln
1               5                   10                  15

Lys Asn Pro Leu Val Val Ser Arg Ile Asn Pro Ser Ser Pro Ala Asp
            20                  25                  30

Thr Cys Ile Pro Lys Leu Asn Glu Gly Asp Gln Ile Val Leu Ile Asn
        35                  40                  45

Gly Arg Asp Ile Ser Glu His Thr His Asp Gln Val Val Met Phe Ile
    50                  55                  60

Lys Ala Ser Arg Glu Ser His Ser Arg Glu Leu
65                  70                  75

(2) INFORMATION FOR SEQ ID NO:22:

(i) SEQUENCE CHARACTERISTICS:
        (A) LENGTH: 75 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:22:

Asp Glu Asn Gly Arg Phe Gly Phe Asn Val Lys Gly Gly Tyr Asp Gln
1               5                   10                  15

Lys Met Pro Val Ile Val Ser Arg Val Ala Pro Gln Thr Pro Ala Asp
            20                  25                  30

Leu Cys Val Pro Arg Leu Asn Glu Gly Asp Gln Val Val Leu Ile Asn
        35                  40                  45

```
Gly Arg Asp Ile Ala Glu His Thr His Asp Gln Val Val Leu Phe Ile
    50                  55                  60

Lys Ala Ser Cys Glu Arg His Ser Gly Glu Leu
 65                  70                  75
```

(2) INFORMATION FOR SEQ ID NO:23:

(i) SEQUENCE CHARACTERISTICS:
        (A) LENGTH: 79 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:23:

```
Arg Gly Asn Ser Gly Leu Gly Phe Ser Ile Ala Gly Gly Thr Asp Asn
 1               5                  10                  15

Pro His Ile Gly Thr Asp Thr Ser Ile Tyr Ile Thr Lys Leu Ile Ser
                20                  25                  30

Gly Gly Ala Ala Ala Ala Asp Gly Arg Leu Ser Ile Asn Asp Ile Ile
            35                  40                  45

Val Ser Val Asn Asp Val Ser Val Val Asp Pro His Ala Ser Ala
     50                  55                  60

Val Asp Ala Leu Lys Lys Ala Gly Asn Val Val Lys Leu His Val
 65                  70                  75
```

(2) INFORMATION FOR SEQ ID NO:24:

(i) SEQUENCE CHARACTERISTICS:
        (A) LENGTH: 83 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:24:

```
Lys Gly Gly Lys Gly Leu Gly Phe Ser Ile Ala Gly Gly Ile Gly Asn
 1               5                  10                  15

Gln His Ile Pro Gly Asp Asn Gly Ile Tyr Val Thr Lys Leu Thr Asp
                20                  25                  30

Gly Gly Arg Ala Gln Val Asp Gly Arg Leu Ser Ile Gly Asp Lys Leu
            35                  40                  45

Ile Ala Val Arg Thr Asn Gly Ser Glu Lys Asn Leu Glu Asn Val Thr
     50                  55                  60

His Glu Leu Ala Val Ala Thr Leu Lys Ser Ile Thr Asp Lys Val Thr
 65                  70                  75                  80

Leu Ile Ile
```

(2) INFORMATION FOR SEQ ID NO:25:

(i) SEQUENCE CHARACTERISTICS:
        (A) LENGTH: 73 amino acids
        (B) TYPE: amino acid

```
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:25:

Lys Gly Pro Gln Gly Leu Gly Phe Asn Ile Val Gly Gly Glu Asp Gly
1               5                  10                  15

Gln Gly Ile Tyr Val Ser Phe Ile Leu Ala Gly Gly Pro Ala Asp Leu
            20                  25                  30

Gly Ser Glu Leu Lys Arg Gly Asp Gln Leu Leu Ser Val Asn Asn Val
        35                  40                  45

Asn Leu Thr His Ala Thr His Glu Ala Ala Gln Ala Leu Lys Thr
    50                  55                  60

Ser Gly Gly Val Val Thr Leu Leu Ala
65                  70

(2) INFORMATION FOR SEQ ID NO:26:

(i) SEQUENCE CHARACTERISTICS:
         (A) LENGTH: 79 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:26:

Arg Gly Asn Ser Gly Leu Gly Phe Ser Ile Ala Gly Gly Thr Asp Asn
1               5                  10                  15

Pro His Ile Gly Asp Asp Pro Ser Ile Phe Ile Thr Lys Ile Ile Pro
            20                  25                  30

Gly Gly Ala Ala Ala Gln Asp Gly Arg Leu Arg Val Asn Asp Ser Ile
        35                  40                  45

Leu Phe Val Asn Glu Val Asp Val Arg Glu Val Thr His Ser Ala Ala
    50                  55                  60

Val Glu Ala Leu Lys Glu Ala Gly Ser Ile Val Arg Leu Tyr Val
65                  70                  75

(2) INFORMATION FOR SEQ ID NO:27:

(i) SEQUENCE CHARACTERISTICS:
         (A) LENGTH: 79 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:27:

Lys Gly Pro Lys Gly Leu Gly Phe Ser Ile Ala Gly Gly Val Gly Asn
1               5                  10                  15
```

-continued

```
Gln His Ile Pro Gly Asp Asn Ser Ile Tyr Val Thr Lys Ile Ile Glu
            20                  25                  30

Gly Gly Ala Ala His Lys Asp Gly Arg Leu Gln Ile Gly Asp Lys Ile
        35                  40                  45

Leu Ala Val Asn Ser Val Gly Leu Glu Asp Val Met His Glu Asp Ala
50                  55                  60

Val Ala Ala Leu Lys Asn Thr Tyr Asp Val Val Tyr Leu Lys Val
65                  70                  75
```

(2) INFORMATION FOR SEQ ID NO:28:

(i) SEQUENCE CHARACTERISTICS:
        (A) LENGTH: 73 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:28:

```
Arg Gly Ser Thr Gly Leu Gly Phe Asn Ile Val Gly Gly Glu Asp Gly
1               5                   10                  15

Glu Gly Ile Phe Ile Ser Phe Ile Leu Ala Gly Gly Pro Ala Asp Leu
            20                  25                  30

Ser Gly Glu Leu Arg Lys Gly Asp Gln Ile Leu Ser Val Asn Gly Val
        35                  40                  45

Asp Leu Arg Asn Ala Ser His Glu Gln Ala Ala Ile Ala Leu Lys Asn
50                  55                  60

Ala Gly Gln Thr Val Thr Ile Ile Ala
65                  70
```

(2) INFORMATION FOR SEQ ID NO:29:

(i) SEQUENCE CHARACTERISTICS:
        (A) LENGTH: 78 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:29:

```
His Arg Ala Pro Gly Phe Gly Ile Ala Ile Ser Gly Gly Arg Asp Asn
1               5                   10                  15

Pro His Phe Gln Ser Gly Glu Thr Ser Ile Val Ile Ser Asp Val Leu
            20                  25                  30

Lys Gly Gly Pro Ala Asx Gly Gln Leu Gln Glu Asn Asn Arg Val Ala
        35                  40                  45

Met Val Asn Gly Val Ser Met Asp Asn Val Glu His Ala Phe Ala Val
50                  55                  60

Gln Gln Leu Arg Lys Ser Gly Lys Asn Ala Lys Ile Thr Ile
65                  70                  75
```

(2) INFORMATION FOR SEQ ID NO:30:

(i) SEQUENCE CHARACTERISTICS:
        (A) LENGTH: 68 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:30:

```
Arg Lys Asn Glu Glu Tyr Gly Leu Arg Pro Ala Ser His Ile Phe Val
1               5                   10                  15

Lys Glu Ile Ser Gln Asp Ser Leu Ala Ala Arg Asp Gly Asp Ile Gln
            20                  25                  30

Glu Gly Asp Val Val Leu Lys Ile Asn Gly Thr Val Thr Glu Asn Met
        35                  40                  45

Ser Leu Thr Asp Ala Lys Thr Leu Ile Glu Arg Ser Lys Gly Lys Leu
    50                  55                  60

Lys Met Val Val
65
```

(2) INFORMATION FOR SEQ ID NO:31:

(i) SEQUENCE CHARACTERISTICS:
        (A) LENGTH: 71 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:31:

```
Arg Lys Gly Asp Ser Val Gly Leu Arg Leu Ala Gly Gly Asn Asp Val
1               5                   10                  15

Gly Ile Phe Val Ala Gly Val Leu Glu Asp Ser Pro Ala Ala Lys Glu
            20                  25                  30

Gly Leu Glu Glu Gly Asp Gln Ile Leu Arg Val Asn Asn Val Asp Phe
        35                  40                  45

Thr Asn Ile Ile Arg Glu Glu Ala Val Leu Phe Leu Leu Asp Leu Pro
    50                  55                  60

Lys Gly Glu Glu Val Thr Ile
65                  70
```

(2) INFORMATION FOR SEQ ID NO:32:

(i) SEQUENCE CHARACTERISTICS:
        (A) LENGTH: 72 amino acids
        (B) TYPE: amino acid
        (C) STRANDEDNESS: single
        (D) TOPOLOGY: linear (ii) MOLECULE TYPE: peptide (iii) HYPOTHETICAL: NO -continued (iv) ANTI-SENSE: NO (xi) SEQUENCE DESCRIPTION: SEQ ID NO:32:

```
Val Thr Glu Glu Pro Met Gly Ile Thr Leu Lys Leu Asn Glu Lys Gln
1               5                   10                  15

Ser Cys Thr Val Ala Arg Ile Leu His Gly Gly Met Ile His Arg Gln
            20                  25                  30

Gly Ser Leu His Val Gly Asp Glu Ile Leu Glu Ile Asn Gly Thr Asn
        35                  40                  45

Val Thr Asn His Ser Val Asp Gln Leu Gln Lys Ala Met Lys Glu Thr
    50                  55                  60

Lys Gly Met Ile Ser Leu Lys Val
65                  70
```

(2) INFORMATION FOR SEQ ID NO:33:

(i) SEQUENCE CHARACTERISTICS:
        (A) LENGTH: 74 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:33:

```
Arg Lys Val Gly Gly Leu Gly Phe Leu Val Lys Glu Arg Val Ser Pro
1               5                   10                  15

Lys Lys Pro Val Ile Ile Ser Asp Leu Ile Arg Gly Gly Ala Ala Glu
            20                  25                  30

Gln Ser Gly Leu Ile Gln Ala Gly Asp Ile Ile Leu Ala Val Asn Asp
        35                  40                  45

Arg Pro Leu Val Asp Leu Ser Tyr Asp Ser Ala Leu Glu Val Leu Arg
    50                  55                  60

Gly Ile Ala Ser Glu Thr His Val Val Leu
65                  70
```

(2) INFORMATION FOR SEQ ID NO:34:

(i) SEQUENCE CHARACTERISTICS:
        (A) LENGTH: 74 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

```
Glu Asp His Glu Gly Leu Gly Ile Ser Ile Thr Gly Gly Leu Glu His
1               5                   10                  15

Gly Val Pro Ile Leu Ile Ser Gly Ile His Pro Gly Gln Pro Ala Asp
            20                  25                  30

Arg Cys Gly Gly Leu His Val Gly Asp Ala Ile Leu Ala Val Asn Gly
        35                  40                  45

Val Asn Leu Arg Asp Thr Leu His Leu Gly Ala Val Thr Ile Leu Ser
    50                  55                  60

Gln Gln Arg Gly Glu Ile Glu Phe Glu Val
65                  70
```

NUCLEIC ACIDS CODING FOR GLM-2, A NOVEL PROTEIN TYROSINE PHOSPHATASE

This application is a divisional of U.S. application Ser. No. 08/596,291, filed Aug. 9, 1996, now U.S. Pat. No. 5,821,075, which is a national stage application under 35 U.S.C. §371 of PCT/US94/09943, filed Sep. 1, 1994, which is a continuation of U.S. application Ser. No. 08/115,573, filed Sep. 1, 1993, now abandoned.

FIELD OF THE INVENTION

This invention relates to the isolation and cloning of nucleic acids encoding two novel protein tyrosine phosphatases (PTPs). Specifically, the present invention relates to the isolation and cloning of two PTPs from human glioblastoma cDNA which have been designated PTPL1 and GLM-2. The present invention provides isolated PTP nucleic acid sequences; isolated PTP anti-sense sequences; vectors containing such nucleic acid sequences; cells, cell lines and animal hosts transformed by a recombinant vector so as to exhibit increased, decreased, or differently regulated expression of the PTPs; isolated probes for identifying sequences substantially similar or homologous to such sequences; substantially pure PTP proteins and variants or fragments thereof; antibodies or other agents which bind to these PTPs and variants or fragments thereof; methods of assaying for activity of these PTPs; methods of assessing the regulation of PTPL1 or GLM-2; and methods of identifying and/or testing drugs which may affect the expression or activity of these PTPs.

BRIEF DESCRIPTION OF THE BACKGROUND ART

Protein tyrosine phosphorylation plays an essential role in the regulation of cell growth, proliferation and differentiation (reviewed in Hunter, T. (1987) *Cell* 50:823–8291). This dynamic process is modulated by the counterbalancing activities of protein tyrosine kinases (PTKs) and protein tyrosine phophatases (PTPs). The recent elucidation of intracellular signaling pathways has revealed important roles for PTKS. Conserved domains like the Src homology 2 (SH2) (Suh, P.-G., et al., (1988) *Proc. Natl. Acad. Sci. (USA)* 85:5419–5423) and the Src homology 3 (SH3) (Mayer, B. J., et al., (1988) *Nature* 352:272–275) domains have been found to determine the interaction between activated PTKs and signal transducing molecules (reviewed in Pawson, T., and Schiessinger, J. (1993) *Current Biol.* 3:434–442; Koch, C. A., et al., (1991) *Science* 252:668–674). The overall effect of such protein interactions is the formation of signaling cascades in which phosphorylation and dephosphorylation of proteins on tyrosine residues are major events. The involvement of PTPs in such signaling cascades is beginning to emerge from studies on the regulation and mechanisms of action of several representatives of this broad family of proteins.

Similarly to PTKS, PTPs can be classified according to their secondary structure into two broad groups, i.e. cytoplasmic and transmembrane molecules (reviewed in Charbonneau, H., and Tonks, N. K. (1992) *Annu. Rev. Cell Biol.* 8:463–493; Pot, D. A., and Dixon, J. E. (1992) *Biochim. Biophys. Acta* 1136:35–43). Transmembrane PTPs have the structural organization of receptors and thus the potential to initiate cellular signaling in response to external stimuli. These molecules are characterized by the presence of a single transmembrane segment and two tandem PTP domains; only two examples of transmembrane PTPs that have single PTP domains are known, HPTP-P (Krueger, N. X., et al., (1990) *EMBO J.* 9:3241–3252) and DPTP10D (Tian, S.-S., et al., (1991) *Cell* 67:675–685).

Nonreceptor PTPs display a single catalytic domain and contain, in addition, non-catalytic amino acid sequences which appear to control intracellular localization of the molecules and which may be involved in the determination of substrate specificity (Mauro, L. J., and Dixon, J. E. (1994) *TIBS* 19:151–155) and have also been suggested to be regulators of PTP activity (Charbonneau, H., and Tonks, N. K. (1992) *Annu. Rev. Cell Biol.* 8:463–493). PTP1B (Tonks, N. K., et al., (1988) *J. Biol. Chem.* 263:6731–6737) is localized to the cytosolic face of the endoplasmic reticulum via its C-terminal 35 amino acids (Frangioni, J. V., et al., (1992) *Cell* 68:545–560). The proteolytic cleavage of PTP1B by the calcium dependent neutral protease calpain occurs upstream from this targeting sequence, and results in the relocation of the enzyme from the endoplasmic reticulum to the cytosol; such relocation is concomitant with a two-fold stimulation of PTP1B enzymatic activity (Frangioni, J. V., et al., (1993) *EMBO J.* 12:4843–4856). Similarly, the 11 kDa C-terminal domain of T-cell PTP (Cool, D. E., et al., (1989) *Proc. Natl. Acad. Sci. (USA)* 86:5257–5261) has also been shown to be responsible for enzyme localization and functional regulation (Cool, D. E., et al., (1990) *Proc. Natl. Acad. Sci. (USA)* 87:7280–7284; Cool, D. E., et al., (1992) *Proc. Natl. Acad. Sci. (USA)* 89:5422–5426).

PTPs containing SH2 domains have been described including PTP1C (Shen, S.-H., et al., (1991) *Nature* 352:736–739), also named HCP (Yi, T., et al., (1992) *Mol. Cell. Biol.* 12:836–846), SHP (Matthews, R. J., et al., (1992) *Mol. Cell. Biol* 12:2396–2405) or SH-PTP1 (Plutzky, J., et al., (1992) *Proc. Natl. Acad. Sci. (USA)* 89:1123–1127), and the related phosphatase PTP2C (Ahmad, S., et al., (1993) *Proc. Natl. Acad. Sci. (USA)* 90:2197–2201), also termed SH-PTP2 (Freeman Jr., R. M., et al., (1992) *Proc. Natl. Acad. Sci. (USA)* 89:11239–11243), SH-PTP3 (Adachi, M., et al., (1992) *FEBS Letters* 314:335–339), PTP1D (Vogel, W., et al., (1993) *Science* 259:1611–1614) or Syp (Feng, G.-S., et al., (1993) *Science* 259:1607–1611). The Drosophila csk gene product (Perkins, L. A., et al., (1992) *Cell* 70:225–236) also belongs to this subfamily. PTP1C has been shown to associate via its SH2 domains with ligand-activated c-Kit and CSF-1 receptor PTKs (Yi, T., and Ihle, J. N. (1993) *Mol. Cell. Biol.* 13:3350–3358; Young, Y.-G., et al., (1992) *J. Biol. Chem.* 267:23447–23450) but only association with activated CSF-1 receptor is followed by tyrosine phosphorylation of PTP1C. Syp interacts with and is phosphorylated by the ligand activated receptors for epidermal growth factor and platelet-derived growth factor (Feng, G.-S., et al., (1993) *Science* 259:1607–1611). Syp has also been reported to associate with tyrosine phosphorylated insulin receptor substrate 1 (Kuhne, M. R., et al., (1993) *J. Biol. Chem.* 268:11479–11481).

Two PTPs have been identified, PTPH1 (Yang, Q., and Tonks, N. K. (1991) *Proc. Natl. Acad. Sci. (USA)* 88:5949–5953) and PTPase MEG (Gu, M., et al., (1991) *Proc. Natl. Acad. Sci. (USA)* 88:5867–5871), which contain a region in their respective N-terminal segments with similarity to the cytoskeletal- associated proteins band 4.1 (Conboy, J., et al., (1986) *Proc. Natl. Acad. Sci. (USA)* 83:9512–9516), ezrin (Gould, K. L., et al., (1989) *EMBO J.* 8:4133–4142), talin (Rees, D. J. G., et al., (1990) *Nature* 347:685–689) and radixin (Funayama, N., et al., (1991) *J. Cell Biol.* 115:1039–1048). The function of proteins of the band 4.1 family appears to be the provision of anchors for cytoskeletal proteins at the inner surface of the plasma membrane (Conboy, J., et al., (1986) *Proc. Natl. Acad. Sci. (USA)* 83:9512–9516; Gould, K. L., et al., (1989) *EMBO J.* 8:4133–4142). It has been postulated that PTPH1 and PTPase MEG would, like members of this family, localize at the interface between the plasma membrane and the cytoskeleton and thereby be involved in the modulation of cytoskeletal function (Tonks, N. K., et al., (1991) *Cold Spring Harbor Symposia on Quantitative Biology* LVI:265–273).

The interest in studying PTKs and PTPs is particularly great in cancer research. For example, approximately one third of the known oncogenes include PTKs (Hunter, T. (1989) In *Oncogenes and Molecular Origins of Cancer*, R. Weinberg, Ed., Coldspring Harbor Laboratory Press, New York). In addition, the extent of tyrosine phosphorylation closely correlates with the manifestation of the transformed phenotype in cells infected by temperature-sensitive mutants of rous sarcoma virus. (Sefton, B., et al., (1980) *Cell* 20:807–816) Similarly, Brown-Shirner and colleagues demonstrated that over-expression of PTP1B in 3T3 cells suppressed the transforming potential of oncogenic neu, as measured by focus formation, anchorage-independent growth and tumorigenicity (Brown-Shirner, S., et al., (1992) *Cancer Res.* 52:478–482). Because they are direct antagonists of PTK activity, the PTPs also may provide an avenue of treatment for cancers caused by excessive PTK activity. Therefore, the isolation, characterization and cloning of various PTPs is an important step in developing, for example, gene therapy to treat PTK oncogene cancers.

SUMMARY OF THE INVENTION

The present invention is based upon the molecular cloning of previously uncloned and previously undisclosed nucleic acids encoding two novel PTPs. The disclosed sequences encode PTPs which we have designated PTPL1 and GLM-2. (PTPL1 was previously designated GLM-1 in U.S. patent application Ser. No. 08/115,573 filed Sep. 1, 1993.) In particular, the present invention is based upon the molecular cloning of PTPL1 and GLM-2 PTP sequences from human glioblastoma cells. The invention provides isolated cDNA and RNA sequences corresponding to PTPL1 and GLM-2 transcripts and encoding the novel PTPs. In addition, the present invention provides vectors containing PTPL1 or GLM-2 cDNA sequences, vectors capable of expressing PTPL1 or GLM-2 sequences with endogenous or exogenous promoters, and hosts transformed with one or more of the above-mentioned vectors. Using the sequences disclosed herein as probes or primers in conjunction with such techniques as PCR cloning, targeted gene walking, and colony/plaque hybridization with genomic or cDNA libraries, the invention further provides for the isolation of allelic variants of the disclosed sequences, endogenous PTPL1 or GLM-2 regulatory sequences, and substantially similar or homologous PTPL1 or GLM-2 DNA and RNA sequences from other species including mouse, rat, rabbit and non-human primates.

The present invention also provides fragments and variants of isolated PTPL1 and GLM-2 sequences, fragments and variants of isolated PTPL1 or GLM-2 RNA, vectors containing variants or fragments of PTPL1 or GLM-2 sequences, vectors capable of expressing variants or fragments of PTPL1 or GLM-2 sequences with endogenous or exogenous regulatory sequences, and hosts transformed with one or more of the above-mentioned vectors. The invention further provides variants or fragments of substantially similar or homologous PTPL1 and GLM-2 DNA and RNA sequences from species including mouse, rat, rabbit and non-human primates.

The present invention provides isolated PTPL1 and GLM-2 anti-sense DNA, isolated PTPL1 and GLM-2 anti-sense RNA, vectors containing PTPL1 or GLM-2 anti-sense DNA, vectors capable of expressing PTPL1 or GLM-2 anti-sense DNA with endogenous or exogenous promoters, and hosts transformed with one or more of the above-mentioned vectors. The invention further provides the related PTPL1 or GLM-2 anti-sense DNA and anti-sense RNA sequences from other species including mouse, rat, rabbit and non-human primates.

The present invention also provides fragments and variants of isolated PTPL1 and GLM-2 anti-sense DNA, fragments and variants of isolated PTPL1 and GLM-2 anti-sense RNA, vectors containing fragments or variants of PTPL1 and GLM-2 anti-sense DNA, vectors capable of expressing fragments or variants of PTPL1 and GLM-2 anti-sense DNA with endogenous or exogenous promoters, and hosts transformed with one or more of the above-mentioned vectors. The invention further provides fragments or variants of the related PTPL1 and GLM-2 anti-sense DNA and PTPL1 and GLM-2 anti-sense RNA sequences from other species including mouse, rat, rabbit and non-human primates.

Based upon the sequences disclosed herein and techniques well known in the art, the invention also provides isolated probes useful for detecting the presence or level of expression of a sequence identical, substantially similar or homologous to the disclosed PTPL1 and GLM-2 sequences. The probes may consist of the PTPL1 and GLM-2 DNA, RNA or anti-sense sequences disclosed herein. The probe may be labeled with, for example, a radioactive isotope; immobilized as, for example, on a filter for Northern or Southern blotting; or may be tagged with any other sort of marker which enhances or facilitates the detection of binding. The probes may be oligonucleotides or synthetic oligonucleotide analogs.

The invention also provides substantially pure PTPL1 and GLM-2 proteins. The proteins may be obtained from natural sources using the methods disclosed herein or, in particular, the invention provides substantially pure PTPL1 and GLM-2 proteins produced by a host cell or transgenic animal transformed by one of the vectors disclosed herein.

The invention also provides substantially pure variants and fragments of PTPL1 and GLM-2 proteins.

Using the substantially pure PTPL1 or GLM-2 protein or variants or fragments of the PTPL1 or GLM-2 protein which are disclosed herein, the present invention provides methods of obtaining and identifying agents capable of binding to either PTPL1 or GLM-2. Specifically, such agents include antibodies, peptides, carbohydrates and pharmaceutical agents. The agents may include natural ligands, co-factors, accessory proteins or associated peptides, modulators, regulators, or inhibitors. The entire PTPL1 or GLM-2 protein may be used to test or develop such agents or variants or fragments thereof may be employed. In particular, only certain domains of the PTPL1 or GLM-2 protein may be employed. The invention further provides detectably labeled, immobilized and toxin-conjugated forms of these agents.

The present invention also provides methods for assaying for PTPL1 or GLM-2 PTP activity. For example, using the PTPL1 and GLM-2 anti-sense probes disclosed herein, the presence and level of either PTPL1 or GLM-2 expression may be determined by hybridizing the probes to total or selected mRNA from the cell or tissue to be studied.

Alternatively, using the antibodies or other binding agents disclosed herein, the presence and level of PTPL1 or GLM-2 protein may be assessed. Such methods may, for example, be employed to determine the tissue-specificity of PTPL1 or GLM-2 expression.

The present invention also provides methods for assessing the regulation of PTPL1 or GLM-2 function. Such methods include fusion of the regulatory regions of the PTPL1 or GLM-2 nucleic acid sequences to a marker locus, introduction of this fusion product into a host cell using a vector, and testing for inducers or inhibitors of PTPL1 or GLM-2 by measuring expression of the marker locus. In addition, by using labeled PTPL1 and GLM-2 anti-sense transcripts, the level of expression of PTPL1 or GLM-2 mRNA may be ascertained and the effect of various endogenous and exogenous compounds or treatments on PTPL1 or GLM-2 expression may be determined. Similarly, the effect of various endogenous and exogenous compounds and treatments on PTPL1 or GLM-2 expression may be assessed by measuring the level of either PTPL1 or GLM-2 protein with labeled antibodies as disclosed herein.

The present invention provides methods for efficiently testing the activity or potency of drugs intended to enhance or inhibit PTPL1 or GLM-2 expression or activity. In particular, the nucleic acid sequences and vectors disclosed herein enable the development of cell lines and transgenic organisms with increased, decreased, or differently regulated expression of PTPL1 or GLM-2. Such cell lines and animals are useful subjects for testing pharmaceutical compositions.

The present invention further provides methods of modulating the activity of PTPL1 and GLM-2 PTPs in cells. Specifically, agents and, in particular, antibodies which are capable of binding to either PTPL1 or GLM-2 PTP are provided to a cell expressing PTPL1 or GLM-2. The binding of such an agent to the PTP can be used either to activate or inhibit the activity of the protein. In addition, PTPL1 and GLM-2 anti-sense transcripts may be administered such that they enter the cell and inhibit translation of the PTPL1 or GLM-2 mRNA and/or the transcription of PTPL1 or GLM-2 nucleic acid sequences. Alternatively, PTPL1 or GLM-2 RNA may be administered such that it enters the cell, serves as a template for translation and thereby augments production of PTPL1 or GLM-2 protein. In another embodiment, a vector capable of expressing PTPL1 or GLM-2 mRNA transcripts or PTPL1 or GLM-2 anti-sense RNA transcripts is administered such that it enters the cell and the transcripts are expressed.

BRIEF DESCRIPTION OF THE DRAWINGS

FIG. 1. Comparison of PTPL1 SEQ ID NO:11 with proteins of the band 4.1 superfamily (ezrin, -SEQ ID NO:12; band 4.1, -SEQ ID NO:13; PTPase MEG, -SEQ ID NO:14; PTPH1, -SEQ ID NO:15. The alignment was done using the Clustal V alignment program (Fazioli, F., et al., (1993) Oncogene 8:1335–1345). Identical amino acid residues conserved in two or more sequences, are boxed. A conserved tyrosine residue, which in ezrin has been shown to be phosphorylated by the epidermal growth factor receptor, is indicated by an asterisk.

FIG. 2. Comparison of amino acid sequences of GLGF-repeats. The alignment was done manually. Numbers of the GLGF-repeats are given starting from the N-terminus of the protein. Residues conserved in at least eight (42%) repeats are showed in bold letters. Five repeats are found In PTPL1 (SEQ ID NO:16, SEQ ID NO:17, SEQ ID NO:18, SEQ ID NO:19, and SEQ ID NO:20), three are found in the guanylate kinases, dlg-A gene product (SEQ ID NO:23, SEQ ID NO:24, and SEQ ID NO:25), PSD-95 (SEQ ID NO:26, SEQ ID NO:27, and SEQ ID NO:28) and the 220-kDa protein (SEQ ID NO:29, SEQ ID NO:30, and SEQ ID NO:31). One GLGF-repeat is found in the guanylate kinase p55 (SEQ ID NO:32), in the PTPs PTPH1 (SEQ ID NO:21) and PTPase MEG (SEQ ID NO:22), and in nitric oxide synthase (NOS) (SEQ ID NO:33). One repeat is also found in an altered rosl transcript from the glioma cell line U-118MG (SEQ ID NO:34), FIG. 3. Schematic diagram illustrating the domain strucure of PTPL1 and other GLGF-repeat containing proteins. Domains and motifs indicated in the Figure are L, leucine zipper motif; Band 4.1, band 4.1-like domain; G, GLGF-repeat; PTPase, catalytic PTPase domain; 3, SH3 domain; GK, guanylate kinase domain, Bind. Reg., co-enzyme binding region.

DETAILED DESCRIPTION OF THE INVENTION DEFINITIONS

Figure 3:
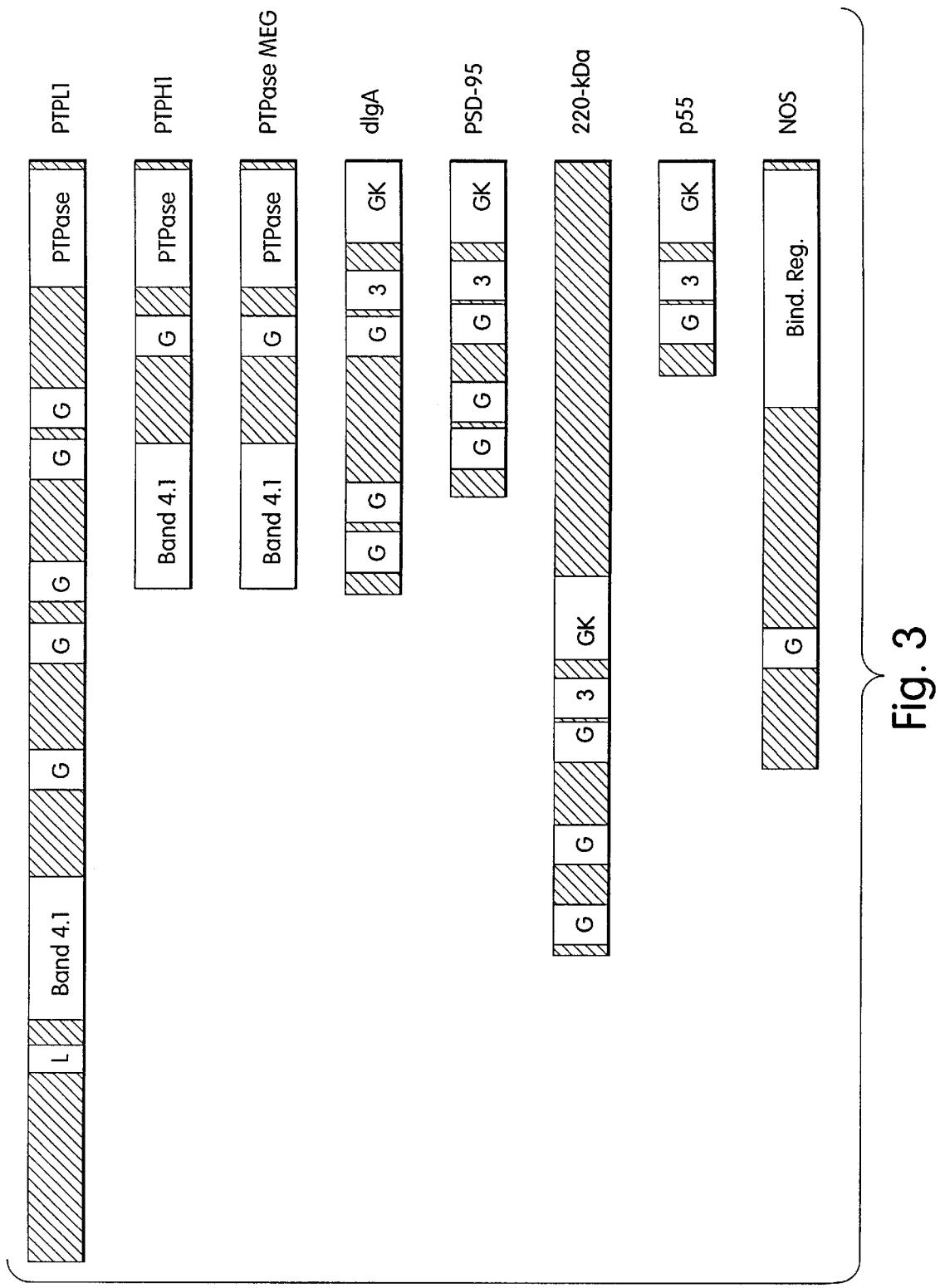

In the description that follows, a number of terms used in biochemistry, molecular biology, recombinant DNA (rDNA) technology and immunology are extensively utilized. In addition, certain new terms are introduced for greater ease of exposition and to more clearly and distinctly point out the subject matter of the invention. In order to provide a clear and consistent understanding of the specification and claims, including the scope to be given such terms, the following definitions are provided.

Gene

A gene is a nucleic acid sequence including a promoter region operably joined to a coding sequence which may serve as a template from which an RNA molecule may be transcribed by a nucleic acid polymerase. A gene contains a promoter sequence to which the polymerase binds, an initiation sequence which signals the point at which transcription should begin, and a termination sequence which signals the point at which transcription should end. The gene also may contain an operator site at which a repressor may bind to block the polymerase and to prevent transcription and/or may contain ribosome binding sites, capping signals, promoter, initiation, termination and, when present, operator sequences, ribosome binding sites, capping signals, transcription enhancers and polyadenylation signals are collectively referred to as regulatory sequences. Regulatory sequences 5' of the transcription initiation codon are collectively referred to as the promoter region. The sequences which are transcribed into RNA are the coding sequences. The RNA may or may not code for a protein. RNA that codes for a protein is processed into messenger RNA (mRNA). Other RNA molecules may serve functions or uses without ever being translated into protein. These include ribosomal RNA (rRNA), transfer RNA (tRNA), and the anti-sense RNAs of the present invention. In eukaryotes, coding sequences between the translation start codon (ATG) and the translation stop codon (TAA, TGA, or TAG) may be of two types: exons and introns. The exons are included in processed mRNA transcripts and are generally translated into a peptide or protein. Introns are excised from the RNA as it is processed into mature mRNA and are not translated into peptide or protein. As used herein, the word gene embraces both the gene including its introns, as may be obtained from genomic DNA, and the gene with the introns excised from the DNA, as may be obtained from cDNA.

Anti-sense DNA is defined as DNA that encodes anti-sense RNA and anti-sense RNA is RNA that is complementary to or capable of selectively hybridizing to some specified RNA transcript. Thus, anti-sense RNA for a particular gene would be capable of hybridizing with that gene's RNA transcript in a selective manner. Finally, an anti-sense gene is defined as a segment of anti-sense DNA operably joined to regulatory sequences such that the sequences encoding the anti-sense RNA may be expressed.

cDNA

Complementary DNA or cDNA is DNA which has been produced by reverse transcription from mature mRNA. In eukaryotes, sequences in RNA corresponding to introns in a gene are excised during mRNA processing. cDNA sequences, therefore, lack the intron sequences present in the genomic DNA to which they correspond. In addition, cDNA sequences will lack the regulatory sequences which are not transcribed into RNA. To create a functional cDNA gene, therefore, the cDNA sequence must be operably joined to a promoter region such that transcription may occur.

Operably Joined

A coding sequence and a promoter region are said to be operably joined when they are covalently linked in such a way as to place the expression or transcription of the coding sequence under the influence or control of the promoter region. If it is desired that the coding sequences be translated into a functional protein, two DNA sequences are said to be operably joined if induction of promoter function results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

If it is not desired that the coding sequence be eventually expressed as a protein or polypeptide, as in the case of anti-sense RNA expression, there is no need to ensure that the coding sequences and promoter region are joined without a frame-shift. Thus, a coding sequence which need not be eventually expressed as a protein or polypeptide is said to be operably joined to a promoter region if induction of promoter function results in the transcription of the RNA sequence of the coding sequences.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Such transcriptional control sequences may also include enhancer sequences or upstream activator sequences, as desired.

Vector

A vector may be any of a number of nucleic acid sequences into which a desired sequence may be inserted by restriction and ligation. Vectors are typically composed of DNA although RNA vectors are also available. Vectors include plasmids, phage, phasmids and cosmids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to a promoter region and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques.

Fragment

As used herein, the term "fragment" means both unique fragments and substantially characteristic fragments. As used herein, the term "fragment" is not to be construed according to standard dictionary definitions.

Substantially Characteristic Fragment

A "substantially characteristic fragment" of a molecule, such as a protein or nucleic acid sequence, is meant to refer to any portion of the molecule sufficiently rare or sufficiently characteristic of that molecule so as to identify it as derived from that molecule or to distinguish it from a class of unrelated molecules. A single amino acid or nucleotide, or a sequence of only two or three, cannot be a substantially characteristic fragment because all such short sequences occur frequently in nature.

A substantially characteristic fragment of a nucleic acid sequence is one which would have utility as a probe in identifying the entire nucleic acid sequence from which it is derived from within a sample of total genomic or cDNA. Under stringent hybridization conditions, a substantially characteristic fragment will hybridize only to the sequence from which it was derived or to a small class of substantially similar related sequences such as allelic variants, heterospecific homologous loci, and variants with small insertions, deletions or substitutions of nucleotides or nucleotide analogues. A substantially characteristic fragment may, under lower stringency hybridization conditions, hybridize with non-allelic and non-homologous loci and be used as a probe to find such loci but will not do so at higher stringency.

A substantially characteristic fragment of a protein would have utility in generating antibodies which would distinguish the entire protein from which it is derived, an allelomorphic protein or a heterospecific homologous protein from a mixture of many unrelated proteins.

It is within the knowledge and ability of one ordinarily skilled in the art to recognize, produce and use substantially characteristic fragments of nucleic acid sequences and proteins as, for example, probes for screening DNA libraries or epitopes for generating antibodies.

Unique Fragment

As used herein, a unique fragment of a protein or nucleic acid sequence is a substantially characteristic fragment not currently knows to occur elsewhere in nature (except in allelic or heterospecific homologous variants, i.e. it is present only in the PTPL1 or GLM-2 PTP or a PTPL1 or GLM-2 PTP "homologue"). A unique fragment will generally exceed 15 nucleotides or 5 amino acid residues. One of ordinary skill in the art can identify unique fragments by searching available computer databases of nucleic acid and protein sequences such as Genbank (Los Alamos National Laboratories, USA), SwissProt or the National Biomedical Research Foundation database. A unique fragment is particularly useful, for example, in generating monoclonal antibodies or in screening DNA or cDNA libraries.

Stringent Hybridization Conditions

"Stringent hybridization conditions" is a term of art understood by those of ordinary skill in the art. For any given nucleic acid sequence, stringent hybridization conditions are those conditions of temperature and buffer solution which will permit hybridization of that nucleic acid sequence to its complementary sequence and not to substantially different sequences. The exact conditions which constitute "stringent" conditions, depend upon the length of the nucleic acid sequence and the frequency of occurrence of subsets of that sequence within other non-identical sequences. By varying hybridization conditions from a level of stringency at which no hybridization occurs to a level at which hybridization is first observed, one of ordinary skill in the art can, without undue experimentation, determine conditions which will allow a given sequence to hybridize only with identical sequences. Suitable ranges of such stringency conditions are described in Krause, M. H. and S. A. Aaronson, *Methods in Enzymology*, 200:546–556 (1991). Stringent hybridization conditions, depending upon the length and commonality of a sequence, may include hybridization conditions of 30° C.–65° C. and from 5× to 0.1× SSPC. Less than stringent hybridization conditions are employed to isolate nucleic acid sequences which are substantially similar, allelic or homologous to any given sequence.

When using primers that are derived from nucleic acid encoding a PTPL1 or GLM-2 PTP, one skilled in the art will recognize that by employing high stringency conditions (e.g. annealing at 50–60° C.), sequences which are greater than about 75% homologous to the primer will be amplified. By employing lower stringency conditions (e.g. annealing at 35–37° C.), sequences which are greater than about 40–50% homologous to the primer will be amplified.

When using DNA probes derived from a PTPL1 or GLM-2 PTP for colony/plaque hybridization, one skilled in the art will recognize that by employing high stringency conditions (e.g. hybridization at 50–65° C., 5× SSPC, 50% formamide, wash at 50–65° C., 0.5× SSPC), sequences having regions which are greater than about 90% homologous to the probe can be obtained, and by employing lower stringency conditions (e.g. hybridization at 35–37° C., 5× SSPC, 40–45% formamide, wash at 42° C. SSPC), sequences having regions which are greater than 35–45% homologous to the probe will be obtained.

Substantially Similar

Two nucleic acid sequences are substantially similar if one of them or its anti-sense complement can bind to the other under strict hybridization conditions so as to distinguish that strand from all or substantially all other sequences in a cDNA or genomic library. Alternatively, one sequence is substantially similar to another if it or its anti-sense complement is useful as a probe in screening for the presence of its similar DNA or RNA sequence under strict hybridization conditions. Two proteins are substantially similar if they are encoded by substantially similar DNA or RNA sequences. In addition, even if they are not encoded by substantially similar nucleic acids, two proteins are substantially similar if they share sufficient primary, secondary and tertiary structure to perform the same biological role (structural or functional) with substantially the same efficacy or utility.

Variant

A "variant" of a protein or nucleic acid or fragment thereof is meant to include a molecule substantially similar in structure to the protein or nucleic acid, or to a fragment thereof. Variants of nucleic acid sequences include sequences with conservative nucleotide substitutions, small insertions or deletions, or additions. Variants of proteins include proteins with conservative amino acid substitutions, small insertions or deletions, or additions. Thus, nucleotide substitutions which do not effect the amino acid sequence of the subsequent translation product are particularly contemplated. Similarly, substitutions of structurally similar amino acids in proteins, such as leucine for isoleucine, or insertions, deletions, and terminal additions which do not destroy the functional utility of the protein are contemplated. Allelic variants of nucleic acid sequences and allelomorphic variants or protein or polypeptide sequences are particularly contemplated. As is well known in the art, an allelic variant is simply a naturally occurring variant of a polymorphic gene and that term is used herein as it is commonly used in the field of population genetics. The production of such variants is well known in the art and, therefore, such variants are intended to fall within the spirit and scope of the claims.

Homologous and Homologous

As used herein, the term "homologues" is intended to embrace either and/or both homologous nucleic acid sequences and homologous protein sequences as the context may indicate. Homologues are a class of variants, as defined above, which share a sufficient degree of structural and functional similarity so as to indicate to one of ordinary skill in the art that they share a common evolutionary origin and that the structural and functional similarity is the result of evolutionary conservation. To be considered homologues of the PTPL1 or GLM-2 PTP, nucleic acid sequences and the proteins they encode must meet two criteria: (1) The polypeptides encoded by homologous nucleic acids are at least approximately 50–60% identical and preferably at least 70% identical for at least one stretch of at least 20 amino acids. As is well known in the art, both the identity and the approximate positions of the amino acid residues relative to each other must be conserved and not just the overall amino acid composition. Thus, one must be able to "line up" the conserved regions of the homologues and conclude that there is 50–60% identity; and (2) The polypeptides must retain a functional similarity to the PTPL1 or GLM-2 PTP in that it is a protein tyrosine phosphatase.

Substantially Pure

The term "substantially pure" when applied to the proteins, variants or fragments thereof of the present invention means that the proteins are essentially free of other substances to an extent practical and appropriate for their intended use. In particular, the proteins are sufficiently pure and are sufficiently free from other biological constituents of their hosts cells so as to be useful in, for example, protein sequencing, or producing pharmaceutical preparations. By techniques well known in the art, substantially pure proteins, variants or fragments thereof may be produced in light of the nucleic acids of the present invention.

Isolated

Isolated refers to a nucleic acid sequence which has been: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid sequence is one which is readily manipulable by recombinant DNA techniques well known in the art. Thus, a nucleic acid sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid sequence that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

Immunogenetically Effective Amount

An "immunogenetically effective amount" is that amount of an antigen (e.g. a protein, variant or a fragment thereof) necessary to induce the production of antibodies which will bind to the epitopes of the antigen. The actual quantity comprising an "immunogenetically effective amount" will vary depending upon factors such as the nature of the antigen, the organism to be immunized, and the mode of immunization. The determination of such a quantity is well within the ability of one ordinarily skilled in the art without undue experimentation.

Antigen and Antibody

The term "antigen" as used in this invention is meant to denote a substance that can induce a detectable immune response to it when introduced to an animal. Such substances include proteins and fragments thereof.

The term "epitope" is meant to refer to that portion of an antigen which can be recognized and bound by an antibody. An antigen may have one, or more than one epitope. An "antigen" is capable of inducing an animal to produce antibody capable of binding to an epitope of that antigen. An "immunogen" is an antigen introduced into an animal specifically for the purpose of generating an immune response to the antigen. An antibody is said to be "capable of selectively binding" a molecule if it is capable of specifically reacting with the molecule to thereby bind the molecule to the antibody. The selective binding of an antigen and antibody is meant to indicate that the antigen will react, in a highly specific manner, with its corresponding antibody and not with the multitude of other antibodies which may be evoked by other antigens.

The term "antibody" (Ab) or "monoclonal antibody" (Mab) as used herein is meant to include intact molecules as well as fragments thereof (such as, for example, Fab and $F(ab')_2$ fragments) which are capable of binding an antigen. Fab and $F(ab')_2$ fragments lack the Fc fragment of intact antibody, clear more rapidly from the circulation, and may have less non-specific tissue binding than an intact antibody. Single chain antibodies, humanized antibodies, and fragments thereof, also are included.

DESCRIPTION OF THE PREFERRED EMBODIMENTS

The present invention relates to the identification, isolation and cloning of two novel protein tyrosine phosphatases designated PTPL1 and GLM-2. Specifically, the present invention discloses the isolation and cloning of cDNA and the amino acid sequences of PTPL1 and GLM-2 from human glioblastoma and brain cell cDNA libraries. These phosphatases are, initially, discussed separately below. As they are related in function and utility as well as structurally with respect to their catalytic domains, they are subsequently discussed in the alternative.

In order to identify novel PTPs, a PCR-based approach was used. PCR was performed using cDNA from the human glioma cell line U-343 MGa 31L as a template and degenerate primers that were based on conserved regions of PTPs. One primer was derived from the catalytic site (HCSAG) of the PTP domain and two primers were derived from conserved regions in the N-terminal part of the domain. Several PCR-products were obtained, including some corresponding to the cytoplasmic PTPs PTPH1 (Yang, Q., and Tonks, N. K. (1991) *Proc. Natl. Acad. Sci.* (*USA*) 88:5949–5953), PTPase MEG (Gu, M., et al., (1991) *Proc. Natl. Acad. Sci.* (*USA*) 88:5867–5871), P19PTP (den Hertog, J., et al., (1992) *Biochem. Biophys. Res. Commun.* 184:1241–1249), and TC-PTP (Cool, D. E., et al., (1989) *Proc. Natl. Acad. Sci.* (*USA*) 86:5257–5261), as well as to the receptor-like PTPs HPTP-α, HPTP-γ, and HPTP-δ (Krueger, N. X., et al., (1990) *EMBO J.* 9:3241–3252). In addition to these known sequences, three PCR-products encoding novel PTP-like sequences were found.

One of these PCR-products is almost identical to a PCR-product derived from a human leukemic cell line (Honda, H., et al., (1993) *Leukemia* 7:742–746) and was chosen for further characterization and was used to screen an oligo-(dT)-primed U-343 MGa 31L cDNA library which resulted in the isolation of the clone λ6.15. Upon Northern blot analysis of mRNA from human foreskin fibroblasts AG1518, probed with the λ6.15 insert, a transcript of 9.5 kb could be seen. Therefore AG1518 cDNA libraries were constructed and screened with λ6.15 in order to obtain a full-length clone. Screening of these libraries with λ6.15, and thereafter with subsequently isolated clones, resulted in several overlapping clones which together covered 8040 bp including the whole coding sequence of a novel phosphatase, denoted PTPL1. The total length of the open reading frame was 7398 bp coding for 2466 amino acids with a predicted molecular mass of 275 kDa. The nucleotide and deduced amino acid sequence of PTPL1 are disclosed as SEQ ID NO:1 and SEQ ID NO:2, respectively. Although the sequence surrounding the putative initiator codon at positions 78–80 does not conform well to the Kozak consensus sequence (Kozak, M. (1987) *Nucl. Acids Res.* 15:8125–8148) there is a purine at position -3 which is an important requirement for an initiation site. The 77 bp 5' untranslated region is GC-rich and contains an inframe stop codon at positions 45–47. A 3' untranslated region of 565 bp begins after a TGA stop codon at positions 7476–7478, and does not contain a poly-A tail.

Figure 1A:
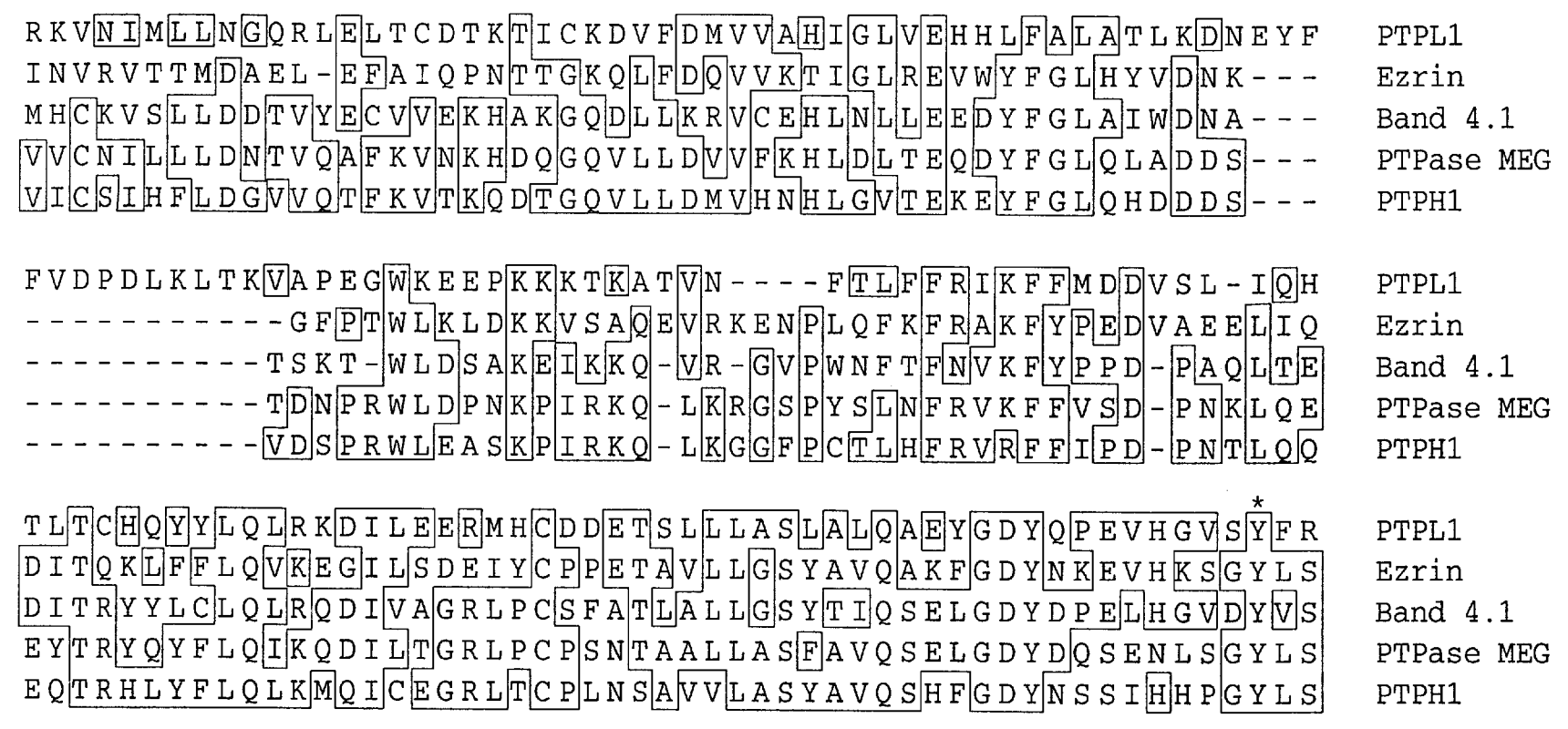

In the deduced amino acid sequence of PTPL1 no transmembrane domain or signal sequence for secretion are found, indicating that PTPL1 is a cytoplasmic PTP. Starting from the N-terminus, the sequence of the first 470 amino acid residues shows no homology to known proteins. The region 470–505 contains a leucine zipper motif, with a methionine in the position where the fourth leucine usually is found ($LX_6LX_6LX_6MX_6L$); similar replacements of leucine residues with methionine residues are also found in the leucine zippers of the transcription factors CYS-3 (Fu, Y.-H., et al., (1989) *Mol. Cell. Biol.* 9:1120–1127) and dFRA (Perkins, K. K., et al., (1990) *Genes Dev.* 4:822–834). Furthermore, consistent with the notion that this is a functional leucine zipper, no helix breaking residues (glycine and proline) are present in this region. The leucine zipper motif is followed by a 300 amino acid region (570–885) with homology to the band 4.1 superfamily (see FIG. 1). The members of this superfamily are cytoskeleton-associated proteins with a homologous domain in the N-terminus (Tsukita, S., et al., (1992) *Curr. Opin. Cell Biol.* 4:834–839). Interestingly, two cytoplasmic PTPs, PTPH1 and PTPase MEG, contain a band 4.1-like domain. The band 4.1-like domain of PTPL1 is 20% to 24% similar to most known proteins of this superfamily, including ezrin (Gould, K. L., et al., (1989) *EMBO J.* 8:4133–4142), moesin (Lankes, W. T., and Furthmayr, H. (1991) *Proc. Natl. Acad. Sci. (USA)* 88:8297–8301), radixin (Funayama, N., et al., (1991) *J. Cell Biol.* 115:1039–1048), merlin (Trofatter, J. A., et al., (1993) *Cell* 72:791–800), band 4.1 protein (Conboy, J., et al., (1986) *Proc. Natl. Acad. Sci. (USA)* 83:9512–9516), PTPH1 (Yang, Q., and Tonks, N. K. (1991) *Proc. Natl. Acad. Sci. (USA)* 88:5949–5953) and PTPase MEG (Gu, M., et al., (1991) *Proc. Natl. Acad. Sci. (USA)* 88:5867–5871).

Between am acid residues 1080 and 1940 there are five 80 amino acid repeats denoted GLGF-repeats. This repeat was first found in PSD-95 (Cho, K.-O., et al., (1992) *Neuron* 9:929–942), also called SAP (Kistner, U., et al., (1993) *J. Biol. Chem.* 268:4580–4583), a protein in post-synaptic densities, i.e. structures of the submembranous cytoskeleton in synaptic junctions. Rat PSD-95 is homologous to the discs-large tumor suppressor gene in Drosophila (Woods, D. F., and Bryant, P. J. (1991) *Cell* 66:451–464), dlg-A, which encodes a protein located in septate junctions. These two proteins each contain three GLGF-repeats, one SH-3 domain and a guanylate kinase domain. Through computer searches in protein data bases complemented by manual searches, 19 GLGF-repeats in 9 different proteins, all of them enzymes, were found (see FIG. 2 and FIG. 3). Besides dlg-A and PSD-95, there are two other members of the guanylate kinase family, a 220-kDa protein (Itoh, M., et al., (1993) *J. Cell Biol.* 121:491–502) which is a constitutive protein of the plasma membrane undercoat with three GLGF-repeats, and p55 (Ruff, P., et al., (1991) *Proc. Natl. Acad. Sci. (USA)* 88:6595–6599) which is a palmitoylated protein from erythrocyte membranes with one GLGF-repeat. A close look into the sequence of PTPH1 and PTPase MEG revealed that each of them has one GLGF-repeat between the band 4.1 homology domain and the PTP domain. One GLGF-repeat is also found in nitric oxide synthase from rat brain (Bredt, D. S., et al., (1991) *Nature* 351:714–718), and a glioma cell line, U-118MG, expresses an altered rosl transcript (Sharma, S., et al., (1989) *Oncogene Res.* 5:91–100), containing a GLGF-repeat probably as a result of a gene fusion.

The PTP domain of PTPL1 is localized in the C-terminus (amino acid residues 2195–2449). It contains most of the conserved motifs of PTP domains and shows about 30% similarity to known PTPs.

Use of a 9.5 kb probe including SEQ ID NO:1 for Northern blot analysis for tissue-specific expression showed high expression of PTPL1 in human kidney, placenta, ovaries, and testes; medium expression in human lung, pancreas, prostrate and brain; low expression in human heart, skeletal muscle, spleen, liver, small intestine and colon; and virtually no detectable expression in human leukocytes. Furthermore, using a rat PCR product for PTPL1 as a probe, PTPL1 was found to be expressed in adult rats but not in rat embryos. This latter finding suggests that PTPL1 may have a role, like many PTPs, in the signal transduction process that leads to cellular growth or differentiation.

The rabbit antiserum αL1A (see Example 5), made against a synthetic peptide derived from amino acid residues 1802–1823 in the PTPL1 sequence, specifically precipitated a component of 250 kDa from [$^{35}$S]methionine and [$^{35}$S] cysteine labeled COS-1 cells transfected with the PTPL1 cDNA. This component could not be detected in untransfected cells, or in transfected cells using either pre-immune serum or antiserum pre-blocked with the immunogenic peptide. Identical results were obtained using the antiserum αL1B (see Example 5) made against residues 450–470 of PTPL1. A component of about 250 kDa could also be detected in immunoprecipitations using AG1518 cells, PC-3 cells, CCL-64 cells, A549 cells and PAE cells. This component was not seen upon precipitation with the preimmune serum, or when precipitation was made with αL1A antiserum preblocked with peptide. The slight variations in sizes observed between the different cell lines could be due to species differences. A smaller component of 78 kDa was also specifically precipitated by the αL1A antiserum. The relationship between this molecule and PTPL1 remains to be determined.

Figure 4:
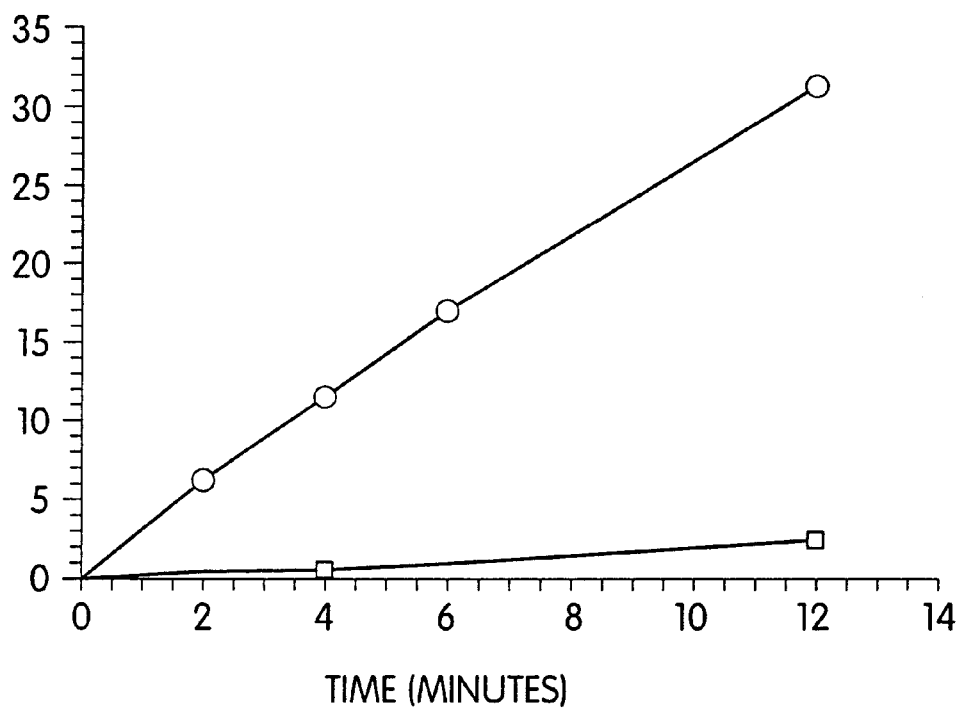
FIG. 4. PTP activity of PTPL1. Immunoprecipitates from COS-1 cells using an antiserum (αL1B) against PTPL1, unblocked (open circles) or blockeod with peptide (open squares), were incubated for 2, 4, 6 or 12 minutes with myelin basic protein, $^{32}$P-labeled on tyrosine residues. The amount of radioactivity released as inorganic phosphate is expressed as the percentage of the total input of radioactivity.

In order to demonstrate that PTPL1 has PTP activity, immunoprecipitates from COS-1 cells transfected with PTPL1 cDNA were incubated with myelin basic protein, $^{32}$P-labeled on tyrosine residues, as a substrate. The amount of radioactivity released as inorganic phosphate was measured. Immunoprecipitates with αL1B (open circles) gave a time-dependent increase in dephosphorylation with over 30% dephosphorylation after 12 minutes compared to 2% dephosphorylation when the antiserum was pre-blocked with peptide (open squares) (see FIG. 4).

The present invention also provides an isolated nucleic acid sequence encoding a novel PTP designated GLM-2, variants and fragments thereof, and uses relating thereto. One sequence encoding a GLM-2 PTP and surrounding nucleotides is disclosed as SEQ ID NO:2. This sequence includes the coding sequences for GLM-2 PTP as well as both 5' and 3' untranslated regions including regulatory sequences. The full disclosed sequence, designated SEQ ID NO:2 is 3090 bp in length.

The nucleic acid sequence of SEQ ID NO:2 includes 1310 base pairs of 5' untranslated region and 673 bp of 3' untranslated region which do not appear to encode a sequence for a poly-A (polyadenylation) tail. Transcription of SEQ ID NO:2 begins at approximately position 1146. A translation start codon (ATG) is present at positions 1311 to 1313 of SEQ ID NO:2. The nucleotides surrounding the start codon (AGCATGG) show substantial similarity to the Kozak consensus sequence (RCCATGG) (Kozak, M. (1987) *Nucl. Acids Res.* 15:8125–8148). A translation stop codon (TGA) is present at positions 2418 to 2420 of SEQ ID NO:2. The open reading frame of 1107 bp encodes a protein of 369 amino acid residues with a predicted molecular mass of 41 kD. The deduced amino acid sequence of this protein is disclosed as SEQ ID NO:4.

The sequence disclosed in SEQ ID NO:2 encodes a single domain PTP similar to the rat PTP STEP (53% identity; Lombroso, et al., 1991) and the human PTP LC-PTP (51% identity; Adachi, M., et al., (1992) *FEBS Letters* 314:335–339). None of the sequenced regions encodes a polypeptide sequence with any substantial similarity to known signal or transmembrane domains. Further indicating that GLM-2 is a cytoplasmic PTP.

Use of a 3.6 kb probe including SEQ ID NO:2 for Northern blot analysis for tissue-specific expression showed a strong association with human brain tissue and little or no expression in human heart, placenta, lung, liver, skeletal muscle, kidney or pancreas. This is similar to to the pattern of tissue-specific expression shown by STEP.

Cloning and expression of PTPL1 and GLM-2.

In one series of embodiments of the present invention, an isolated DNA, cDNA or RNA sequence encoding a PTPL1 or GLM-2 PTP, or a variant or fragment thereof, is provided. The procedures described above, which were employed to isolate the first PTPL1 and GLM-2 sequences no longer need be employed. Rather, using the sequences disclosed herein, a genomic DNA or cDNA library may be readily screened to isolate a clone containing at least a fragment of a PTPL1 or GLM-2 sequence and, if desired, a full sequence. Alternatively, one may synthesize PTPL1 and GLM-2 encoding nucleic acids using the sequences disclosed herein.

The present invention further provides vectors containing nucleic acid sequences encoding PTPL1 and GLM-2. Such vectors include, but are not limited to, plasmids, phage, plasmids and cosmid vectors. In light of the present disclosure, one of ordinary skill in the art can readily place the nucleic acid sequences of the present invention into any of a great number of known suitable vectors using routine procedures.

The source nucleic acids for a DNA library may be genomic DNA or cDNA. Which of these is employed depends upon the nature of the sequences sought to be cloned and the intended use of those sequences.

Genomic DNA may be obtained by methods well known to those or ordinary skill in the art (for example, see *Guide to Molecular Cloning Techniques*, S. L. Berger et al., eds., Academic Press (1987)). Genomic DNA is preferred when it is desired to clone the entire gene including its endogenous regulatory sequences. Similarly, genomic DNA is used when it is only the regulatory sequences which are of interest.

Complementary or cDNA may be produced by reverse transcription methods which are well known to those of ordinary skill in the art (for example, see *Guide to Molecular Cloning Techniques*, S. L. Berger et al., eds., Academic Press (1987)). Preferably, the mRNA preparation for reverse transcription should be enriched in the mRNA of the desired sequence. This may be accomplished by selecting cells in which the mRNA is produced at high levels or by inducing high levels of production. Alternatively, in vitro techniques may be used such as sucrose gradient centrifugation to isolate mRNA transcripts of a particular size. cDNA is preferred when the regulatory sequences of a gene are not needed or when the genome is very large in comparison with the expressed transcripts. In particular, cDNA is preferred when a eukaryotic gene containing introns is to be expressed in a prokaryotic host.

To create a DNA or cDNA library, suitable DNA or cDNA preparations are randomly sheared or enzymatically cleaved by restriction endonucleases to create fragments appropriate in size for the chosen library vector. The DNA or cDNA fragments may be inserted into the vector in accordance with conventional techniques, including blunt-ending or staggered-ending termini for ligation. Typically, this is accomplished by restriction enzyme digestion to provide appropriate termini, the filling-in of cohesive ends as appropriate, alkaline phosphatase treatment to avoid undesirable joining, and ligation with appropriate ligases. Techniques for such manipulations are well known in the art and may be found, for example, in Sambrook, et al., *Molecular Cloning, A Laboratory Manual*, 2d ed., Cold Spring Harbor Laboratory Press, Plainview, N.Y. (1989). The library will consist of a great many clones, each containing a fragment of the total DNA or cDNA. A great variety of cloning vectors, restriction endonucleases and ligases are commercially available and their use in creating DNA libraries is well known to those of ordinary skill in the art. See, for example, Sambrook, et al., *Molecular Cloning, A Laboratory Manual*, 2d ed., Cold Spring Harbor Laboratory Press, Plainview, N.Y. (1989).

DNA or cDNA libraries containing sequences coding for PTPL1 or GLM-2 nucleic acid sequences may be screened and a sequence coding for either PTPL1 or GLM-2 identified by any means which specifically selects for that sequence. Such means include (a) hybridization with an appropriate nucleic acid probe(s) containing a unique or substantially characteristic fragment of the desired DNA or cDNA (b) hybridization-selected translational analysis in which native mRNA which hybridizes to the clone in question is translated in vitro and the translation products are further characterized (c) if the cloned genetic sequences are themselves capable of expressing mRNA, immunoprecipitation of a translated PTPL1 or GLM-2 recombinant product produced by the host containing the clone, or prefearably (d) by using a unique or substantially characteristic fragment of the desired sequence as a PCR primer to amplify those clones with which it hybridizes.

Preferably, the probe or primer is a substantially characteristic fragment of one of the disclosed sequences. More preferably, the probe is a unique fragment of one of the disclosed sequences. In choosing a fragment, unique and substantially characteristic fragments can be identified by comparing the sequence of a proposed probe to the known sequences found in sequence databases. Alternatively, the entire PTPL1 or GLM-2 sequence may be used as a probe. In a preferred embodiment, the probe is a $^{32}$P random-labeled unique fragment of the PTPL1 or GLM-2 nucleic acid sequences disclosed herein. In a most preferred embodiment, the probe serves as a PCR primer containing a unique or substantially characteristic fragment of the PTPL1 or GLM-2 sequences disclosed herein.

The library to be screened may be DNA or cDNA. Preferably, a cDNA library is screened. In a preferred embodiment, a U-343 MGa 31L human glioblastoma (Nister, M., et al., (1988) *Cancer Res.* 48:3910–3918) or AG1518 human fibroblast (Human Genetic Mutant Cell Repository, Institute for Medical Research, Camden, N.J.) cDNA library is screened with a probe to a unique or substantially characteristic fragment of the PTPL1 sequence. Because PTPL1 is expressed in a wide variety of tissues, cDNA libraries from many tissues may be employedN n another preferred embodiment, a λgt10 human brain cDNA library (Clontech, Calif.) is screened with a probe to a unique or substantially characteristic fragment of the GLM-2 sequence. Because expression of GLM-2 appears to be high in brain tissues but low or absent in other tissues tested, a brain cDNA library is recommended for the cloning of GLM-2.

The selected fragments may be cloned into any of a great number of vectors known to those of ordinary skill in the art. In one preferred embodiment, the cloning vector is a plasmid such as pUC18 or Bluescript (Stratagene). The cloned sequences should be examined to determine whether or not they contain the entire PTPL1 or GLM-2 sequences or desired portions thereof. A series of overlapping clones of partial sequences may be selected and combined to produce a complete sequence by methods well known in the art.

In an alternative embodiment of cloning a PTPL1 or GLM-2 nucleotide sequence, a library is prepared using an expression vector. The library is then screened for clones which express the PTPL1 or GLM-2 protein, for example, by screening the library with antibodies to the protein or with labeled probes for the desired RNA sequences or by assaying for PTPL1 or GLM-2 PTP activity on a phosphorylated substrate such as para-nitrylphenyl phosphate. The above discussed methods are, therefore, capable of identifying cloned genetic sequences which are capable of expressing PTPL1 or GLM-2 PTPs, or variants or fragments thereof.

To express a PTPL1 or GLM-2 PTP, variants or fragments thereof, or PTPL1 or GLM-2 anti-sense RNA, and variants or fragments thereof, transcriptional and translational signals recognizable by an appropriate host are necessary. The cloned PTPL1 or GLM-2 encoding sequences, obtained through the methods described above, and preferably in a double-stranded form, may be operably joined to regulatory sequences in an expression vector, and introduced into a host cell, either prokaryote or eukaryote, to produce recombinant PTPL1 or GLM-2 PTP, a variant or fragment thereof, PTPL1 or GLM-2 anti-sense RNA, or a variant or fragment thereof.

Depending upon the purpose for which expression is desired, the host may be eukaryotic or prokaryotic. For example, if the intention is to study the regulation of PTPL1 or GLM-2 PTP in a search for inducers or inhibitors of its activity, the host is preferably eukaryotic. In one preferred embodiment, the eukaryotic host cells are COS cells derived from monkey kidney. In a particularly preferred embodiment, the host cells are human fibroblasts. Many other eukaryotic host cells may be employed as is well known in the art. For example, it is known in the art that Xenopus oocytes comprise a cell system useful for the functional expression of eukaryotic messenger RNA or DNA. This system has, for example, been used to clone the sodium:glucose cotransporter in rabbits (Hediger, M. A., et. al., *Proc. Natl. Acad. Sci. (USA)* 84:2634–2637 (1987)). Alternatively, if the intention is to produce large quantities of the PTPL1 or GLM-2 PTPs, a prokaryotic expression system is preferred. The choice of an appropriate expression system is within the ability and discretion of one of ordinary skill in the art.

Depending upon which strand of the PTPL1 or GLM-2 PTP encoding sequence is operably joined to the regulatory sequences, the expression vectors will produce either PTPL1 or GLM-2 PTPs, variants or fragments thereof, or will express PTPL1 and GLM-2 anti-sense RNA, variants or fragments thereof. Such PTPL1 and GLM-2 anti-sense RNA may be used to inhibit expression of the PTPL1 or GLM-2 PTP and/or the replication of those sequences.

Expression of a protein in different hosts may result in different post-translational modifications which may alter the properties of the protein. This is particularly true when eukaryotic genes are expressed in prokaryotic hosts. In the present invention, however, this is of less concern as PTPL1 and GLM-2 are cytoplasmic PTPs and are unlikely to be post-translationally glycosylated.

Transcriptional initiation regulatory sequences can be selected which allow for repression or activation, so that expression of the operably joined sequences can be modulated. Such regulatory sequences include regulatory sequences which are temperature-sensitive so that by varying the temperature, expression can be repressed or initiated, or which are subject to chemical regulation by inhibitors or inducers. Also of interest are constructs wherein both PTPL1 or GLM-2 mRNA and PTPL1 or GLM-2 anti-sense RNA are provided in a transcribable form but with different promoters or other transcriptional regulatory elements such that induction of PTPL1 or GLM-2 mRNA expression is accompanied by repression of the expression of the corresponding anti-sense RNA, or alternatively, repression of PTPL1 or GLM-2 mRNA expression is accompanied by induction of expression of the corresponding anti-sense RNA. Translational sequences are not necessary when it is desired to express PTPL1 and GLM-2 anti-sense RNA sequences.

A non-transcribed and/or non-translated sequence 5' or 3' to the sequence coding for PTPL1 or GLM-2 PTP can be obtained by the above-described cloning methods using one of the probes disclosed herein to select a clone from a genomic DNA library. A 5' region may be used for the endogenous regulatory sequences of the PTPL1 or GLM-2 PTP. A 3'-non-transcribed region may be utilized for a transcriptional termination regulatory sequence or for a translational termination regulatory sequence. Where the native regulatory sequences do not function satisfactorily in the host cell, then exogenous sequences functional in the host cell may be utilized.

The vectors of the invention further comprise other operably joined regulatory elements such as DNA elements which confer tissue or cell-type specific expression of an operably joined coding sequence.

Oligonucleotide probes derived from the nucleotide sequence of PTPL1 or GLM-2 can be used to identify genomic or cDNA library clones possessing a related nucleic acid sequence such as an allelic variant or homologous sequence. A suitable oligonucleotide or set of oligonucleotides, which is capable of encoding a fragment of the PTPL1 or GLM-2 coding sequences, or a PTPL1 or GLM-2 anti-sense complement of such an oligonucleotide or set of oligonucleotides, may be synthesized by means well known in the art (see, for example, *Synthesis and Application of DNA and RNA*, S. A. Narang, ed., 1987, Academic Press, San Diego, Calif.) and employed as a probe to identify and isolate a cloned PTPL1 or GLM-2 sequence, variant or fragment thereof by techniques known in the art. As noted above, a unique or substantially characteristic fragment of a PTPL1 or GLM-2 sequence disclosed herein is preferred. Techniques of nucleic acid hybridization and clone identification are disclosed by Sambrook, et al., *Molecular Cloning, A Laboratory Manual*, 2d ed., Cold Spring Harbor Laboratory Press, Plainview, N.Y. (1989), and by Hames, B. D., et al., in *Nucleic Acid Hybridization, A Practical Approach*, IRL Press, Washington, D.C. (1985). To facilitate the detection of a desired PTPL1 or GLM-2 nucleic acid sequence, whether for cloning purposes or for the mere detection of the presence of PTPL1 or GLM-2 sequences, the above-described probes may be labeled with a detectable group. Such a detectable group may be any material having a detectable physical or chemical property. Such materials have been well-developed in the field of nucleic acid hybridization and in general most any label useful in such methods can be applied to the present invention. Particularly useful are radioactive labels. Any radioactive label may be employed which provides for an adequate signal and has a sufficient half-life. If single stranded, the oligonucleotide may be radioactively labeled using kinase reactions. Alternatively, oligonucleotides are also useful as nucleic acid hybridization probes when labeled with a non-radioactive marker such as biotin, an enzyme or a fluorescent group. See, for example, Leary, J. J., et al., *Proc. Natl. Acad. Sci. (USA)* 80:4045 (1983); Renz, M. et al., *Nucl. Acids Res.* 12:3435 (1984); and Renz, M., *EMBO J.* 6:817 (1983).

By using the sequences disclosed herein as probes or as primers, and techniques such as PCR cloning and colony/ plaque hybridization, it is within the abilities of one skilled in the art to obtain human allelic variants and sequences substantially similar or homologous to PTPL1 or GLM-2 nucleic acid sequences from species including mouse, rat, rabbit and non-human primates. Thus, the present invention is further directed to mouse, rat, rabbit and primate PTPL1 and GLM-2.

In particular the protein sequences disclosed herein for PTPL1 and GLM-2 may be used to generate sets of degenerate probes or PCR primers useful in isolating similar and potentially evolutionarily similar sequences encoding proteins related to the PTPL1 or GLM-2 PTPs. Such degenerate probes may not be substantially similar to any fragments of the PTPL1 or GLM-2 nucleic acid sequences but, as derived from the protein sequences disclosed herein, are intended to fall within the spirit and scope of the claims.

Antibodies to PTPL1 and GLM-2.

In the following description, reference will be made to various methodologies well-known to those skilled in the art of immunology. Standard reference works setting forth the general principles of immunology include Catty, D. *Antibodies, A Practical Approach*, Vols. I and II, IRL Press, Washington, D.C. (1988); Klein, J. *Immunology: The Science of Cell-Noncell Discrimination*, John Wiley & Sons, New York (1982); Kennett, R., et al. in *Monoclonal Antibodies, Hybridoma: A New Dimension in Biological Analyses*, Plenum Press, New York (1980); Campbell, A., "Monoclonal Antibody Technology," in *Laboratory Techniques in Biochemistry and Molecular Biology*, Volume 13 (Burdon, R., et al., eds.), Elsevier, Amsterdam (1984); and Eisen, H. N., in *Microbiology*, 3rd Ed. (Davis, B. D., et al., eds.) Harper & Row, Philadelphia (1980).

The antibodies of the present invention are prepared by any of a variety of methods. In one embodiment, purified PTPL1 or GLM-2 PTP, a variant or a fragment thereof, is administered to an animal in order to induce the production of sera containing polyclonal antibodies that are capable of binding the PTP, variant or fragment thereof.

The preparation of antisera in animals is a well known technique (see, for example, Chard, *Laboratory Techniques in Biology*, "An Introduction to Radioimmunoassay and Related Techniques," North Holland Publishing Company (1978), pp. 385–396; and *Antibodies, A Practical Handbook*, Vols. I and II, D. Catty, ed., IRL Press, Washington, D.C. (1988)). The choice of animal is usually determined by a balance between the facilities available and the likely requirements in terms of volume of the resultant antiserum. A large species such as goat, donkey and horse may be preferred, because of the larger volumes of serum readily obtained. However, it is also possible to use smaller species such as rabbit or guinea pig which often yield higher titer antisera. Usually, a subcutaneous injection of the antigenic material (the protein or fragment thereof or a hapten-carrier protein conjugate) is used. The detection of appropriate antibodies may ba carried out by testing the antisera with appropriately labeled tracer-containing molecules. Fractions that bind tracer-containing molecules are then isolated and further purified if necessary.

Cells expressing PTPL1 or GLM-2 PTP, a variant or a fragment thereof, or, a mixture of such proteins, variants or fragments, can be administered to an animal in order to induce the production of sera containing polyclonal antibodies, some of which will be capable of binding the PTPL1 or GLM-2 PTP. If desired, such PTPL1 or GLM-2 antibody may be purified from other polyclonal antibodies by standard protein purification techniques and especially by affinity chromatography with purified PTPL1 or GLM-2 protein or variants or fragments thereof.

A PTPL1 or GLM-2 protein fragment may also be chemically synthesized and purified by HPLC to render it substantially pure. Such a preparation is then introduced into an animal in order to produce polyclonal antisera of high specific activity. In a preferred embodiment, the protein may be coupled to a carrier protein such as bovine serum albumin or keyhole limpet hemocyanin (KLH), and and used to immunogenize a rabbit utilizing techniques well-known and commonly used in the art. Additionally, the PTPL1 or GLM-2 protein can be admixed with an immunologically inert or active carrier. Carriers which promote or induce immune responses, such as Freund's complete adjuvant, can be utilized.

Monoclonal antibodies can be prepared using hybridoma technology (Kohler et al., *Nature* 256:495 (1975); Kohler, et al., *Eur. J. Immunol.* 6:511 (1976); Kohler, et al., *Eur. J. Immunol.* 6:292 (1976); Hammerling, et al., in *Monoclonal Antibodies and T-Cell Hybridomas*, Elsevier, N.Y., pp. 563–681 (1981)). In general, such procedures involve immunizing an animal with PTPL1 or GLM-2 PTP, or a variant or a fragment thereof. The splenocytes of such animals are extracted and fused with a suitable myeloma cell line. After fusion, the resulting hybridoma cells are selectively maintained in HAT medium, and then cloned by limiting dilution as described by Wands, J. R., et al., *Gastro-enterology* 80:225–232 (1981), which reference is herein incorporated by reference. The hybridoma cells obtained through such a selection are then assayed to identify clones which secrete antibodies capable of binding the PTP and/or the PTP antigen. The proliferation of transfected cell lines is potentially more promising than classical myeloma technology, using methods available in the art.

Through application of the above-described methods, additional cell lines capable of producing antibodies which recognize epitopes of the PTPL1 and GLM-2 PTPs can be obtained.

These antibodies can be used clinically as markers (both quantitative and qualitative) of the PTPL1 and GLM-2 PTPs in brain, blastoma or other tissue. Additionally, the antibodies are useful in a method to assess PTP function in cancer or other patients.

The method whereby two antibodies to PTPL1 were produced is outlined in Example 5.

Substantially pure PTPL1 and GLM-2 proteins

A variety of methodologies known in the art can be utilized to obtain a purified PTPL1 or GLM-2 PTP. In one method, the protein is purified from tissues or cells which naturally produce the protein. Alternatively, an expression vector may be introduced into cells to cause production of the protein. For example, human fibroblast or monkey kidney COS cells may be employed. In another embodiment, mRNA transcripts may be microinjected into cells, such as Xenopus oocytes or rabbit reticulocytes. In another embodiment, mRNA is used with an in vitro translation system. In preferred embodiment, bacterial cells are used to make large quantities of the protein. In a particularly preferred embodiment, a fusion protein, such as a bacterial GST fusion (Pharmacia) may be employed, the fusion product purified by affinity chromatography, and the PTPL1 or GLM-2 protein may be released from the hybrid by cleaving the amino acid sequence joining them.

In light of the present disclosure, one skilled in the art can readily follow known methods for isolating proteins in order to obtain substantially pure PTPL1 or GLM-2 PTP, free of natural contaminants. These include, but are not limited to, immunochromatography, HPLC, size-exclusion chromatography, ion-exchange chromatography, and immuno-affinity chromatography.

Determinations of purity may be performed by physical characterizations (such as molecular mass in size fractionation), immunological techniques or enzymatic assays.

PTPL1 or GLM-2 PTP, variants or fragments thereof, purified in the above manner, or in a manner wherein equivalents of the above sequence of steps are utilized, are useful in the preparation of polyclonal and monoclonal antibodies, for pharmaceutical preparations to inhibit or enhance PTP activity and for in vitro dephosphorylations.

Variants of PTPL1 and GLM-2 nucleic acids and proteins

Variants of PTPL1 or GLM-2 having an altered nucleic acid sequence can be prepared by mutagenesis of the DNA. This can be accomplished using one of the mutagenesis procedures known in the art.

Preparation of variants of PTPL1 or GLM-2 are preferably achieved by site-directed mutagenesis. Site-directed mutagenesis allows the production of variants of these PTPs through the use of a specific oligonucleotide which contains the desired mutated DNA sequence.

Site-directed mutagenesis typically employs a phage vector that exists in both a single-stranded and double-stranded form. Typical vectors useful in site-directed mutagenesis include vectors such as the M13 phage, as disclosed by Messing, et al., Third Cleveland Symposium on Macromolecules and *Recombinant DNA*, A. Walton, ed., Elsevier, Amsterdam (1981), the disclosure of which is incorporated herein by reference. These phage are commercially available and their use is generally well known to those skilled in the art. Alternatively, plasmid vectors containing a single-stranded phage origin of replication (Veira, et al., *Meth. Enzymol.* 153:3 (1987)) may be employed to obtain single-stranded DNA.

In general, site-directed mutagenesis in accordance herewith is performed by first obtaining a single-stranded vector that includes within its sequence the DNA sequence which is to be altered. An oligonucleotide primer bearing the desired mutated sequence is prepared, generally synthetically, for example by the method of Crea, et al., *Proc. Natl. Acad. Sci.* (*USA*) 75:5765 (1978). The primer is then annealed with the single-stranded vector containing the sequence which is to be altered, and the created vector is incubated with a DNA-polymerizing enzyme such as *E. coli* polymerase I Klenow fragment in an appropriate reaction buffer. The polymerase will complete the synthesis of a mutation-bearing strand. Thus, the second strand will contain the desired mutation. This heteroduplex vector is then used to transform appropriate cells and clones are selected that contain recombinant vectors bearing the mutated sequence.

While the site for introducing a sequence variation is predetermined, the mutation per se need not be predetermined. For example, to optimize the performance of a mutation at a given site, random mutagenesis may be conducted at a target region and the newly generated sequences can be screened for the optimal combination of desired activity. One skilled in the art can evaluate the functionality of the variant by routine screening assays.

The present invention further comprises fusion products of the PTPL1 or GLM-2 PTPs. As is widely known, translation of eukaryotic mRNA is initiated at the codon which encodes the first methionine. The presence of such codons between a eukaryotic promoter and a PTPL1 or GLM-2 sequence results either in the formation of a fusion protein (if the ATG codon is in the same reading frame as the PTP encoding DNA sequence) or a frame-shift mutation (if the ATG codon is not in the same reading frame as the PTP encoding sequence). Fusion proteins may be constructed with enhanced immunospecificity for the detection of these PTPs. The sequence coding for the PTPL1 or GLM-2 PTP may also be joined to a signal sequence which will allow secretion of the protein from, or the compartmentalization of the protein in, a particular host. Such signal sequences may be designed with or without specific protease sites such that the signal peptide sequence is amenable to subsequent removal.

The invention further provides detectably labeled, immobilized and toxin conjugated forms of PTPL1 and GLM-2 PTPs, and variants or fragments thereof. The production of such labeled, immobilized or toxin conjugated forms of a protein are well known to those of ordinary skill in the art. While radiolabeling represents one embodiment, the PTPs or variants or fragments thereof may also be labeled using fluorescent labels, enzyme labels, free radical labels, avidin-biotin labels, or bacteriophage labels, using techniques known to the art (Chard, *Laboratory Techniques in Biology*, "An Introduction to Radioimmunoassay and Related Techniques," North Holland Publishing Company (1978)).

Typical fluorescent labels include fluorescein isothiocyanate, rhodamine, phycoerythrin, phycocyanin, allophycocyanin, and fluorescamine.

Typical chemiluminescent compounds include luminol, isoluminol, aromatic acridinium esters, imidazoles, and the oxalate esters.

Typical bioluminescent compounds include luciferin, and luciferase. Typical enzymes include alkaline phosphatase, β-galactosidase, glucose-6-phosphate dehydrogenase, maleate dehydrogenase, glucose oxidase, and peroxidase.

Transformed cells, cell lines and hosts

To transform a mammalian cell with the nucleic acid sequences of the invention many vector systems are available depending upon whether it is desired to insert the recombinant DNA construct into the host cell's chromosomal DNA, or to allow it to exist in an extrachromosomal form. If the PTPL1 or GLM-2 PTP coding sequence, along with an operably joined regulatory sequence is introduced into a recipient eukaryotic cell as a non-replicating DNA (or RNA) molecule, the expression of PTPL1 or GLM-2 PTP may occur through the transient expression of the introduced sequence. Such a non-replicating DNA (or RNA) molecule may be a linear molecule or, more preferably, a closed covalent circular molecule which is incapable of autonomous replication.

In a preferred embodiment, genetically stable transformants may be constructed with vector systems, or transformation systems, whereby recombinant PTPL1 or GLM-2 PTP DNA is integrated into the host chromosome. Such integration may occur de novo within the cell or, in a most preferred embodiment, be assisted by transformation with a vector which functionally inserts itself into the host chromosome with, for example, retro vectors, transposons or other DNA elements which promote integration of DNA sequences in chromosomes. A vector is employed which is capable of integrating the desired sequences into a mammalian host cell chromosome. In a preferred embodiment, the transformed cells are human fibroblasts. In another preferred embodiment, the transformed cells are monkey kidney COS cells.

Cells which have stably integrated the introduced DNA into their chromosomes may be selected by also introducing one or more markers which allow for selection of host cells which contain the expression vector in the chromosome, for example the marker may provide biocide resistance, e.g., resistance to antibiotics, or heavy metals, such as copper, or the like. The selectable marker can either be directly linked to the DNA sequences to be expressed, or introduced into the same cell by co-transfection.

In another embodiment, the introduced sequence is incorporated into a vector capable of autonomous replication in the recipient host. Any of a wide variety of vectors may be employed for this purpose, as outlined below.

Factors of importance in selecting a particular plasmid or vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred eukaryotic plasmids include those derived from the bovine papilloma virus, SV40, and, in yeast, plasmids containing the 2-micron circle, etc., or their derivatives. Such plasmids are well known in the art (Botstein, D., et al., *Miami Wntr. Svmp.* 19:265–274 (1982); Broach, J. R., in *The Molecular Biology of the Yeast Saccharomyces: Life Cycle and Inheritance*, Cold Spring Harbor Laboratory, Cold Spring Harbor, N.Y., p. 445–470 (1981); Broach, J. R., *Cell* 28:203–204 (1982); Bolion, D. P., et al., *J. Clin. Hematol. Oncol.* 10:39–48 (1980); Maniatis, T., in *Cell Biology: A Comprehensive Treatise, Vol. 3, Gene Expression*, Academic Press, New York, pp. 563–608 (1980)), and are commercially available. For example, mammalian expression vector systems which utilize the MSV-LTR promoter to drive expression of the cloned gene and with which it is possible to co-transfect with a helper virus to amplify plasmid copy number and to integrate the plasmid into the chromosomes of host cells have been described (Perkins, A. S., et al., *Mol. Cell Biol.* 3:1123 (1983); Clontech, Palo Alto, Calif.).

Once the vector or DNA sequence is prepared for expression, it is introduced into an appropriate host cell by any of a variety of suitable means, including transfection. After the introduction of the vector, recipient cells may be grown in a selective medium, which selects for the growth of vector-containing cells. Expression of the cloned nucleic acid sequence(s) results in the production of PTPL1 or GLM-2 PTP, or the production of a variant or fragment of the PTP, or the expression of a PTPL1 or GLM-2 anti-sense RNA, or a variant or fragment thereof. This expression can take place in a transient manner, in a continuous manner, or in a controlled manner as, for example, expression which follows induction of differentiation of the transformed cells (for example, by administration of bromodeoxyuracil to neuroblastoma cells or the like).

In another embodiment of the invention the host is a human host. Thus, a vector may be employed which will introduce into a human with deficient PTPL1 or GLM-2 PTP activity, operable PTPL1 or GLM-2 sequences which can supplement the patient's endogenous production. In another embodiment, the patient suffers from a cancer caused by an oncogene which is a protein tyrosine kinase (PTK). A vector capable of expressing the PTPL1 or GLM-2 protein is introduced within the patient to counteract the PTK activity.

The recombinant PTPL1 or GLM-2 PTP cDNA coding sequences, obtained through the methods above, may be used to obtain PTPL1 or GLM-2 anti-sense RNA sequences. An expression vector may be constructed which contains a DNA sequence operably joined to regulatory sequences such that the DNA sequence expresses the PTPL1 or GLM-2 anti-sense RNA sequence. Transformation with this vector results in a host capable of expression of a PTPL1 or GLM-2 anti-sense RNA in the transformed cell. Preferably such expression occurs in a regulated manner wherein it may be induced and/or repressed as desired. Most preferably, when expressed, anti-sense PTPL1 or GLM-2 RNA interacts with an endogenous PTPL1 or GLM-2 DNA or RNA in a manner which inhibits or represses transcription and/or translation of the PTPL1 or GLM-2 PTP DNA sequences and/or mRNA transcripts in a highly specific manner. Use of anti-sense RNA probes to block gene expression is discussed in Lichtenstein, C., *Nature* 333:801–802 (1988).

Assays for Agonists and Antagonists

The cloning of PTPL1 and GLM-2 now makes possible the production and use of high through-put assays for the identification and evaluation of new agonists (inducers/enhancers) and antagonists (repressors/inhibitors) of PTPL1 or GLM-2 PTPs for therapeutic strategies using single or combinations of drugs. The assay may, for example, test for PTPL1 or GLM-2 PTP activity in transfected cells (e.g. fibroblasts) to identify drugs that interfere with, enhance, or otherwise alter the expression or regulation of these PTPs. In addition, probes developed for the disclosed PTPL1 and GLM-2 nucleic acid sequences or proteins (e.g. DNA or RNA probes or or primers or antibodies to the proteins) may be used as qualitative and/or quantitative indicators for the PTPs in cell lysates, whole cells or whole tissue.

In a preferred embodiment, human fibroblast cells are transformed with the PTPL1 or GLM-2 PTP sequences and vectors disclosed herein. The cells may then be treated with a variety of compounds to identify those which enhance or inhibit PTPL1 or GLM-2 transcription, translation, or PTP activity. In addition, assays for PDGF (platelet derived growth factor) signalling, cell growth, chemotaxis, and actin reorganization are preferred to assess a compound's affect on PTPL1 or GLM-2 PTP transcription, translation or activity.

In another embodiment, the ability of a compound to enhance or inhibit PTPL1 or GLM-2 PTP activity is assayed in vitro. Using the substantially pure PTPL1 or GLM-2 PTPs disclosed herein, and a detectable phosphorylated substrate, the ability of various compounds to enhance or inhibit the phosphatase activity of PTPL1 or GLM-2 may be assayed. In a particularly preferred embodiment the phosphorylated substrate is para-nitrylphenyl phosphate (which turns yellow upon dephosphorylation).

In another embodiment, the ability of a compound to enhance or inhibit PTPL1 or GLM-2 transcription is assayed. Using the PTPL1 or GLM-2 cDNA sequences disclosed herein, one of ordinary skill in the art can clone the 5' regulatory sequences of the PTPL1 or GLM-2 genes. These regulatory sequences may then be operably joined to a sequence encoding a marker. The marker may be an enzyme with an easily assayable activity or may cause the host cells to change phenotypically or in their sensitivity or resistance to certain molecules. A wide variety of markers are known to those of ordinary skill in the art and appropriate markers may be chosen depending upon the host used. Compounds which may alter the transcription of PTPL1 or GLM-2 PTP may be tested by exposing cells transformed with the PTPL1 or GLM-2 regulatory sequences operably joined to the marker and assaying for increased or decreased expression of the marker.

The following examples further describe the particular materials and methods used in developing and carrying out some of the embodiments of the present invention. These examples are merely illustrative of techniques employed to date and are not intended to limit the scope of the invention in any manner.

EXAMPLE 1

Original Cloning of PTPL1

All cells, unless stated otherwise, were cultured in Dulbeco Modified Eagles Medium (DMEM Gibco) supplemented with 10% Fetal Calf Serum (FCS, Flow Laboratories), 100 units of penicillin, 50 µg/ml streptomycin and glutamine. The human glioma cell line used was U-343 MGa 31L (Nister, M., et al., (1988) *Cancer Res.* 48:3910–3918). The AG1518 human foreskin fibroblasts were from the Human Genetic Mutant Cell Repository, Institute for Medical Research, Camden, N.J.

RNA was prepared from U-343 MGa 31L cells or AG1518 human fibroblasts by guanidine thiocyanate (Merck, Darmstadt) extraction (Chirgwin et al., 1979). Briefly, cells were harvested, washed in phosphate buffered saline (PBS), and lysed in 4 M guanidine thiocyanate containing 25 mM sodium citrate (pH 7.0) and 0.1 M 2-mercaptoethanol. RNA was sedimented through 5.7 M cesium chloride, the RNA pellet was then dissolved in 10 mM Tris hydrochloride (pH 7.5), 5 mM EDTA (TE buffer), extracted with phenol and chloroform, precipitated with ethanol, and the final pellet stored at −70° C. or resuspended in TE buffer for subsequent manipulations. Polyadenylated [poly(A)+] RNA was prepared by chromatography on oligo (dT)-cellulose as described in Maniatis et al., 1982.

Poly(A)+RNA (5 µg) from U-343 MGa 31 L cells was used to make a cDNA library by oligo (dT)-primed cDNA synthesis using an Amersham λgt10 cDNA cloning system. Similarly, a random and oligo (dT) primed cDNA library was prepared from AG1518 fibroblasts using 5 µg of poly (A)+RNA, a RiboClone cDNA synthesis system (Promega Corporation, Madison, Wis., USA), a Lambda ZAPII synthesis kit (Stratagene), and Gigapack Gold II packaging extract (Stratagene). Degenerate primers were designed based on conserved amino acid-regions of known PTP sequences and were synthesized using a Gene Assembler Plus (Pharmacia-LKB). Sense oligonucleotides corresponded to the sequences FWRM (SEQ ID NO:5) I/V WEQ (5'-TTCTGG A/C GNATGATNTGGGAACA-3', 23 mer (SEQ ID NO:6) with 32-fold degeneracy) and KC (SEQ ID NO:7) A/D Q/E YWP (5'-AA A/G TG C/T GANCAGTA C/T TGGCC-3', 20mer (SEQ ID NO:8) with 32-fold degeneracy), and the anti-sense oligonucleotide was based on the sequence HCSAG (SEQ ID NO:9) V/I G (5'-CCNACNCC A/C GC A/G CTGCAGTG-3', 20mer (SEQ ID NO:10) with 64-fold degeneracy). Unpackaged template cDNA from the U-343 MGa 31L library (100 ng) was amplified using Taq polymerase (Perkin Elmer-Cetus) and 100 ng of either sense primer in combination with 100 ng of the anti-sense primer as described (Saiki et al., 1985). PCR was carried out for 25 cycles each consisting of denaturation at 94° C. for 30 sec, annealing at 40° C. for 2 min followed by 55° C. for 1 min, and extension at 72° C. for 2 min. The PCR products were separated on a 2.0% low gelling temperature agarose gel (FMC BioProducts, Rockland, USA) and DNA fragments of approximately 368 base pairs (with FWRM sense primer (SEQ ID NO:6)) and approximately 300 bp (with KC A/D Q sense primer (SEQ ID NO:8)) were excised, eluted from the gel, subcloned into a T-tailed vector (TA Cloning Kit, Invitrogen Corporation, San Diego, Calif., USA), and sequenced.

Nucleotide sequences from several of the PCR cDNA clones analysed were representative of both cytoplasmic and receptor types of PTPs. Thirteen clones encoded cytoplasmic enzymes including MEG (Gu et al., 1991; 8 clones), PTPH1 (Yang and Tonks, 1991; 2 clones), P19PTP (den Hertog et al., 1992), and TC-PTP (Cool et al., 1989, one clone); 11 clones encoded receptor-type enzymes such as HPTP-α (Kruger et al., 1990, 7 clones), HPTP-γ (Kruger et al., 1990, 3 clones) and HPTP-δ (Kruger et al., 1990, 1 clone), and three clones defined novel PTP sequences. Two of these were named PTPL1 and GLM-2.

The U-343 MGa 31L cDNA library was screened with $^{32}$P-random prime-labeled (Megaprime Kit, Amersham) approximately 368 bp inserts corresponding to PTPL1 as described elsewhere (Huynh et al., 1986); clone λ6.15 was isolated, excised from purified phage DNA by Eco RI (Biolabs) digestion and subcloned into pUC18 for sequencing. All other cDNA clones were isolated from the AG1518 human fibroblast cDNA library which was screened with $^{32}$P-labeled λ6.15 insert and with subsequently isolated partial cDNA clones.

Double-stranded plasmid DNA was prepared by a single-tube mini preparation method (Del Sal et al., 1988) or using Magic mini or maxiprep kits (Promega) according to the manufacturer's specifications. Double-stranded DNA was denatured and used as template for sequencing by the dideoxynucleotide chain-termination procedure with T7 DNA polymerase (Pharmacia-LKB), and M13-universal and reverse primers or synthetic oligonucleotides derived from the cDNA sequences being determined. The complete 7395 bp open reading frame of PTPL1, was derived from six overlapping cDNA clones totalling 8040 bp and predicts a protein of 2465 amino acids with an approximate molecular mass of 275 kDa. The 8040 bp sequence is disclosed as SEQ ID NO:1.

EXAMPLE 2

Original Cloning of GLM-2

The human glioma cell line U-343 MGa 31L (Nister, M., et al., (1988) *Cancer Res.* 48:3910–3918) was cultured in Dulbecco's Modified Eagles Medium (DMEM Gibco) supplemented with 10% Fetal Calf Serum (FCS, Flow Laboratories), 100 units of penicillin, 50 µg/ml streptomycin and 2 mM glutamine.

Total RNA was prepared from U-343 MGa 31L cells by guanidine thiocyanate (Merck, Darmstadt) extraction (Chirgwin, et al., 1979). Briefly, cells were harvested, washed in phosphate buffered saline (PBS), and lysed in 4 M guanidine thiocyanate containing 25 mM sodium citrate (pH 7.0) and 0.1 M 2-mercaptoethanol. RNA was sedimented through 5.7 M cesium chloride, the RNA pellet was then dissolved in 10 mM Tris hydrochloride (pH 7.5), 5 mM EDTA (TE buffer), extracted with phenol and chloroform, precipitated with ethanol, and the final pellet stored at −70° C. or resuspended in TE buffer for subsequent manipulations. Polyadenylated [poly(A)+] RNA was prepared by chromatography on oligo (dT)-cellulose as described in Maniatis et al. (1982).

Poly(A)+RNA (5 μg) isolated from U-343 MGa 31L cells was used to make a cDNA library by oligo (dT)-primed cDNA synthesis using an Amersham λgt10 cDNA cloning system. Degenerate primers were designed based on conserved amino acid regions of known PTP sequences, and synthesized using a Gene Assembler Plus (Pharmacia-LKB). Sense oligonucleotides corresponded to the sequences FWRM (SEQ ID NO:5) I/V WEQ (5'-TTCTGG A/C GNATGATNTGGGAACA-3', 23mer (SEQ ID NO:6) with 32-fold degeneracy=primer P1) and KC (SEQ ID NO:7) A/D Q/E YWP (5'-AA A/G TG C/T GANCAGTA C/T TGGCC-3', 20mer (SEQ ID NO:8) with 32-fold degeneracy=primer P2), and the anti-sense oligonucleotide was based on the sequence HCSAG (SEQ ID NO:9) V/I G (5'-CCNACNCC A/C GC A/G CTGCAGTG-3', 20mer (SEQ ID NO:10) with 64-fold degeneracy=primer P3). Unpackaged template cDNA from the U-343 MGa 31L library (100 ng) was amplified using Taq polymerase (Perkin Elmer-Cetus) and 100 ng of either sense primer in combination with 100 ng of the anti-sense primer as described (Saiki, et al., 1985). PCR was carried out for 25 cycles each consisting of denaturation at 94° C. for 30 sec, annealing at 40° C. for 2 min followed by 55° C. for 1 min, and extension at 72° C. for 2 min. The PCR products were separated on a 2.0% low gelling temperature agarose gel (FMC BioProducts, Rockland, USA) and DNA fragments of approximately 368 base pairs (with FWRM sense primer) and approximately 300 bp (with KC A/D Q sense primer) were excised, eluted from the gel, subcloned into a T-tailed vector (TA Cloning Kit, Invitrogen Corporation, San Diego, Calif., USA), and sequenced. Double-stranded plasmid DNA was prepared by a single-tube mini preparation method (Del Sal, et al., 1988) or by using Magic mini or maxiprep kits (Promega) according to the manufacturer's specifications. Double-stranded DNA was denatured and used as template for sequencing by the dideoxynucleotide chain-termination procedure (Sanger, et al., 1977) with T7 DNA polymerase (Pharmacia-LKB), and M13-universal and reverse primers or, in the case of cDNA clones isolated from the brain cDNA library, using also synthetic oligonucleotides derived from the cDNA sequences being determined.

A human brain cDNA library constructed in λgt10 (Clontech, Calif.) was screened as described elsewhere (Huynh, et al., 1986) with $^{32}$P-random prime-labeled (Megaprime Kit, Amersham) approximately 360 bp inserts corresponding to GLM-2. Clone HBM1 was isolated, excised from purified phage DNA by Eco RI (Biolabs) digestion and subcloned into the plasmid vectors pUC18 or Bluescript (Stratagene) for sequencing. The resulting sequence is disclosed as SEQ ID NO:2.

EXAMPLE 3

Tissue-specific Expression of PTPL1

Total RNA (20 μg) or poly(A)+RNA (2 μg) denatured in formaldehyde and formamide was separated by electrophoresis on a formaldehyde/1% agarose gel and transferred to nitrocellulose. The filters were hybridized for 16 hrs at 42° C. with $^{32}$P-labeled probes in a solution containing 5× standard saline citrate (SSC; 1× SSC is 50 mM sodium citrate, pH 7.0, 150 mM sodium chloride), 50% formamide, 0.1% sodium dodecyl sulfate (SDS), 50 mM sodium phosphate and 0.1 mg/ml salmon sperm DNA. All probes were labeled by random priming (Feinberg and Vogelstein, 1983) and unincorporated $^{32}$P was removed by Sephadex G-25 (Pharmacia-LKB) chromatography. Human tissue blots (Clontech, Calif.) were hybridized with PTPL1 specific probes according to manufacturer's specifications. Filters were washed twice for 30 min at 60° C. in 2× SSC/0.1% SDS, once for 30 min at 60° C. in 0.5× SSC/0.1% SDS, and exposed to X-ray film (Fuji, XR) with intensifying screen (Cronex Lighting Plus, Dupont) at −70° C.

Northern blot analysis of RNAs from various human tissues showed that the 9.5 kb PTPL1 transcript is expressed at different levels with kidney, placenta, ovaries and testes showing high expression, compared to medium expression in lung, pancreas, prostate and brain tissues, low in heart, skeletal muscle, spleen, liver, small intestine and colon and virtually no detectable expression in leukocytes.

EXAMPLE 4

Tissue-specific Expression of GLM-2

To investigate the expression of GLM-2 mRNA in human tissues, Northern blot analysis was performed on a commercially available filter (Clontech, Calif.) containing mRNAs from human heart, brain, placenta, lung, liver, skeletal muscle, kidney and pancreas tissue. The filter was hybridized according to manufacturer's specifications with $^{32}$P-labeled GLM-2 PCR product as probe, washed twice for 30 min at 60° C. in 2× standard saline citrate (SSC; 1× SSC is 50 mM sodium citrate, pH 7.0, 150 mM sodium chloride), containing 0.1% sodium dodecyl sulfate (SDS), once for 30 min at 60° C. in 0.5× SSC/0.1% SDS, and exposed to X-ray film (Fuji, RX) with intensifying screen (Cronex Lighting Plus, Dupont) at −70° C.

EXAMPLE 5

Production of PTPL1 specific antisera

Rabbit antisera denoted αL1A and αL1B were prepared against peptides corresponding to amino acid residues 1802 to 1823 (SEQ ID NO:1) (PAKSDGRLKPGDRLIKVNDTDV) and 450 to 470 (SEQ ID NO:1) (DETLSQGQSQRPSRQYETPFE), respectively, of PTPL1. The peptides were synthesized in an Applied Biosystems 430A Peptide Synthesizer using t-butoxycarbonyl chemistry and purified by reverse phase high performance liquid chromatography. The peptides were coupled to keyhole limpet hemocyanin (Calbiochem-Behring) using glutaraldehyde, as described (Gullick, W. J., et al., (1985) *EMBO J.* 4:2869–2877), and then mixed with Freund's adjuvant and used to Immunize a rabbit. The αL1A antiserum was purified by affinity chomatography on protein A-Sepharose CL4B (Pharmacia-LKB) as described by the manufacturer.

EXAMPLE 6

Transfection of the PTPL1 cDNA into COS-1 Cells

The full length PTPL1 cDNA was constructed using overlapping clones and cloned into the SV40-based expression vector pSV7d (Truett, M. A., et al., (1985) *DNA* 4:333–349), and transfected into COS-1 cells by the calcium phosphate precipitation method (Wigler, M., et al., (1979) *Cell* 16:777–785). Briefly, cells were seeded into 6-well cell culture plates at a density of 5×10$^5$ cells/well, and transfected the following day with 10 μg of plasmid. After overnight incubation, cells were washed three times with a buffer containing 25 mM Tris-HCl, pH 7.4, 138 mM NaCl, 5 mM KCl, 0.7 mM CaCl$_2$, 0.5 mM MgCl$_2$ and 0.6 mM Na$_2$HPO$_4$, and then incubated with Dulbecco's modified Eagle's medium containing 10% fetal calf serum and antibiotics. Two days after transfection, the cells were used for metabolic labeling followed by immunoprecipitation and SDS-gel electrophoresis, or immunoprecipitation followed by dephosphorylation experiments.

EXAMPLE 7

Metabolic Labeling, Immunoprecipitation and Electrophoresis of PTPL1

Metabolic labeling of COS-1 cells, AG1518 cells, PC-3 cells, CCL-64 cells, A549 cells and PAE cells was performed for 4 h in methionine- and cysteine-free MCDB 104 medium (Gibco) with 150 µCi/ml of [$^{35}$S]methionine and [$^{35}$S]cysteine (in vivo labeling mix; Amersham). After labeling, the cells were solubilized in a buffer containing 20 mM Tris-HCl, pH 7.4, 150 mM NaCl, 10 mM EDTA, 0.5% Triton X-100, 0.5% deoxycholate, 1.5% Trasylol (Bayer) and 1 mM phenylmethylsulfonyl fluoride (PMSF; Sigma). After 15 min on ice, cell debris was removed by centrifugation. Samples (1 ml) were then incubated for 1.5 h at 4° C. with either αL1A antibodies or αL1A antibodies preblocked with 10 µg of peptide. Immune complexes were then mixed with 50 µl of a protein A-Sepharose (Pharmacia-LKB) slurry (50% packed beads in 150 mM NaCl, 20 mM Tris-HCl, pH 7.4, 0.2% Triton X-100) and incubated for 45 min at 4° C. The beads were pelleted and washed four times with washing buffer (20 mM Tris-HCl, pH 7.4, 500 mM NaCl, 1% Triton X-100, 1% deoxycholate and 0.2% SDS), followed by one wash in distilled water. The immune complexes were eluted by boiling for 5 min in the SDS-sample buffer (100 mM Tris-HCl, pH 8.8, 0.01% bromophenol blue, 36% glycerol, 4% SDS) in the presence of 10 mM dithiothreitol (DTT), and analyzed by SDS-gel electrophoresis using 4–7% polyacrylamide gels (Blobel, G., and Dobberstein, B. (1975) *J. Cell Biol.* 67:835–851). The gel was fixed, incubated with Amplify (Amersham) for 20 min, dried and subjected to fluorography.

EXAMPLE 8

Dephosphorylation Assay for PTPL1

COS-1 cells were lysed in 20 mM Tris-HCl, pH 7.4, 150 mM NaCl, 10 mM EDTA, 0.5% Triton X-100, 0.5% deoxycholate, 1.5% Trasylol, 1 mM PMSF and 1 mM DTT, for 15 min. Lysates were cleared by centrifugation, 3 µl of the antiserum αL1B, with or without preblocking with 10 µg peptide, were added and samples were incubated for 2 h at 4° C. Protein A-Sepharose slurry (25 µl) was then added and incubation was prolonged another 30 min at 4° C. The beads were pelleted and washed four times with lysis buffer and one time with dephosphorylation assay buffer (25 mM imidazole-HCl, pH 7.2, 1 mg/ml bovine serum albumin and 1 mM DTT), and finally resuspended in dephosphorylation assay buffer containing 2 µM myelin basic protein $^{32}$P-labeled on tyrosine residues by Baculo-virus expressed intracellular part of the insulin receptor, kindly provided by A. J. Flint (Cold Spring Harbor Laboratory) and M. M. Cobb (University of Texas). After incubation for indicated times at 30° C., the reactions were stopped with a charcoal mixture (Streull, M., et al., (1988) *J. Exp. Med.* 168:1523–1530) and the radioactivity in the supernatants was determined by Cerenkov counting. For each sample, lysate corresponding to 5 cm$^2$ of confluent cells was used.

It should be understood that the preceding is merely a detailed description of certain preferred embodiments and examples of particular laboratory embodiments. It therefore should be apparent to those skilled in the art that various modifications and equivalents can be made without departing from the spirit or scope of the invention as defined in the appended claims.

---

What is claimed is:

1. An isolated nucleic acid molecule comprising
   (a) nucleic acid molecules which hybridize under stringent conditions to a nucleic acid molecule consisting of the nucleotide sequence of SEQ ID NO:2, and which encode a naturally occurring GLM-2 protein tyrosine phosphatase, wherein said stringent conditions are hybridization at 50–65° C., 5X SSPC, 50% formamide; wash 50–65° C., 5X SSPC; or wash at 60° C., 0.5X SSC, 0.1% SDS.
   (b) nucleic acid molecules that differ from the nucleic acid molecules of (a) in codon sequence due to the degeneracy of the genetic code,
   (c) complements of (a) and (b), that are at least approximately 300 nucleotides in length or
   (d) fragments of (a) or (b) encoding a protein with protein tyrosine phosphatase activity.

2. The isolated nucleic acid molecule of claim 1, wherein the isolated nucleic acid molecule encodes a protein tyrosine phosphatase comprising the amino acid sequence as set forth in SEQ ID NO:4.

3. The isolated nucleic acid molecule of claim 1, wherein said isolated nucleic acid molecule comprises SEQ ID NO:2, wherein said fragment encodes a protein with protein tyrosine phosphatase activity or a fragment of SEQ. ID. No:2.

4. An expression vector comprising the isolated nucleic acid molecule of any of claims 1–3 operably linked to a promoter.

5. A host cell transformed or transfected with the expression vector of claim 4.

6. A method for expressing nucleic acid molecules comprising
   operably joining the isolated nucleic acid molecule of claim 1 to a promoter,
   introducing the isolated nucleic acid molecule into a host cell,
   culturing the host cell under conditions which allow expression of the isolated nucleic acid, and
   isolating nucleic acid expression products of the isolated nucleic acid molecule from the host cell.

7. The method of claim 6, wherein, the isolated nucleic acid molecule of claim 1 encodes a polypeptide comprising the amino acid sequence as set forth in SEQ ID NO:4.

8. The method of claim 6, wherein the isolated nucleic acid molecule of claim 1 comprises a sequence selected is selected from the group consisting of SEQ ID NO:2, fragments of SEQ ID NO:2, which encode a protein with protein tyrosine phosphatase activity and antisense fragments of SEQ ID NO:2 that are at least approximately 300 nucleotides in length.

9. A method for expressing a polypeptide comprising
   operably joining the isolated nucleic acid molecule of claim 1 to a promoter, wherein the isolated nucleic acid molecule encodes a polypeptide,
   introducing the isolated nucleic acid molecule into a host cell and
   culturing the host cell under conditions which allow expression of the polypeptide.

10. The method of claim 9, further comprising isolating the encoded polypeptide.

11. The method of claim 9, wherein the encoded polypeptide comprises the amino acid sequence as set forth in SEQ ID No:4.

12. The method of claim 9, wherein said polypeptide consists of the amino acid sequence as set forth in SEQ ID NO:4.

* * * * *

UNITED STATES PATENT AND TRADEMARK OFFICE
CERTIFICATE OF CORRECTION

PATENT NO. : 6,066,472
DATED : May 23, 2000
INVENTOR(S) : Gonez et al.

It is certified that error appears in the above-identified patent and that said Letters Patent is hereby corrected as shown below:

Title page,
Under FOREIGN PATENT DOCUMENTS, add the following references:

-- WO 91/13173   09/05/91   Applied Biotechnology, Inc.
   CA 2086377    08/07/93   The Ontario Cancer Institute --

Under OTHER ART, add the following references:

-- OTHER ART

Saras et al., "Cloning and characterization of PTPL1, a protein tyrosine phosphatase with similarities to cytoskeletal-associated proteins," Sept. 30, 1994, pages 24082-24089, *J.Biol.Chem.*, vol.269, no. 39

Maekawa et al., "Molecular cloning of a novel protein-tyrosine phosphatase containing a membrane-binding domain and GLGF repeats," Jan. 10, 1994, pages 200-206, *Febs Letters*, vol. 337

Yung et al., "Differential expression of protein tyrosine phosphatases in primary human brain tumors," March 1993, page 527, *Proc. Am. Assoc. Cancer Research*, vol. 34

Lombroso et al., "Characterization of a protein-tyrosine phosphatase enriched in striatum," August 1991, pages 7242-7246, *Proc. Natl. Acad. Sciences*, vol. 88

Toews et al., "Evidence for involvement of tyrosine phosphorylation in serum-induced sensitization of cyclic AMP accumulation in C62B rat glioma cells," 1992, page A1075, *Faseb J.*, vol. 6. no. 4

Yang et al., "Isolation of a cDNA clone encoding a human protein-tyrosine phosphatase with homology to the cytoskeletal-associated proteins band 4.1, ezrin and talin," 1991, pages 5949-5953, *Proc. Natl. Acad. Sciences*, vol. 88

Gu et al., "Identification cloning, and expression of cytosolic megakaryocyte protein-tyrosine-phosphatase with sequence homology to cytoskeletal protein 4.1," 1991, pages 5867-5871, *Proc. Natl. Acad Sciences*, vol. 88

Adachi et al., "Molecular cloning and chromosomal mapping of a human protein-tyrosine phosphatase LC-PTP," Aug. 14, 1992, pages 1607-1615, *Biochem. Biophys. Res. Commun.*, vol 186, no. 3

UNITED STATES PATENT AND TRADEMARK OFFICE
CERTIFICATE OF CORRECTION

PATENT NO. : 6,066,472
DATED : May 23, 2000
INVENTOR(S) : Gonez et al.

Page 2 of 3

It is certified that error appears in the above-identified patent and that said Letters Patent is hereby corrected as shown below:

Sharma and Lombroso, *Journal of Biological Chemistry*, 270, pps 49-53 (1995)

Ogata et al., *Journal of Biological Chemistry*, 270, 2337-2343 (1995)

Hendriks et al., *Biochemical Journal* 305, pps 499-504 (1995) --

Column 10,
Line 33, replace the first appearance of "Homologous" with -- Homologues --.

Column 12,
Line 45, replace "SEQ ID NO:2" with -- SEQ ID NO:3 --.

Column 13,
Line 21, replace "am" with -- amino --.

Column 16,
Line 49, replace "employedN n" with -- employed. In --.

Column 25,
Line 51, replace "FWRM (SEQ ID NO:5)" with -- SEQ ID NO:5, FWRM --;
Line 52, replace "23 mer" with -- SEQ ID NO:6, 23 mer --;
Line 53, delete "(SEQ ID NO:6)";
Line 53, replace "KC (SEQ ID" with -- SEQ ID NO:7, KC --;
Line 54, delete "NO:7)";
Line 55, replace "20mer (SEQ ID NO:8)" with -- SEQ ID NO:8, 20mer --;
Line 57, replace "HCSAG (SEQ ID NO:9)" with -- SEQ ID NO:9, HCSAG --;
Line 58, replace "20mer (SEQ" with -- SEQ ID NO:10, 20mer --;
Line 59, delete "ID NO:10)".

Column 27,
Line 8, replace "FWRM (SEQ ID NO:5)" with -- SEQ ID NO:5, FWRM --;
Line 9, replace "23mer (SEQ ID NO:6)" with -- SEQ ID NO:6, 23 mer --;
Line 10, replace "KC (SEQ ID NO:7)" with -- SEQ ID NO:7, KC --;
Line 12, replace "20mer (SEQ ID NO:8)" with -- SEQ ID NO:8, 20mer --;
Line 14, replace "HCSAG (SEQ ID NO:9)" with -- SEQ ID NO:9, HCSAG --;
Lines 15-16, replace "20mer (SEQ ID NO:10)" with -- SEQ ID NO:10, 20mer --;

UNITED STATES PATENT AND TRADEMARK OFFICE
CERTIFICATE OF CORRECTION

PATENT NO. : 6,066,472
DATED : May 23, 2000
INVENTOR(S) : Gonez et al.

It is certified that error appears in the above-identified patent and that said Letters Patent is hereby corrected as shown below:

Column 95, claim 1,
Line 10, replace "SDS." with -- SDS, --.

Column 95, claim 3,
Line 25, replace "NO:2" with -- NO:2 or a fragment of SEQ NO:2 --.
Line 26, replace "SEQ. ID." with -- SEQ ID --.

Column 96, claim 7,
Line 7, replace "wherein," with -- wherein --.

Column 96, claim 8,
Line 12, delete "selected is".
Line 14, replace "SEQ ID NO:2," with -- SEQ ID NO:2 --.

Signed and Sealed this

Twenty-seventh of November, 2001

*Attest:*

NICHOLAS P. GODICI
*Attesting Officer*    *Acting Director of the United States Patent and Trademark Office*